United States Patent
Lovely et al.

(10) Patent No.: US 9,207,168 B2
(45) Date of Patent: *Dec. 8, 2015

(54) MONITORING FOR DISTURBANCE OF OPTICAL FIBER

(71) Applicant: Norscan Instruments Ltd., Winnipeg (CA)

(72) Inventors: Peter S. Lovely, Portland, OR (US); Michael James Brown, Winnipeg (CA)

(73) Assignee: Norscan Instruments Ltd., Winnipeg (CA)

( * ) Notice: Subject to any disclaimer, the term of this patent is extended or adjusted under 35 U.S.C. 154(b) by 34 days.

This patent is subject to a terminal disclaimer.

(21) Appl. No.: 13/747,326

(22) Filed: Jan. 22, 2013

(65) Prior Publication Data

US 2013/0188177 A1   Jul. 25, 2013

Related U.S. Application Data

(63) Continuation-in-part of application No. 13/355,406, filed on Jan. 20, 2012, now Pat. No. 8,736,826.

(51) Int. Cl.
*G01N 21/21* (2006.01)
*G01M 11/00* (2006.01)

(52) U.S. Cl.
CPC .............. *G01N 21/21* (2013.01); *G01M 11/30* (2013.01); *G01M 11/33* (2013.01); *G01M 11/332* (2013.01)

(58) Field of Classification Search
CPC ...... G01N 21/21; G01M 11/30; G01M 11/33; G01M 11/332–11/337; G01J 4/00; H04B 7/07; H04B 7/0705
USPC ........................................ 356/73.1; 398/9–16
See application file for complete search history.

(56) References Cited

U.S. PATENT DOCUMENTS

| | | | |
|---|---|---|---|
| 5,061,847 A | 10/1991 | Hazan et al. | |
| 6,317,240 B1 * | 11/2001 | Penninckx et al. | 398/147 |
| 7,142,737 B1 | 11/2006 | Murphy et al. | |
| 7,173,690 B2 | 2/2007 | Haran | |

(Continued)

OTHER PUBLICATIONS

Office action dated Sep. 9, 2013, from U.S. Appl. No. 13/355,406, 16 pp.

(Continued)

*Primary Examiner* — Gregory J Toatley
*Assistant Examiner* — Hina F Ayub
(74) *Attorney, Agent, or Firm* — Klarquist Sparkman, LLP

(57) ABSTRACT

Problems of excessive fading in systems for monitoring single-mode optical fiber for disturbances are addressed by launching into the fiber polarized light having at least two different predetermined launch states of polarization whose respective Stokes vectors are linearly-independent of each other; downstream from the first location, receiving the light from the fiber; analyzing the received light using polarization state analyzer having at least two different analyzer states of polarization that are characterized by respective Stokes vectors that are linearly-independent and detecting the analyzed light to provide corresponding detection signals; deriving from the detection signals measures of changes in polarization transformation properties of the fiber between different times that are invariant under a non-reflective unitary transformation on either the launch states or the detection states; and, on the basis of predefined acceptable physical disturbance criteria determining whether or not the measures are indicative of a reportable physical disturbance.

34 Claims, 20 Drawing Sheets

(56) References Cited

U.S. PATENT DOCUMENTS

| | | | |
|---|---|---|---|
| 7,206,469 B2 | 4/2007 | Murphy et al. | |
| 7,693,359 B2 | 4/2010 | Murphy et al. | |
| 2004/0207843 A1* | 10/2004 | Westbrook | 356/364 |
| 2005/0002017 A1* | 1/2005 | Haran | 356/73.1 |
| 2006/0153491 A1 | 7/2006 | Murphy et al. | |
| 2011/0001959 A1* | 1/2011 | Hasegawa | 356/73.1 |
| 2011/0110663 A1 | 5/2011 | Li et al. | |
| 2012/0176606 A1 | 7/2012 | Zadorozhny et al. | |
| 2014/0176937 A1* | 6/2014 | Liu et al. | 356/73.1 |

OTHER PUBLICATIONS

Hazan et al., "Buried Optical Fibre Pressure Sensor for Intrusion Detection," International Carnahan Conference on Security Technology, 1989, pp. 149-154.

Notice of Allowance dated Jan. 17, 2014, from U.S. Appl. No. 13/355,406, 8 pages.

Office Action dated Feb. 10, 2014, from Canadian Patent Application No. 2,802,633, 2 pages.

* cited by examiner

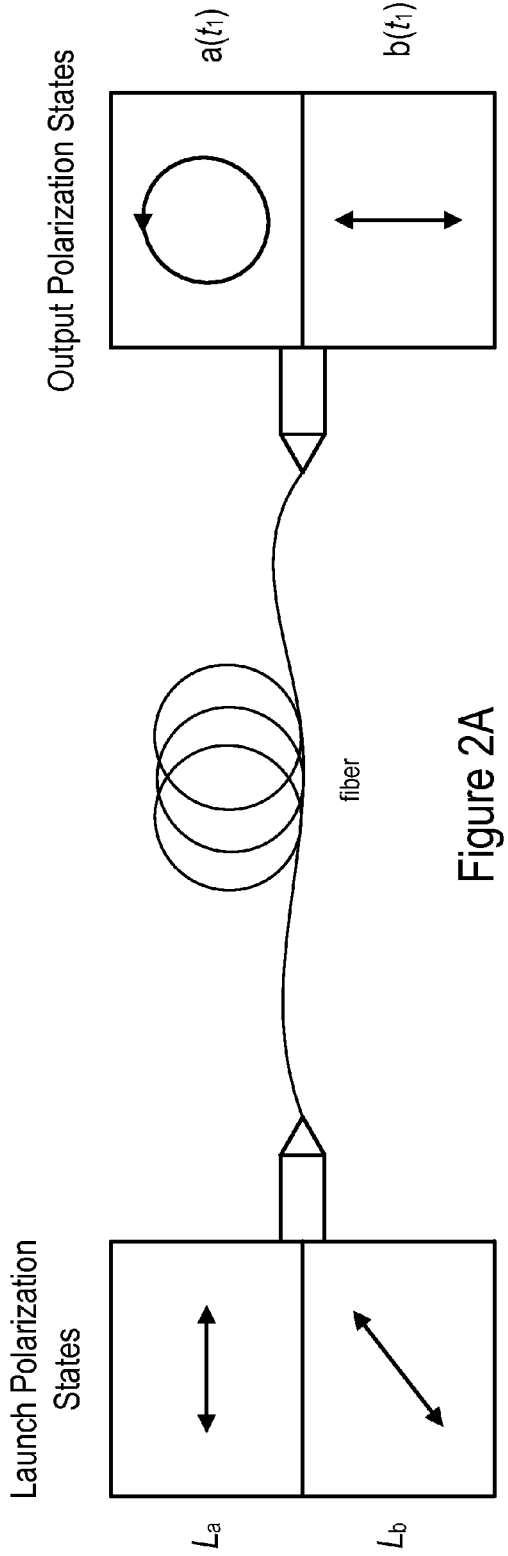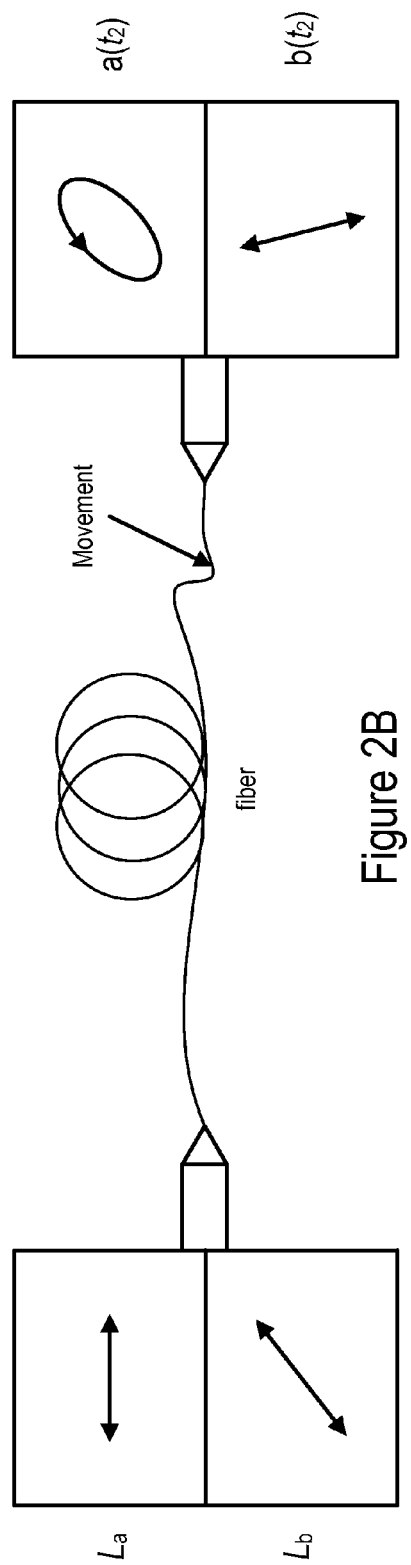

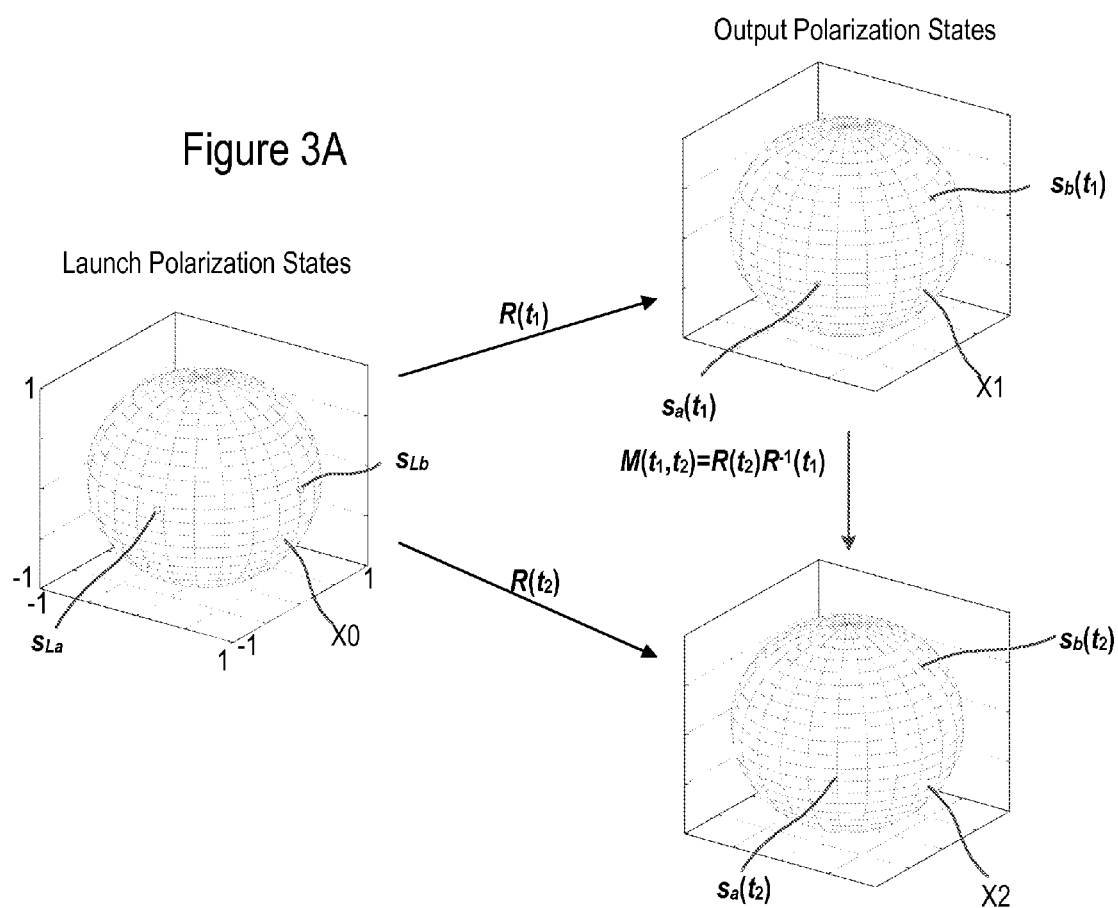
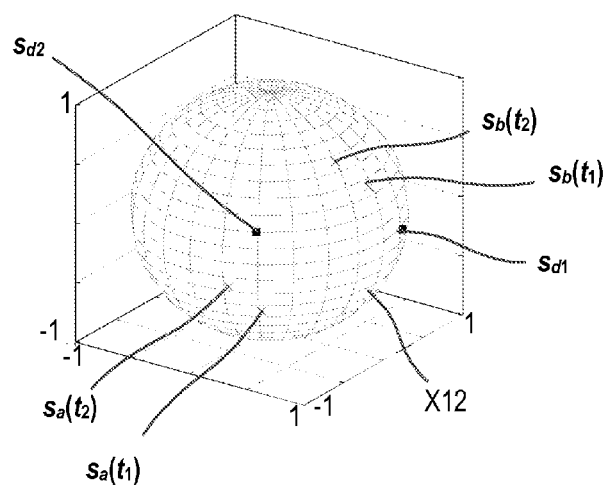
Figure 3A
Figure 3B

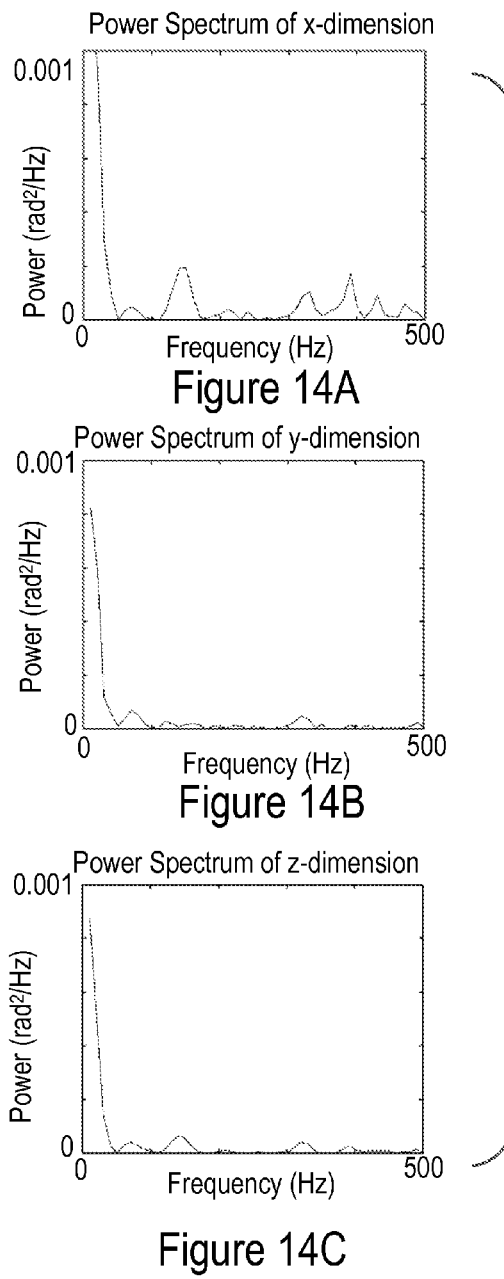
Figure 14A
Figure 14B
Figure 14C
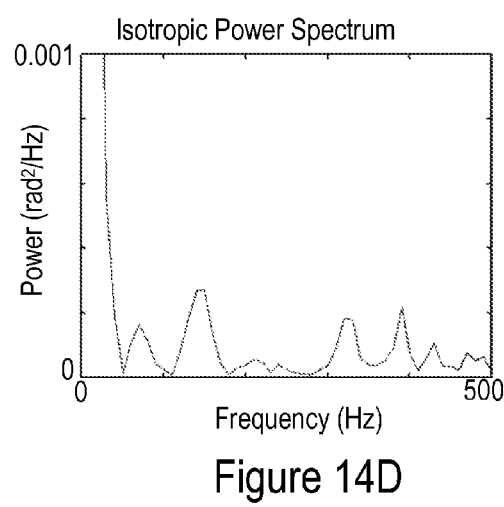
Figure 14D

MONITORING FOR DISTURBANCE OF OPTICAL FIBER

CROSS REFERENCE TO RELATED APPLICATION

This application is a continuation-in-part of U.S. patent application Ser. No. 13/355,406, filed Jan. 20, 2012, which is incorporated herein by reference.

TECHNICAL FIELD

This invention relates to systems and methods for monitoring for physical disturbance of an optical fiber, and is applicable to monitoring single-mode optical fiber using polarized light.

BACKGROUND

There are many applications for monitoring an optical fiber to detect physical disturbances, including monitoring for attempts to access data signals being transmitted over optical fiber, monitoring for attempts to intrude upon a zone protected by an optical fiber deployed around it, monitoring of vibration in machinery with which the optical fiber is associated, monitoring pipelines along which the fiber is distributed, and so on.

In the context of an optical fiber transmitting data, for example, it is well-known that an optical fiber can be tapped, and light extracted, without interrupting the transmission of the data signal along the fiber. One approach is to bend the fiber to such a degree that some light leaves it and can be diverted to a suitable receiver. Such a bend may introduce a loss of up to 1 dB of the transmitted signal, and optical data networks have intrusion detection systems capable of detecting this power loss and providing an intrusion alarm.

An alternative, lower-loss approach to tapping an optical fiber involves carefully grinding away the outer part of the fiber in order to permit evanescent-wave coupling to an adjacent tapping waveguide. The power loss resulting from this kind of tap might be as low as 0.04 to 0.004 dB. Such a low loss might be impossible to detect reliably by intrusion detection systems which use power measurement methods.

An alternative class of detection techniques is predicated upon the fact that physically disturbing an optical fiber will cause changes in the propagation characteristics of the optical fiber for polarized light. Typically, the physical disturbances will be asymmetric, so the refractive index for one state of polarization of the light will be altered differently from that for another state of polarization, causing relative phase shifts that will generally change the polarization state of a transmitted light beam that is composed of a mixture of these two polarizations. More particularly, in the various applications of the invention mentioned above, bending, compression, twisting or torqueing of the fiber may cause stress and strain that induce varying amounts of birefringence (linear or circular), resulting, for example, in a linear polarization state becoming elliptical or rotating. Such polarization changes can be detected as indications of a relevant disturbance of the optical fiber. Typically, sensors of this type are made using common telecommunications fiber, and using polarized light at a standard wavelength such as 1310 nm or 1550 nm for which inexpensive lasers are readily available, or at least between wavelengths such as 1260 nm and 1650 where the fiber operates in a single-mode manner and the attenuation is reasonably low.

Optical fibers carrying data usually are in a cable, sometimes with other fibers, and either of the above-described tapping procedures would entail physically disturbing the cable to such an extent that it is viable to design a monitoring system with enough sensitivity to detect an abnormal change in the polarization of light transmitted by the fiber to be tapped, or by a separate monitored fiber in the same cable, and initiate appropriate action, such as triggering an alarm, even before the intruder actually gained access to the fiber to be tapped.

Although, on the face of it, such a detection procedure might seem straightforward, in practice it is difficult to differentiate between normally-occurring disturbances and abnormal or "reportable" disturbances which should be reported because, for example, they result from a genuine intrusion attempt. The difficulty arises because effects in the fiber's environment can cause optical changes with similarities to some of those caused by intrusions. Such effects might include the effects of wind on a suspended cable, "stick-slip" phenomena combined with expansion and contraction during temperature changes, vibration from nearby equipment, or traffic or construction near a buried cable, and so on.

U.S. Pat. No. 7,173,690 (Haran) discloses a perimeter intrusion detection scheme comprising an optical fiber disposed around the perimeter of a building or other structure, for example by attaching it to a fence or burying it in the ground. Haran injects polarized light pulses into the optical fiber and detects changes in Rayleigh backscatter for different polarization states to determine occurrence of a disturbance and its location.

Haran uses a polarization optical time-domain reflectometer (POTDR) to capture a number (2 to 1000) of POTDR traces, digitally filters them and averages the digitally-filtered traces to form a "reference" trace which represents the normal or "no disturbance" condition. Thereafter, subsequent POTDR traces are acquired and compared with the reference trace. This process may take a typical POTDR several seconds (if not minutes) in order to achieve the desired signal to noise ratio (SNR) on a backscatter trace that is used for determining whether handling has occurred. As the length of the monitored fiber increases, a better SNR of the system is required, and therefore more averaging time. In view of the time taken to acquire enough samples for analysis, this method is mainly suitable for detecting slow changes, and is poorer for characterizing activity such as bumps or rattling that are associated with preparations to tap a fiber or other intrusions that have faster changes characterized by variations at moderate acoustic frequencies.

Other known techniques, such as those disclosed in U.S. Pat. Nos. 7,142,737, 7,206,469 and 7,693,359 and U.S. Patent Application Publication No. 2006/0153491, all by C. R. Murphy et al., and U.S. Pat. No. 5,061,847 (Hazan et al.) may sacrifice the position resolution of OTDR methods, but they require less signal-averaging time and can therefore capture acoustic-frequency disturbances with a good signal-to-noise ratio. This higher frequency response widens the range of criteria that can be used for distinguishing reportable disturbances from other changes. These techniques entail launching polarized light into an optical fiber, and detecting light emerging from the fiber through a polarizing filter or analyzer. The detection signal varies when the fiber is disturbed because a disturbance changes the transformation or rotation that the fiber enacts on the polarization of the light, so that, under the right conditions, the fraction of the light that passes through the analyzer will change.

The methods of Haran, of Murphy et al. and of Hazan et al. are subject to the phenomenon of "fading": the sensitivity of the detection signal to a disturbance in the fiber depends strongly on (i) how the polarization state of the light entering the disturbed region happens to align with the geometry of the disturbance, and (ii) how the change in the polarization of the light emerging from the fiber happens to align with the polarization analyzer. (Alignment of polarization states with polarization transforming devices and filters is different from ordinary alignment in physical space, but is a well-known concept.) The alignment is generally unpredictable depending on how different parts of the deployed fiber happen to be bent, twisted or stressed; and it will vary as environmental factors change (such as the temperature of the optical fiber cable). Thus, the sensitivity to a particular disturbance will be unpredictable and will vary randomly over time, between substantially zero and some maximum value. This unpredictable and variable sensitivity can make it difficult or impossible to set a threshold that the observed magnitude of a disturbance must exceed to make it reportable; specifically that is low enough to ensure reporting of substantially all disturbances that should be reported, yet high enough to reject changes that should not cause reporting.

Murphy et al. use detectors with two different polarization analyzers at the output of the fiber, chosen so that, when a polarization change occurs in the light that reaches the output, if it is aligned so that one detector sees little or no change at all, the other detector will usually see a more substantial change. The resulting sensitivity may vary, but at least it will go near or all the way to zero considerably less frequently for polarization changes that reach the fiber's output. That is because it requires a coincidence where both detectors are insensitive to change. However, the polarization of the light passing through the disturbed region may still be aligned more often with a physical disturbance in such a way that little or no polarization change is created, so it is still possible for the sensitivity to go all the way to zero, and close to zero fairly often.

Of the three references cited above (Haran, Murphy et al. and Hazan et al.), only Hazan et al. address the problem of fading in a concerted way. Related work is published in their paper "Buried optical fiber pressure sensor for intrusion detection," in Proceedings of the 1989 International Carnahan Conference on Security Technology, pp. 149 to 154, section 4.1.3. In this paper and their U.S. Pat. No. 5,061,847, Hazan et al. explain the causes of fading in detail, and disclose a way to mitigate the effects. Nevertheless, such mitigation is not entirely satisfactory.

Hazan et al. do better than Murphy et al. by using two launch states of polarization (as well as using two polarization filters for detection). Although Hazan does not state it this way, the two launch states should have Stokes vectors that are linearly independent. Thus, if the light due to one of the launch states, when it reaches the disturbed zone, is aligned with the disturbance in a way that produces no polarization change, the light from the other will necessarily be aligned in a way that does produce a change (and at least one of detectors at the output is likely to see a change). This use of two launch states means that a disturbance will always create a non-zero polarization change for at least one launch state, and thus makes a substantial improvement. Hazan et al. disclose several simple ways to combine multiple signals from different combinations of launch state and analyzer state (e.g. adding absolute values, or creating a logical "OR" of the alarms from two separate signals). However, although such ways of combining the signals (each of which has severe fading by itself) may reduce fading, significant fading can still occur, resulting in significant uncontrolled variations in sensitivity. (The aforementioned patent and paper by Hazan et al. do not clearly explore this limitation.) Consequently, this approach of Hazan et al. may not be entirely satisfactory, particularly in an application where it is not enough merely to reduce fading, but it is desirable to effectively eliminate it.

Hazan et al. and Murphy et al. specify rather explicitly what polarization states should be launched into the fiber, and what polarization filters or "analyzers" should be used at the detectors. Thus, Hazan et al. use a pair of linear polarization states at the input and another pair for polarization analysis at the output, with the second linear polarizer in each pair at 45 degrees to the first; or at least within the range of 30 to 60 degrees. In another case, they specify adding a circular polarizer. Murphy et al. teach the use of a pair of polarizers at detectors, one of which is linear and the second of which is either a circular polarizer or a linear polarizer at 90 degrees to the first. (In fact, it appears that this 90-degree angle does not increase the likelihood that every polarization change will cause a signal change, but merely provides redundant information: after correction for any sensitivity difference, the sum of the signals from two linear polarizers at 90 degrees is constant, proportional to the total power, so either one predicts the other.)

Such specific design constraints on the launch states and analyzer states can cause undesirable challenges in the engineering, specifying and manufacturing of a product. For example, some convenient ways to split beams to be divided between, and coupled to, different polarization analyzers, including coiled optical fibers used for coupling, may involve phase shifts that cause the combination of a linear polarizer with its coupling means to be tuned to some elliptical polarization state, and to have a relationship to a second polarizing filter that cannot be characterized so simply as a 45-degree angle between two linear polarizers. Similarly, analyzer means comprising a circular polarization filter or analyzer, when combined with its associated splitting or coupling means, may turn out to be tuned to a state that is very different from a circular polarization state. Almost all of the possible polarization states are elliptical to some degree, and tolerances on the departure from perfect linear or circular states would be a concern.

In summary, such previous polarization-based optical fiber disturbance monitoring systems experience significant fading, reducing their accuracy, consistency and reliability in assessing the magnitude of a disturbance, and hampering the ability to distinguish between reportable disturbances and disturbances that should not be reported. In alarm systems, this can either increase the frequency of false alarms or make it easier for an intruder to avoid detection. Such previous systems also place unnecessary restrictions on the polarization states launched into the fiber and/or on the filters or analyzers at the output end.

An object of the present invention is to at least mitigate deficiencies of such previous optical fiber disturbance monitoring methods and systems, or at least provide an alternative.

SUMMARY

Methods of monitoring an optical fiber comprise launching a probe light flux into the fiber, wherein the probe light flux includes a first portion and a second portion in respective launch polarization states that are characterized by linearly independent launch Stokes vectors. A received light flux associated with propagation of the probe light flux in the fiber is analyzed based on at least two analyzer polarization states that are characterized by Stokes vectors that are linearly independent. Detected signals associated with the analyzed received light are processed to determine a measure of change in the fiber over a period of time that is substantially invariant under a non-reflecting unitary transformation of either the launch polarization states or the analyzer polarization states. In some examples, a disturbance of the fiber is reported based on the determined measure of change, and the probe light flux portions associated with the each of the two linearly independent launch Stokes vectors are alternately or simultaneously launched into the fiber. In some embodiments, the probe light flux portions associated with each of the two linearly independent launch Stokes vectors are associated with different wavelengths. In further examples, processing the detected signals further comprises identifying detected signal portions associated with the first portion and the second portion of the probe light flux based on the different wavelengths. In some alternatives, the probe light flux portions associated with each of the two linearly independent launch Stokes vectors are associated with different modulations, and detected signals are identified based on the different modulations.

According to some examples, the probe light flux portions associated with each of the two linearly independent launch Stokes vectors are alternately launched into the fiber in a first time interval and alternately launched in a second time interval. The measure of change is determined based on detected signals associated with the first time interval and the second time interval. In typical examples, the measure of change can be derived from one or more vector representations of Poincaré sphere rotations corresponding to change or changes during the period of time.

In some particular embodiments, change information is determined over at least two sub-periods that are subsets of the time period and vector representations of Poincaré sphere rotations corresponding to the change information for the two or more sub-periods are determined. The measure is determined based in part on relative directional information or relative displacement information associated with the two or more vector representations. In some examples, a set of change information is accumulated representing a sequence of changes during the period of time. The measure corresponds to components of an isotropic power spectrum that can be represented as a sum of the three power spectra for three components of a corresponding sequence of vector representations of Poincaré sphere rotations. In additional examples, the probe light flux further comprises a third portion, wherein the first portion, the second portion, and the third portion are associated with respective linearly independent launch Stokes vectors. In other alternatives, the received light associated with propagation of the probe light flux in the fiber is analyzed based on at least three analyzer polarization states that are characterized by Stokes vectors that are linearly independent or based on at least four analyzer polarization states that are characterized by Stokes 4-vectors that are linearly independent.

Apparatus for monitoring an optical fiber include a probe light source coupled to launch a probe light flux into the optical fiber, wherein the probe light flux includes a first portion and a second portion in respective launch polarization states that are characterized by linearly independent launch Stokes vectors. A polarization analyzer is situated to receive a light flux associated with propagation of the probe light flux in the optical fiber and analyze the received light flux based on at least two analyzer polarization states that are characterized by Stokes vectors that are linearly independent. The polarization analyzer typically includes two or more detectors and two or more polarizers. A processor is configured to receive detected signals associated with the analyzed received light and determine a measure of change in the fiber over a period of time, wherein the measure of change is substantially invariant under a non-reflecting unitary transformation of either the launch polarization states or the analyzer polarization states. In some examples, the probe light source is configured to provide probe light flux portions associated with the each of the two linearly independent launch Stokes vectors and alternately launch the probe light flux portions into the fiber. In other examples, the probe light source is configured to simultaneously launch the probe light flux portions associated with the each of the linearly independent launch Stokes vectors. In representative embodiments, the probe light source is configured so that the probe light flux portions associated with each of the two linearly independent launch Stokes vectors are associated with different wavelengths or with different modulations. In further examples, the processor is configured to process the detected signals so as to identify detected signal portions associated with the first portion and the second portion of the probe light flux based on different wavelengths or different modulations.

In a representative example, the processor is configured to determine change information over at least two sub-periods that are subsets of the time period and determine vector representations of Poincaré sphere rotations corresponding to the change information for the two or more sub-periods. The measure is determined based on relative directional information or relative displacement information associated with the two or more vector representations. In a particular example, the polarization analyzer and the processor use four analyzer polarization states that are characterized by Stokes 4-vectors that are linearly independent. In additional representative examples, the probe light source is configured to produce a periodically varying synchronization light flux, and the processor is configured to establish detected signal portions associated with the first and second portions of the probe light flux based on the periodically varying synchronization light flux.

In other examples, according to a first aspect of the present invention, there is provided a method of monitoring a length of single-mode optical fiber (104) for physical disturbance along its length, comprising the steps of:

(i) at a first location (100), launching into the fiber polarized light having at least two different predetermined launch states of polarization ($L_a$, $L_b$) whose respective Stokes vectors ($s_{La}$, $s_{Lb}$) are linearly independent of each other;

(ii) at a second location (102) downstream from the first location, receiving the light from the fiber;

(iii) analyzing the received light using at least two different analyzer states of polarization that are characterized by respective Stokes vectors that are linearly-independent of each other:

(iv) detecting (126, 128, 130, 132) the analyzed light to provide corresponding electrical detection signals (d1, d2, d3, d4) and deriving therefrom corresponding digital detection signals (D1, D2, D3, D4);

(v) deriving from the digital detection signals (D1, D2, D3, D4) one or more representations ($[s_a(t_1), s_b(t_1)]$, $[s_a(t_2), s_b(t_2)]$; $M(t_1,t_2)$; $c(t_1,t_2)$; $C(t_1), C(t_2)$) of change or changes in the polarization coupling properties (R) of the fiber between at least two different times;

(vi) computing from said one or more representations at least one measure (4.14/4.15) of change in polarization coupling properties of the fiber, said at least one measure being substantially invariant under an arbitrary non-reflecting unitary transformation applied to all of the launch states of polarization or to all of the analyzer states of polarization; and (vii) determining with reference to preselected criteria of reportable physical disturbances whether or not said at least one measure indicates a reportable physical disturbance along said length of fiber.

According to a second aspect of the invention, there is provided a monitoring system for monitoring a length of single-mode optical fiber (104) for physical disturbance at a location or zone (L) along its length, comprising a launch unit (100) and a monitoring unit (102):

the launch unit (100) being adapted for launching into one end of the length of fiber polarized light at a first location light having at least two different predetermined launch states of polarization ($L_a$, $L_b$) whose respective Stokes vectors ($s_{La}$, $s_{Lb}$) are linearly independent of each other;

the monitoring unit (102) being adapted for receiving the light from a second end of the fiber and comprising:

analyzing means for analyzing the received light using at least two different analyzer states of polarization that are characterized by respective Stokes vectors that are linearly-independent of each other:

means (126, 128, 130, 132) for detecting the analyzed light and providing corresponding electrical detection signals (d1, d2, d3, d4);

analog-digital conversion means (142) for deriving from the electrical detection signals corresponding digital detection signals (D1, D2, D3, D4); and processing means operable for:

(i) deriving from the digital detection signals (D1, D2, D3, D4) one or more representations ($[s_a(t_1), s_b(t_1)]$, $[s_a(t_2), s_b(t_2)]$; $M(t_1,t_2)$; $c(t_1,t_2)$; $C(t_1)$, $C(t_2)$) of change or changes in the polarization coupling properties (R) of the fiber between at least two different times;

(ii) computing from said one or more representations at least one measure (4.14/4.15) of change in polarization coupling properties of the fiber, said at least one measure being substantially invariant under an arbitrary non-reflecting unitary transformation applied to all of the launch states of polarization or to all of the analyzer states of polarization; and (iii) determining with reference to preselected criteria of reportable physical disturbances whether or not said measure or measures indicate a reportable physical disturbance.

Preferably, in embodiments of either of the first and second aspects of the invention, said one or more representations comprise a plurality of said representations ($[s_a(t_1), s_b(t_1)]$; $[s_a(t_2), s_b(t_2)]$; $M(t_1,t_2)$; $c(t_1,t_2)$; $C(t_1)$, $C(t_2)$) over a predetermined period of time, each successive representation being stored and with preceding representations to provide change information comprising a sequence ($[s_a(t_1), s_b(t_1)]$, $[s_a(t_2), s_b(t_2)]$, $[s_a(t_3), s_b(t_3)]$, ...; $M(t_1,t_2)$, $M(t_2,t_3)$, ...; $c(t_1,t_2)$, $c(t_2,t_3)$, ...; $C(t_0)$, $C(t_1)$, $C(t_2)$, ...) of change information (4.23) for the fiber polarization coupling (R) over said predetermined period of time.

The criteria may take a variety of forms depending upon the particular application of the system. The criteria may be obtained following installation by accumulating data over a period of time, free of disturbances and/or with simulated disturbances, to establish such criteria as change-space distance thresholds, spectral power thresholds, numbers of times thresholds are exceeded in a specified time interval, and so on, that will distinguish between disturbances that should be reported and those that should not.

The measure(s) and associated criteria may be determined by time domain analysis and/or frequency domain analysis and/or geometric or dimensional properties of changes and/or other methods of analysis. A time-domain determination may be based on a measure of the magnitude of the change in the fiber over a prescribed time period. Either a time domain or a frequency domain determination may be based upon a measure of apparent movement or oscillation (of the fiber) in a manner that changes its polarization coupling properties in a one, two or three parameter manner over a prescribed time period, and this may provide information about the geometric complexity of a disturbance. A frequency-domain determination may be based upon using Fourier analysis to convert the change information over a prescribed time period into frequency domain information and obtaining a power spectrum characterizing the apparent disturbance, then computing measures of the power distribution in different frequency bands and comparing with values for these measures that are known to characterize reportable and/or unreportable disturbances.

Other aspects of this invention include the launch unit per se, launch method per se, the monitoring unit per se and the monitoring method per se, for use in the method or system of the first and second aspects.

More-specific features of the monitoring system and method may be as set out in the claims attached hereto and/or correspond to the foregoing method steps.

The foregoing and other objects, features, aspects and advantages of the present invention will become more apparent from the following detailed description, taken in conjunction with the accompanying drawings, of preferred embodiments of the invention, which are given by way of example only.

BRIEF DESCRIPTION OF THE DRAWINGS

In the drawings, identical or corresponding elements in the different Figures have similar reference numerals, in some cases with a prime or double prime denoting a difference.

FIGS. 2A and 2B illustrate how the length of optical fiber transforms two different launch states of polarization at different times;

FIGS. 3A and 3B illustrate similar transformations to those shown in FIGS. 2A and 2B but using the well-known Poincaré Sphere;

FIGS. 14A, 14B and 14C illustrate portions of the three power spectra for the three dimensions x, y and z, respectively, and for a short time interval, while FIG. 14D shows the isotropic power spectrum corresponding to the sum of the spectra of FIGS. 14A, 14B and 14C, respectively;

DETAILED DESCRIPTION

Figure 1:
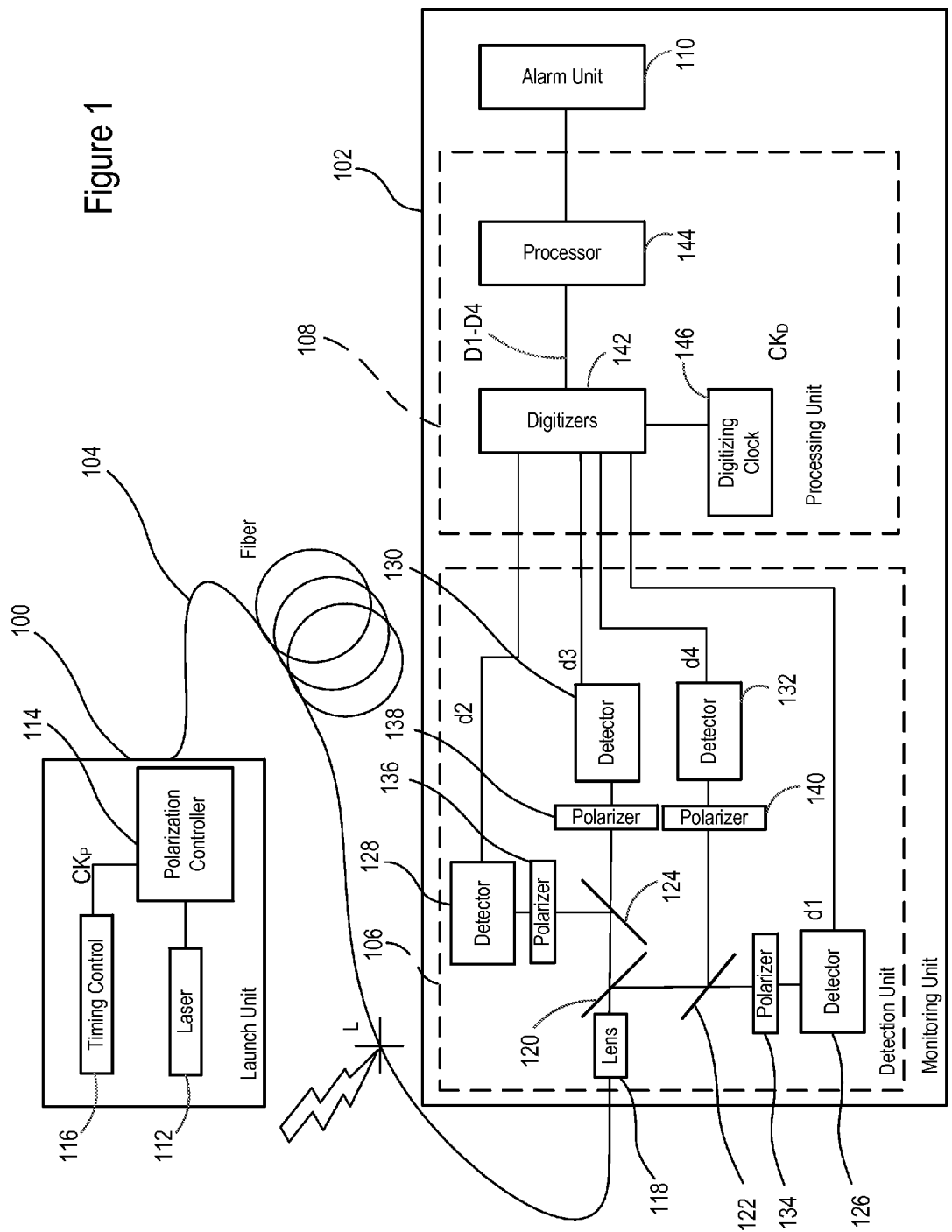
FIG. 1 is a simplified block schematic diagram of an optical fiber monitoring system embodying the invention and comprising a launch unit and a monitoring unit connected to respective ends of a length of optical fiber to be monitored.

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or apparatus are referred to as "lowest," "best," "minimum," or the like. It will be appreciated that such descriptions are intended to indicate that a selection among many used functional alternatives can be made, and such selections need not be better, smaller, or otherwise preferable to other selections.

Definitions

In this specification, the meanings of certain terms are as follows:

"Stokes 4-vector" refers to a four-component vector comprised of the four Stokes parameters ($S_0$, $S_1$, $S_2$, $S_3$); "Stokes 3-vector" and "Stokes vector" both refer to a vector comprised of three Stokes parameters ($S_1$, $S_2$, $S_3$), or to a unit vector with the same direction, as will be clear from the context.

"Stokes space" is a three-dimensional space in which each point corresponds to a Stokes 3-vector. The locus of all unit vectors in Stokes space is commonly referred to as the Poincaré sphere. It is common to graphically represent a pure polarization state, or the polarized part of a partially-polarized polarization state, by its unit Stokes vector, shown as a point on the surface of the Poincaré sphere.

A stationary light beam generally has a "state of polarization" or "polarization state" that can be fully polarized (a "pure" polarization state), partially polarized (equivalent to a pure state mixed with unpolarized light in some proportion), or unpolarized.

"Partially polarized light" (unlike unpolarized light) has a dominant polarization state (the pure component) that can be characterized by a Stokes vector, even though the Stokes 3-vector may not include the full information on the degree of polarization that a Stokes 4-vector does.

"Polarized" includes fully polarized and partially polarized, and excludes unpolarized, in application either to light or to an optical filter.

A "polarization filter" can be polarized or can be a "null" filter that has no effect on polarization of light passing through it, while a "polarized filter" or a "polarizing filter" does have an effect.

The term "polarizer" may designate any polarization filter, including a high-extinction device, an intermediate or low-extinction device, or a "null" filter that does not restrict the light passing through it on the basis of the light's polarization state.

An "analyzer" is the effective polarization filter between the output end of a fiber under test and a detector. It comprises any explicit polarizer or polarization-altering device that is placed in the path, plus any polarizing effects of minors, beamsplitters or other components. In some cases, depending on the context, "analyzer" may refer to a set of analyzers, possibly including associated detectors. For example, a subsystem comprising several single analyzers with different polarizers may be used to analyze the polarization state of light that comes into it, and may be called an analyzer.

The "extinction ratio" of a polarization filter or an analyzer is the ratio of the maximum fractional transmission for all pure polarization states of light to the minimum fractional transmission for all pure polarization states of light. The "extinction ratio" of a light beam is the ratio of its maximum fractional transmission for all perfect polarization filters (filters with infinite extinction ratio and no loss for an optimally aligned pure polarization state) to its minimum fractional transmission for all perfect polarization filters. An extinction ratio can range from 1 (unpolarized) to infinity (perfectly polarized).

The "degree of polarization" or "DOP" of a light beam is the ratio of the optical power in its polarized part to its total power. (A partly polarized light beam can generally be expressed as a superposition of a perfectly polarized beam and an unpolarized beam.) For an analyzer, the "degree of polarization" or "DOP" is the degree of polarization of a light beam having the same state of polarization as the associated "analyzer state of polarization" (as defined below). A degree of polarization can range from 0 (unpolarized) to 1 (perfectly polarized).

An "analyzer state of polarization" is associated with each analyzer, and may also be called the "polarization state" of the analyzer, or the "analyzer state". It is the state of polarization defined by the four components of the top row of the analyzer's Mueller matrix, taken as the four components of a Stokes 4-vector. This characteristic state of the analyzer has an extinction ratio that is the same as the extinction ratio of the analyzer. Whether this extinction ratio is high or low, so long as it is greater than 1, the analyzer can be characterized (at least partly) by a Stokes 3-vector, and it may be called a "polarized analyzer". If the extinction ratio is 1, the analyzer is similar to a null (unpolarized) polarization filter and it cannot be characterized by a Stokes 3-vector. Analyzer states are also sometimes called "detections states."

A "launch state of polarization" is the polarization state of a light beam that is launched into a fiber. It will generally be at least partially polarized in the examples presented here, and can therefore be characterized by a Stokes vector.

A "probe state" means either a lunch state or an analyzer state of polarization, and the "probe states" of a system that embodies the invention comprise the set of launch states and analyzer states. "Probe light" refers to light that is launched into the fiber for use in probing its light transmission properties.

The word "point", when used in reference to data, can apply flexibly to different kinds of data point, such as a raw data point comprising a set of the signal values/samples from several detectors as measured at a particular time, or an averaged data point, comprising a set of averages of the signals in raw data points measured over some time interval. The meaning will generally be clear from the context.

The word "block", when used in reference to data or data points, can apply flexibly to different kinds of block, such as a set of raw data points comprising signals from several detectors as measured at a number of sequential times, or a set of raw data points comprising the signals from a single detector at sequential times, or a set of partly reduced data points such as Stokes vectors. The meaning will generally be clear from the context.

A "unitary transformation" is a linear transformation that maps the space of polarization states onto itself, preserving the scalar product of the Stokes vectors for any two states, and preserving the degree of polarization. It is common to include, in this set, transformations that entail a reflection or inversion of the vector space that they operate on. However, for the purpose of this specification and the claims, reflections will be excluded from the definition of a "unitary transformation." Under such a transformation as herein defined, the Stokes vectors representing all polarized states undergo a rigid rotation on the surface of the Poincaré sphere by some angle, about some axis. The determinant of a matrix representing such a transformation is +1. (The determinant of the matrix would be −1 for a unitary transformation that entails a reflection.)

A "measure" of change of the fiber is the numerical and/or qualitative result of a computation done on a set of detection signals, possibly combined with other information such as calibration information that is indicative of some characteristic of a change in the fiber during the time spanned by the set of detection signals. A measure is "invariant" under a set of alterations to the probe states if the same computation, when applied to any of the resulting altered sets of detection signals, produces the same result as the unaltered signals. A measure is "substantially invariant" under such alterations if it is invariant to a good approximation, under a significant majority of conditions. (It should be noted that perfect invariance may not be achieved, as a result of normal inaccuracies in the instrumentation or its calibration or other effects. Also, for some hardware configurations there may be particular fiber conditions or "singular points" for which the sensitivity of the detection signals to fiber changes is very low or the noise in the processed results is high, meriting alternate processing that violates invariance only in the immediate vicinities of those conditions or points. Under such circumstances the system may still be described as "substantially invariant".)

Figure 5:
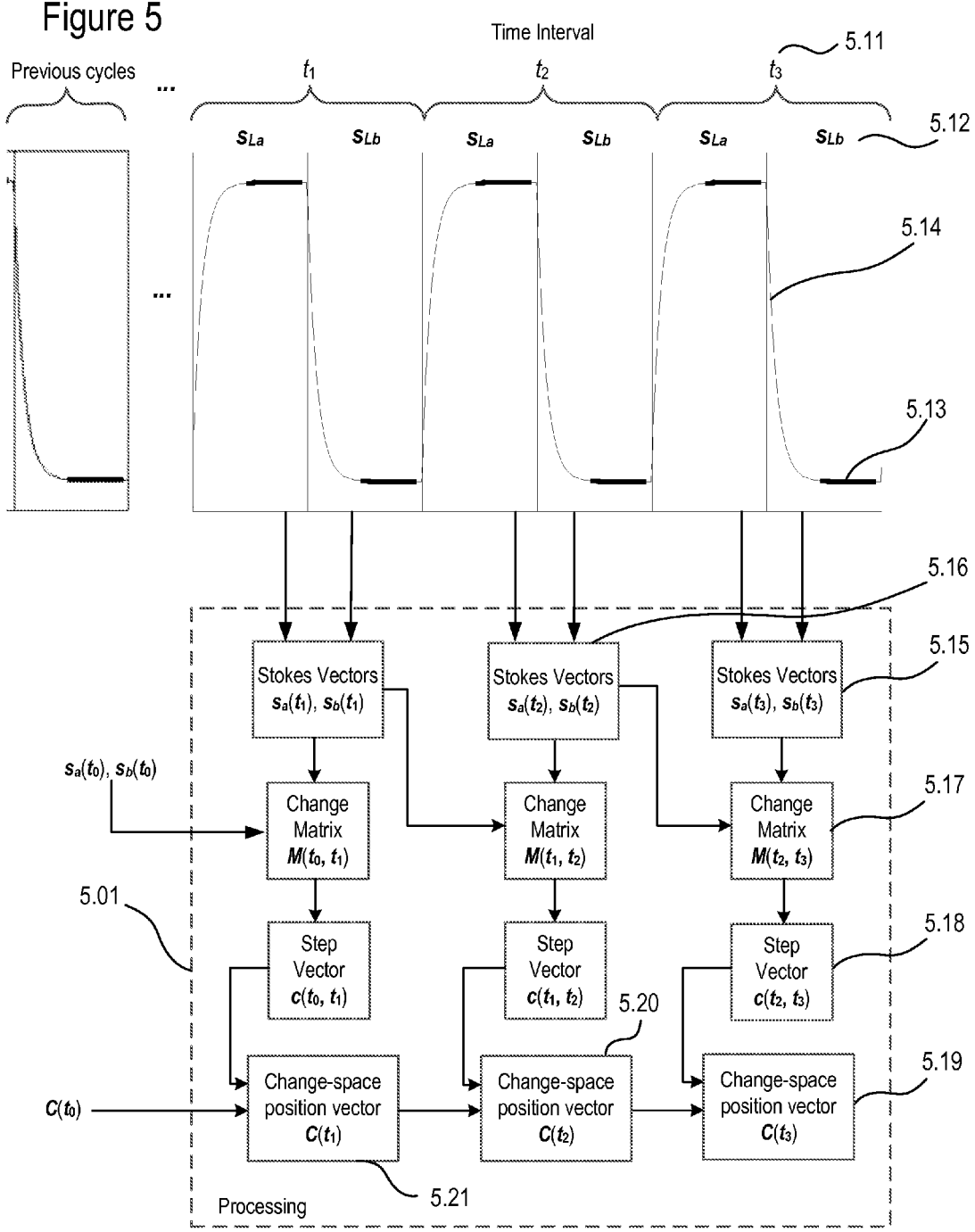
FIG. 5 illustrates the relationship between the launch polarization states and a corresponding detection signal over several time intervals, and depicts vectors and matrices used to derive from the detection signal a representation of fiber transformation changes.

In some examples, a launched light flux includes first and second portions associated with first and second linearly independent Stokes vectors that are alternately launched into a fiber under test, as described in FIG. 5. In other examples, these portions can be launched simultaneously and distinguished based on differing wavelengths or modulations. Two or more wavelengths or modulations can be used, and wavelength and/or modulation can be continuous, stepped at fixed or variable rates. Modulations can be configured so that a plurality of linearly independent Stokes vectors is used. Analyzer states can be time-multiplexed, and signals for one or more analyzer states can be evaluated sequentially and not simultaneously. Examples of these and other approaches are disclosed below.

A decision to report a disturbance will typically be based on a measure that is a Boolean value derived from other measures and/or change information, such as the comparison of a numeric measure of change to a threshold. The act of reporting may also entail providing information in the form of numerical or qualitative measures that meet the criterion of invariance under non-rotating unitary transformations of the launch or detection states, or other information that does not meet this criterion. While "measure of change" and "change information" are similar concepts (either might logically comprise the other), this specification will chiefly use "measure" in reference to information closely involved in reporting (such as 4.24 and 4.25 in FIG. 4), and "change information" in describing precursory information (such as 4.23 in FIG. 4).

"Change space" refers to a notional three-dimensional space which is used, in the specific embodiments presented below, as a particular way to describe changes in the transformation that an optical fiber does on the polarization state of the light that it carries. Changes in the transformation are conveniently represented by changes in position in change space. A "step vector" represents an incremental motion of the fiber's "position in change space" over a small time period, or, equivalently, the fiber's position in change space at some time is computed as a cumulative sum of successive step vectors. As will be explained in reference to FIGS. 5 and 10, a step vector can be computed as the product of an angle of rotation of the Poincaré sphere times a unit vector representing the axis of the rotation. This product can also be called a rotation vector. There are other ways to compute step vectors (such as a vector formed by the three common Euler angles that characterize a rotation) which are approximately equal to that in the example for small rotations (except possibly for a rotation, reflection, and/or scale factor) and may diverge for large rotations or in a cumulative sum, but for the purposes of the invention these distinctions are not essential. Similarly there are other ways to compute a sequence of positions in change space besides a cumulative sum of step vectors or incremental rotation vectors, such as a sequence of rotation vectors characterizing the total rotation of the Poincaré sphere since some starting time. Again, these different constructions are approximately equal (with the same exceptions) when the changes are small, and may diverge for large changes. Change space position sequences and step vector sequences are convenient examples of ways to represent change information in terms of rotation vectors that describe corresponding rotations of the Poincaré sphere or of Stokes vectors plotted on it, or, more tersely, "vector representations of Poincaré sphere rotations".

The "position in change space" of a fiber is not necessarily a "state function" or a function only of the configuration or state of the fiber. In other words, a cyclic disturbance of bending and twisting may return the fiber to its original physical configuration while its computed position in change space does not return.

Intrusion (disturbance) detection by embodiments of the present invention is predicated upon the fact that bending, twisting or compressing an optical fiber changes the polarization transformation properties of the fiber and so may result in concomitant changes in the state of polarization of light propagating along it. Monitoring systems embodying this invention, one specific example of which is illustrated in FIG. 1, comprise a launch unit 100 and a monitoring unit 102 interconnected by a length of optical fiber 104 to be monitored. In this example the monitoring unit 102 comprises a detection unit 106 and a processing unit 108. The launch unit launches into the length of optical fiber 104 light that has "launch states" of polarization that are significantly polarized and characterized by Stokes vectors that are linearly independent of each other. After the light has traversed the length of fiber, and been received by the monitoring unit, the detection unit creates signals using analyzers having at least two different "analyzer states of polarization" that are significantly polarized and are characterized by Stokes vectors that are linearly-independent of each other.

In contrast to the previously-known fiber movement/disturbance monitoring systems discussed hereinbefore, in monitoring systems embodying the present invention the detection signals are processed to create at least one measure that is substantially independent of non-reflecting unitary changes or transformations applied to either the set of launch states or the set of analyzer states used to probe the fiber. Such probe-state alterations will generally alter the detection signals, but, unlike previous systems, these alterations in the signals will not cause the final computed measures to change. Change-space analysis is helpful in devising and understanding measures that meet this beneficial criterion of invariance under a unitary transformation applied to either the launch states or analyzer states, because a change-space representation of changes already meets the criterion for the launch states; and a measure that is rotation-invariant in change space (such as a distance, or the angle or scalar product between two vectors) also meets the criterion for the analyzer states. Prototypes confirm that a rich set of such measures exists and is practical for sophisticated measurements and discrimination in decisions to report a disturbance. Associated concepts also help to understand rigorously what requirements are placed on the instrumentation by the invariance criterion, and why other monitoring systems either cannot meet the criterion because the instrumentation is insufficient, or do not because the computations applied to the detected signals are not sufficient.

In embodiments of this invention, the processing unit compares the measure(s) with criteria predetermined as indicative of a reportable disturbance and, on the basis of the comparison, may output an alarm or other signal via an alarm/output unit 110. Examples of useful measures will be described more fully later.

The way in which polarization transformation properties of the length of fiber change the polarization of the light propagating along it, over time, is illustrated in FIGS. 2A and 2B, for two launch states of polarization. Thus, in FIG. 2A, two "launch states" of the light launched into a fiber at a first time $t_1$ are represented as "$L_a$" and "$L_b$", respectively. In practice they may be launched separately at slightly different times close to the nominal time $t_1$, so that the two can be distinguished. Alternatively, other distinction methods can be used to allow simultaneous launching, such as using two closely-spaced wavelengths (in which case each detector in the detection unit might be replaced by two detectors, filtered to see different wavelengths) or modulating the light at two different frequencies, one for each launch state (in which case the detection unit might demodulate the signal on each detector). These diagrams indicate graphically the pattern of oscillation of the electric field, showing as examples horizontal linearly polarized light for launch state $L_a$ and 45-degree linearly polarized light for state $L_b$. The polarization transformation properties of the fiber, extant at that time $t_1$, change the polarization states of the light as it propagates along the fiber resulting in different output polarization states formed at the far end of the fiber 104, as represented by $a(t_1)$ and $b(t_1)$. In this example, the linear polarization state $L_a$ has been transformed into a circular polarization state and the 45-degree linear polarization state $L_b$ into a vertical linearly polarized state.

At the later time $t_2$, depicted in FIG. 2B, the launch states $L_a$ and $L_b$ are the same, but the fiber transformation is different because of some movement of the fiber 104 relative to its condition at time $t_1$. Consequently, the transformed output state $a(t_2)$ has changed a little to be somewhat elliptical, and the transformed output state $b(t_2)$ has remained linear but has rotated about the axis of the fiber.

This transforming of the launch states differently at the different times $t_1$ and $t_2$ is illustrated symbolically in FIG. 3 using Poincaré spheres X0, X1 and X2, and matrices representing the polarization transformation properties of the fiber at times $t_1$ and $t_2$ are indicated by symbols $R(t_1)$ and $R(t_2)$, respectively. The launch states are represented by their associated Stokes vectors $s_{La}$ and $s_{Lb}$, and these vectors are shown graphically on the first Poincaré sphere X0. The second Poincaré sphere X1 shows the Stokes vectors $s_a(t_1)$ and $s_b(t_1)$ representing the output states of polarization of the light as received at time $t_1$, after transformation by $R(t_1)$; and the third Poincaré sphere X2 shows the Stokes vectors $s_a(t_2)$ and $s_b(t_2)$ representing the output states of polarization of the light as received at time $t_2$ after transformation by $R(t_2)$. The relationships are simple matrix multiplication of a column vector, vis. $s_a(t_1)=R(t_1)\,s_{La}$ at time $t_1$ and $s_a(t_2)=R(t_2)\,s_{La}$ at time $t_2$.

A comparison of the Poincaré sphere X1 with the Poincaré sphere X2 shows that changes in the fiber's polarization transformation properties which occurred between times $t_1$ and $t_2$ caused the Stokes vectors of the two output states to move on the Poincaré sphere. The change in the fiber's polarization transformation properties, between the two times $t_1$ and $t_2$, i.e., between spheres X1 and X2 in FIG. 3, is expressed as a change matrix $M(t_1,t_2)$, where $M(t_1,t_2)=R(t_2)R^{-1}(t_1)$. This way of constructing it simply transforms the $t_1$ output states backwards to the launch states and then forwards to the $t_2$ output states, and is equivalent to $R(t_2)=M(t_1,t_2)\,R(t_1)$.

Although this relationship is a good way to define and explain the change matrix, in practice the processing unit will not actually compute it this way from the data because it will not actually determine the R matrix that describes the fiber's polarization transformation.

Change matrix $M(t_1,t_2)$ is a rotation matrix that describes the rotation of a sphere between times $t_1$ and $t_2$, and the rotation of a sphere is defined uniquely by the motion of two points on its surface. (See *Rotations, Quaternions and Double Groups* by Simon Altman, Dover, 2005, pages 22-23. The points must not share a common axis through the center of the sphere, i.e. the vectors to these points from the center of the sphere must be linearly independent.) Therefore, it is sufficient to determine the Stokes vectors $s_a$, and $s_b$ for the two output states at each of the two different times $t_1$ and $t_2$ in order to determine the change matrix $M(t_1, t_2)$ from measurements of the detection signals; with no reference to the launch states per se or the matrix R for the fiber's polarization transformation.

Preferred embodiments of the present invention, in effect, determine a series of such change matrices, or similar information in some different form, over a predetermined period of time and use them to derive one or more measures dependent upon movement of the fiber during that time period. More particularly, they convert a sequence of measured change matrices into "Change-Space Position Information" conveniently represented as a sequence of vectors representing successive positions in a notional three-dimensional space called "change space"; and they subsequently reduce the change-space information to one or more practical measures or metrics suitable for evaluation to determine whether or not a reportable disturbance has occurred. One measure may be the distance or length of displacement in change space over a particular time (approximately equivalent to an angle of rotation on the Poincaré sphere); another might be a power spectrum (function of frequency) that can be reduced further by integration over specific regions of frequency to create simpler measures that are useful for reporting. A category of useful reduced measures relates to the dimensional and geometric properties of a motion pattern or vibration in change space (e.g. one-, two- or three-dimensional parameter changes), which are related to the nature of the disturbance that causes it.

As a result of their substantial independence of the launch and analyzer states, these measures are substantially independent of static twisting, bending or stressing of sections of the fiber that are removed from the zone of the disturbance. In other words, they are substantially free of fading.

Figure 4:
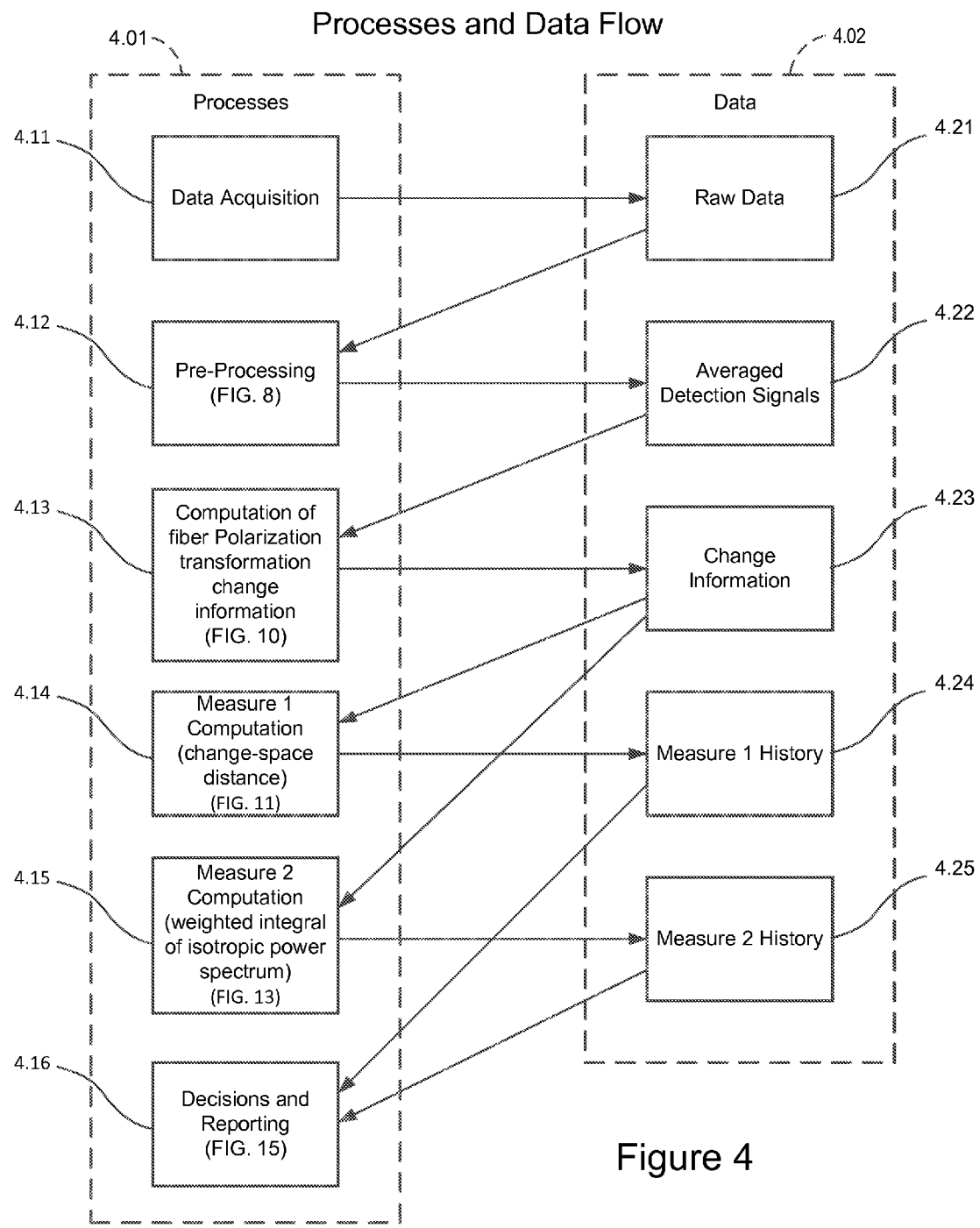
FIG. 4 illustrates signal processing and data flow in the processing unit of FIG. 1.

An example of signal processing useful for deriving the measure(s) from the output states, and then evaluating it/them to make a decision, is illustrated in FIG. 4 in terms of process steps and data flow. Part of this is depicted schematically and mathematically in FIG. 5 in terms of computation of vectors and matrices for several cycles of the polarization modulation.

FIG. 5 shows three cycles of one of the detection signals identified by their medial times $t_1$, $t_2$ and $t_3$ The various operations shown in box 5.01 of FIG. 5 represent mathematically the processing performed in process 4.13 of FIG. 4 to derive the change information from the detection signal as a sequence of change space vectors.

Thus, in FIG. 4, the major signal-processing steps 4.01 that are performed by the processor 144, to derive the change-space position information represented by vectors $C(t_1)$, $C(t_2)$ and $C(t_3)$ in FIG. 5, are shown as Data Acquisition process (4.11), Pre-processing process (4.12) and Computation of Fiber Polarization Transformation Change Information process (4.13), the corresponding data sets 4.02 that are inputs and outputs for these processes being "raw" Data (4.21), Averaged Detection Signals (4.22) and Change Information (4.23), with arrows indicating the flow of data into and out of the processes.

FIG. 5 does not necessarily represent the grouping of operations into subroutines or loops. It shows both the names and the symbols for the mathematical objects that are used as intermediates in this particular description of embodiments of the invention, for operating on detection signals to compute the measure(s) of fiber transformation changes. The processor uses the Change Information 4.23 in Measure-1 computation process 4.14 and Measure-2 computation process 4.15 to compute these two measures, and it accumulates them over time to produce Measure-1 History data 4.24 and Measure-2 History data 4.25 which it uses in Decisions and Reporting process 4.16.

The Decisions and Reporting process 4.16 is shown as a single process but it may be used with the Measure-1 History and Measure-2 History independently to make a separate decision for each, though the decisions need not be reported separately.

Except where noted below, in the specific embodiments described herein, the signal processor 144 carries out the data processing steps independently and asynchronously (e.g. in different threads); and the output data sequence created by each process step is stored in a corresponding circular buffer with enough capacity to ensure that subsequent process steps that use the data have access to what they need. (Such buffering is known to those skilled in the art and will not be discussed in detail here.)

In data acquisition process 4.11, the processor 144 acquires "raw" digital data from the A-to-D converter unit 142 for the four detection signals D1-D4 (FIG. 1) and stores it in a buffer as Raw Data 4.21. (Data acquisition is a process generally known to those skilled in the art so process 4.11 will not be described in detail here.)

Figure 6:
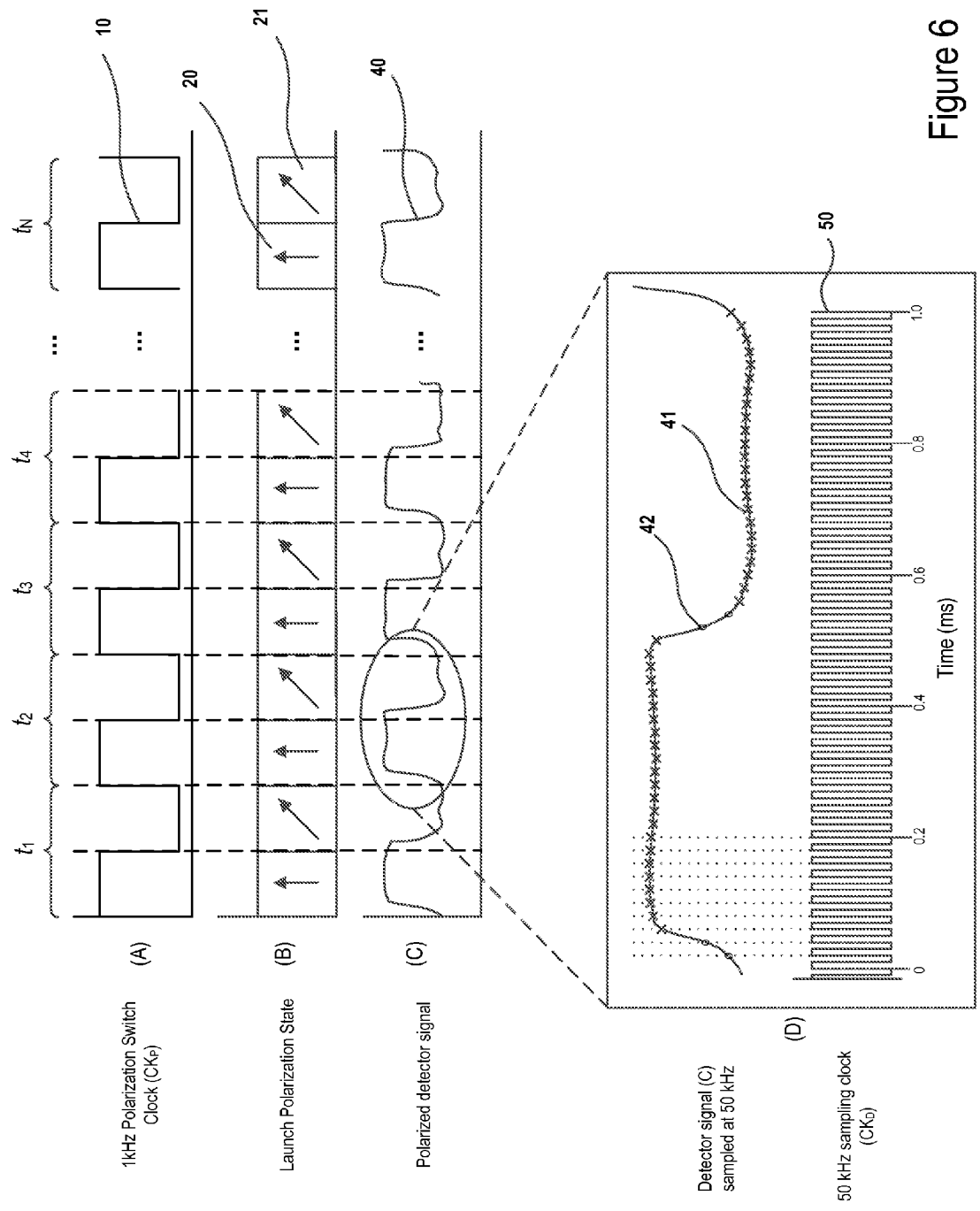
FIG. 6 illustrates timing and state diagrams for signals in the launch unit and the monitoring unit of FIG. 1.
Figure 7:
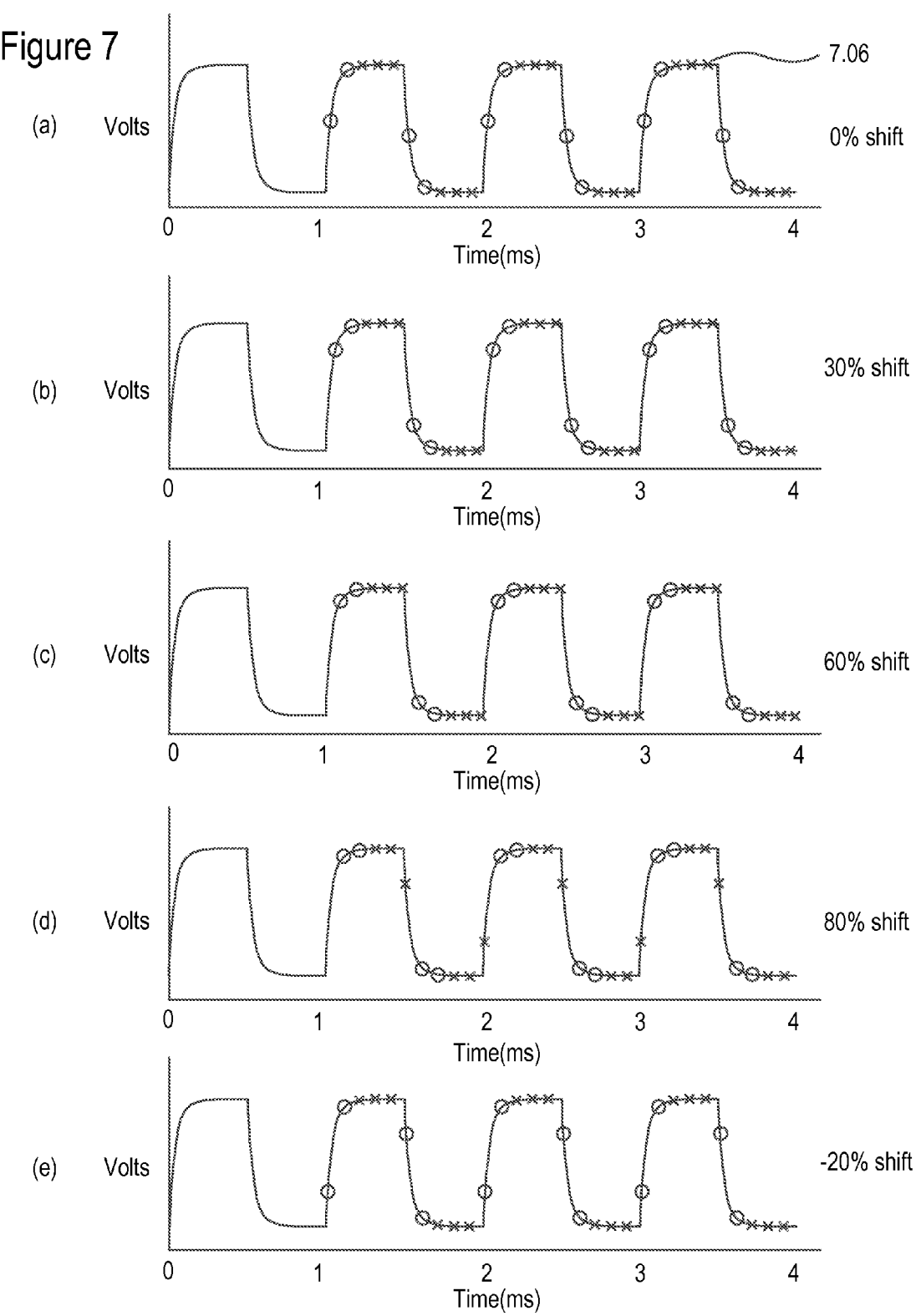
FIG. 7 illustrates correction of phase offset of detection signals for registration purposes.

In process 4.12, the processor examines a block of "raw" data 4.21 from the detection signals, and first performs phase offset measurement and correction or registration, as will be described in more detail later with reference to FIGS. 6-8. (An exception being "synchronized" embodiments in which the launch unit supplies a synchronizing signal to the monitoring unit.) This phase correction and registration process ensures that each detection signal will be correctly sampled and that average values for the signals will be derived accurately from the samples in the relatively unchanging medial portion 5.13 (shown bold in FIG. 5) of each half-cycle of the detection signal, illustrated as trace 5.14 in FIG. 5.

The correspondence between the alternating detection signal and the alternating launch states of polarization (see FIGS. 2A, 2B and 3) is indicated in FIG. 5 by showing above each half-cycle of the detection signal the respective one of the Stokes vectors $s_{La}$ and $s_{Lb}$. (as at 5.12). As will be described in more detail later with reference to FIGS. 8 and 9, the processor averages the sample values represented by the highlighted section 5.13 to reduce noise effects and create a single sample value for each half-cycle. These sample values form the averaged detection signals data 4.22 used by processor in process 4.13 to compute the change information data 4.23.

The sequence of averaged detection signals 4.22 stored following process 4.12 contains sufficient information on successive changes in the fiber transformation so that processes 4.13 (see also 5.01) and 4.14 or 4.15 can "purify" it from dependence on the launch states and analyzer states of polarization. The first step is to reduce it to a sequence of pairs of output Stokes vectors that are independent of the analyzer states of polarization, except for the choice of basis for the vector space. After that, the information will be further reduced to a sequence of "change matrices" that are also independent of the launch states of polarization. These will be converted to another form of change information sequence 4.23, and from this change information sequence subsequent measures of the fiber disturbance will be computed that are also independent of the vector-space basis and are therefore fully independent of all probe states.

Thus, referring also to FIG. 5 and using the cycle at time $t_3$ as an example, the two averaged detection signal values from the cycle $t_3$, one in each half cycle, are used to determine the pair of Stokes vectors $s_a(t_3)$ and $s_b(t_3)$ (5.15). This pair of Stokes vectors $s_a(t_3)$ and $s_b(t_3)$ is combined with the pair $s_a(t_2)$ and $s_b(t_2)$ from the preceding cycle $t_2$ to compute the 3×3 change matrix $M(t_2,t_3)$ (5.17) representing the change in the fiber polarization transformation between the two cycles. This 3×3 change matrix $M(t_2,t_3)$ is converted (5.18) directly into a 3-element "step" vector representation $c(t_2,t_3)$. Step vector $c(t_2,t_3)$ is added to the accumulated sum $C(t_2)$ of the previous step vector(s) to form sum vector $C(t_3)$, representing the current position in notional "change space".

The pairs of output Stokes vectors $s_a(t)$ and $s_b(t)$ are independent of the analyzer states used to analyze the polarization of the detection signal, except in the sense that the numerical values of their components depend on the basis used to represent the vectors, and the basis will usually be chosen in relation to properties of some of the analyzer states. But they are not independent of the launch states of polarization $L_a$ and $L_b$. (For example, changing the launch state $L_a$ would change the detection signals and cause the computed output Stokes vector $s_a(t)$ to change.) However, when the two pairs of Stokes vectors for two successive polarization cycles are reduced to a "change matrix" (5.17) that represents the change in the fiber polarization transformation, the change matrix is substantially independent of the launch states of polarization. Hence, the change matrices $M(t_1,t_2)$, $M(t_2,t_3)$ and so on, the step vectors $c(t_1,t_2)$, $c(t_2,t_3)$ and so on, and the change-space position vectors $C(t_1)$, $C(t_2)$, $C(t_3)$, and so on, are all dependent, in effect, only on changes in the polarization transformation properties of the fiber over the time concerned, except that the basis used to express these vector or matrix objects may depend on the detection states. Any property or measure that is computed from any one of them and that is basis-independent (or rotation and reflection independent) will thus be substantially independent of both the launch and detection states, without even a basis dependence. Such measures include, for example, the length of a vector, the angle between two vectors, the magnitude of the angle of rotation indicated by a rotation matrix, or a measure derived from the "isotropic power spectrum" described further below. These are measures of changes in the fiber alone, and will not be subject to fading.

Some disclosed measures are generally independent of the probe states, and dependent only on changes in the fiber. However, this criterion of complete probe-state independence would be more restrictive than appropriate, and as a result it would exclude some measures that are properly encompassed by the disclosure. For example, a new measure can be constructed by combining a probe-state-independent measure with some property of the probe states that is constant (for example, a new measure can be made by multiplication of a probe-state-independent measure by the angle between the Stokes vectors for two detection states.) Such a new measure is then not strictly independent of the probe states; but it will still exploit the disclosed methods to achieve the fading-free advantage. (It is possible that such a new measure could be computed from detector-signal data in a different way that obscures a simple relationship that it might have to a probe-state-independent measure.)

Some embodiments can be described by a less restrictive criterion, requiring that a measure should be invariant under a particular limited class of change applied to the probe states, instead of under all changes to them: the measure is invariant under an arbitrary unitary transformation applied to the launch states or to the analyzer states. In more detail, this means that if we insert, between the Launch Unit 100 and the Fiber 104, a physical device that performs a unitary transformation on the light that it transmits, and we apply exactly the same computation procedure to the altered detection signals, the procedure is such that the computed measure will be the same. Similarly, if we insert, between the fiber 104 and the Monitoring Unit 102, a physical device that performs a unitary transformation, and we apply exactly the same computation procedure to the altered detection signals, the procedure is such that the computed measure will be the same. (This device would perform a unitary transformation on the analyzer states, as they are seen from the output of the fiber. This is true even though it might seem more natural to view it as performing the inverse of that transformation on the light emerging from the fiber. Such unitary devices are hypothetical and do not need to be actually applied physically, as the invariance of a computation procedure can be verified mathematically.) This less restrictive criterion is sufficient to ensure substantial freedom from fading, and is substantially met by all of the embodiments described in this specification, at least under most fiber conditions except for the vicinity of some "singular points" that exist for certain hardware configurations.

Notwithstanding the proper less restrictive criterion described above or other criteria, the preferred embodiments described here all include measures that meet not only that criterion but also the more restrictive criterion of probe-state independence. Full probe-state independence is straightforward to achieve and preferred in many applications because it ensures that, for a given fiber type, the magnitudes of the computed measures will be the same for two different systems that have different probe states, different detector sensitivities and/or different optical powers. (Less restricted examples, also described herein, are easy to devise, as was done above.)

For convenience, derivations for all of the examples of measures that follow are made from a change-space description of the change information. All of the examples are independent of rotations or reflections in change space, and this fact implies that they are unchanged under unitary transformations of the analyzer states, since the bases for change space and for Stokes space at the detection unit are related. (Also, the mere fact that they are derived from change space implies that they are independent of the launch states, since, as previously noted, the change matrices and subsequently-derived change-space information are independent of the launch states.) However, the change-space formalism is not necessarily the only way to describe or compute these measures or their equivalents.

It should be noted that, when each new change-space position vector is computed, its predecessor is not discarded, i.e., $C(t_1)$, $C(t_2)$, $C(t_3)$ and so on are saved in a buffer. Hence, a sequence of change-space position vectors is saved, representing a path through change space. The change-space position vector $C(t_3)$ represents the change-space position at time $t_3$ (5.11). The cumulative change-space position data represented by sum vectors $C(t_1)$, $C(t_2)$, $C(t_3)$, and so on, stored in the buffer as Change Information 4.23, will be used by the processor in both of steps 4.14 and 4.15 to compute Measure-1 and Measure-2, respectively, for each evaluation by Decisions and Reporting process 4.16 to determine whether or not a reportable disturbance has occurred.

4.14 Compute Measure-1; Change-Space Distance

The change information 4.23 will be accumulated on a continuous basis, earlier change information that is no longer needed being discarded, as appropriate, by the circular buffer. To compute Measure-1, in computation step 4.14, the processor 144 takes current change information 4.23 and previous change information that was computed a time period $t_D$ earlier ($t_D$ might typically be ½ to 10 seconds) and reduces the current and previous change information to a measure of the distance moved in notional change space over time period $t_D$. For moderately small changes of the fiber, this distance is approximately equivalent to the magnitude of the rotation angle (in radians) on the Poincaré sphere corresponding to the change matrix over that time period $t_D$.

After a short delay that is a fraction of the time period $t_D$, the processor 144 obtains two more samples of the change information, preferably, but not necessarily separated by the same time period $t_D$, and computes from them another distance moved. The processor repeats this process, storing a sequence or history of this distance moved over a predetermined period of time, as the Measure-1 History 4.24. Periodically, the processor evaluates this Measure-1 History data with respect to preset criteria deemed characteristic of an intrusion attempt in order to decide whether a reportable disturbance has occurred (see process 4.16).

4.15 Computation of Measure-2; Power Spectra

Figure 13:
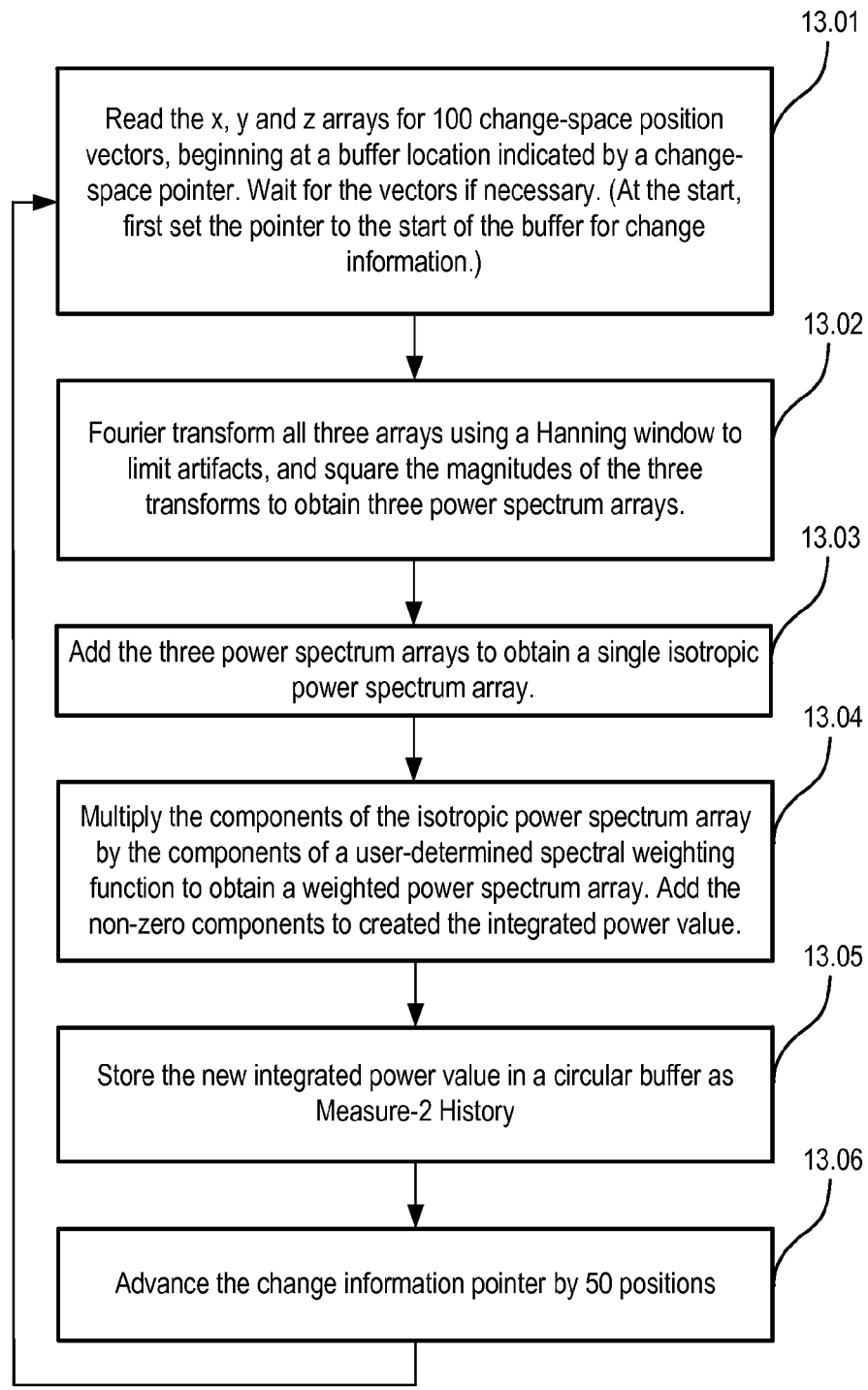
FIG. 13 is a flowchart depicting computation of power spectra for three dimensions x, y and z, respectively, from the Change Information of FIG. 10, combining them to form an isotropic power spectrum, and computation of an integrated power value.

To compute Measure-2, in computation process 4.15, the processor 144 takes a series of blocks of recent Change Information data 4.23, each block encompassing a relatively large number (such as 100) of time intervals or cycles of the polarization modulation such as indicated by 5.11 (FIG. 5), and uses Fourier analysis to reduce each block to an "isotropic power spectrum array" (as explained in more detail hereinafter with reference to FIG. 13) that characterizes the changes in the fiber polarization transformation over the duration of the block.

The processor may then weight and add the components of each of the isotropic power spectrum arrays to obtain a series of weighted integrated power values, and store these values sequentially as the Measure-2 History 4.25. The processor evaluates this history 4.25 in Decisions and Reporting process 4.16 with reference to preselected spectral power parameters, e.g. thresholds or other spectral attributes, deemed characteristic of an intrusion in order to decide whether a reportable disturbance has occurred.

The Measure-1 process 4.14 can of course be applied concurrently with multiple different values for the time period $t_D$ to create multiple simultaneous measures that may have different corresponding thresholds for reporting decisions; and similarly the Measure-2 process 4.15 can be applied concurrently with multiple different parameter sets for computing multiple integrated power measures.

4.16 Decisions and Reporting

In decisions and reporting process 4.16, the processor 144 evaluates the recent histories 4.24 and 4.25 of measures 1 and 2, respectively, against criteria (for example thresholds or parameters) that have been preset, either by the manufacturer, the installer, or the user, according to the application for the system, to determine whether a reportable disturbance has occurred. In this specific exemplary embodiment, the process 4.16 makes the decisions for the two different measures independently with no regard for correlations between the two. In fact, the code for these two independent decisions might conveniently be incorporated into the corresponding processes 4.14 or 4.15 that compute that measures.

Other similar embodiments might use one or the other of Measure-1 and Measure-2 alone, or use more complex decisions and reporting processes, including correlations between the two different measures. For example, reporting might be done if either measure exceeds an associated "high" threshold, and also if both measures exceed specified "low" thresholds within a 10-second period.

It will be appreciated that, as is common for security systems and other similar applications, the actual values used for thresholds, time intervals, and so on will vary widely with the application, the particular installation, and the preferences of the user; and the processor may permit the user to set the parameters to whatever values, and by whatever procedure, that he wishes to use.

To this end, the processor 144 will have means (not explicitly shown in the diagrams) by which the user can communicate with it in order to set the values of parameters that it uses for processing. Sets of thresholds characterizing reportable disturbance characteristics might be preset by the manufacturer based, for example, upon empirical data, and a particular set suitable for a particular situation selected by the user. The preset thresholds etc. might be updated by the user, or automatically by the processing unit, based upon actual usage over a period of time with and without real reportable disturbances occurring. Typical manners in which such thresholds are determined and used are known to those skilled in this art and need not be described in more detail here.

The particular ways of producing and representing the fiber transformation change information in the foregoing description are chosen for their convenient intuitive and physical meanings in illustrating the principles of the invention. Other ways of deriving change information may be employed, using different hardware and/or software configurations, for example.

Several different embodiments will now be described, by way of example only, to show how the above-described process can be carried out with various combinations of launch states and analyzer states. The different embodiments will generally require different computations for determining the Stokes vectors of the output states and the changes in the fiber polarization transformation, and may have different tradeoffs between cost and sensitivity or noise. Their operations will be described up to the point of determining the Stokes vectors that characterize the output states, which are used for determining the Change Information 4.23. In general, the Change Information will be similar in form for all of these embodiments. Thereafter, the computations of Measure-1 and Measure-2 and their Histories, and the Decisions and Reporting processes, may continue as described hereinbefore with reference to Steps 4.14, 4.15 and 4.16 of FIG. 4, subject to modifications to be described afterwards.

As will be described, the four detectors of the first embodiment allow an output Stokes vector to be determined from a simple weighted sum of the four detection signals, provided the four analyzer states meet certain simple criteria. Other embodiments illustrate how to implement the invention with fewer analyzer states, generally meaning fewer components and lower cost. In these cases, the Stokes vectors are not expressed as simple weighted sums, but there is still enough information to determine them well enough. Formulae for data reduction with fewer detectors may involve square roots that are double-valued functions, however, and they may have singular conditions where they are susceptible to noise. These conditions can be handled by continuity requirements on the Stokes-vector motions, recognition and mitigation methods for noise sensitive conditions, and use of additional information, such as stability of the scalar product or angle between the two Stokes vectors, or constancy of the optical power.

Embodiment 1: Two Launch States; Four Analyzer States

A first embodiment, a monitoring system that uses two launch states and four analyzer states, will be described by way of example with reference to FIGS. 1 to 15. As shown in FIG. 1, a launch unit 100 and a monitoring unit 102 are coupled to first and second ends, respectively, of a length of optical fiber 104 which might be from a few meters to more than 40 km long. In the following description, the first end and second end may also be described as proximal and distal, respectively, with respect to the launch unit 100. The first/proximal end will be deemed to be "upstream" and the second/distal end "downstream" even though there may be counter-propagating reflected light and regardless of whether the two ends are physically remote from each other, for example as ends of an optical cable in an optical communications network, or physically co-located, for example where the length of optical fiber comprises two individual fibers "looped back" in the same cable or where the fiber is deployed in a loop around a zone being protected against intrusion, such as an electric power substation. It should also be appreciated that the "ends" may be ends of a portion of a longer fiber, either or both of the launch unit 100 and the monitoring unit 102 being connected to it by, for example, a fiber tap or taps.

The launch unit 100 comprises a linearly-polarized laser source 112, a polarization controller 114 and a timing control unit 116. The light from the laser source 112 is passed through the polarization controller 114 which, under the control of a 1 kHz timing or clock signal $CK_P$ (see trace (A) of FIG. 6) from timing control unit 116, modulates the polarization of the light to produce two different polarization states ("launch states") which alternate with a 50% duty cycle, each cycle having a 1 millisecond period, as shown in trace (B) of FIG. 6. The polarization controller 114 comprises a device which accepts linearly-polarized input light and switches its output between two linearly-polarized states at 45 degrees to each other (which is a 90 degree rotation in a Poincaré-sphere or Stokes-vector representation of the state). A suitable such device is marketed by General Photonics Corporation under the trademark PolaSwitch™.

At the monitoring unit 102, the light that was launched into the proximal end of fiber 104 and has propagated along the length of fiber 104 (past a disturbance location or zone) is received at the distal end by a detection unit 106 and converted to corresponding detection signals which are processed by the processing unit 108 to identify changes consistent with a physical disturbance of the fiber 104 indicative of an intrusion attempt somewhere along its length. Such an intrusion attempt might involve movement of the fiber 104 by someone preparing to tap it and extract data signals propagating therealong, e.g., where the fiber is used for communications purposes, or by an intruder attempting to access a secure area around which the fiber 104 is deployed, perhaps along a perimeter fence or buried in the ground and defining the perimeter. In the case of a data communications application, the fiber 104 might be carrying optical data signals coupled into the fiber by means not shown in FIG. 1, for example at a different wavelength using wavelength-division multiplexing; or the fiber 104 might be a dedicated sensing fiber that is in the same cable as another fiber that is carrying optical data signals.

The detection unit 106 comprises an input lens 118 which receives the light from the distal (downstream) end of the fiber 104 and directs it to each of three beam splitters 120, 122 and 124. The beam splitters 120, 122 and 124 each transmit a portion of the incoming light and reflect a portion to distribute portions of the light to four detectors 126, 128, 130 and 132, respectively, via four polarizers 134, 136, 138 and 140, respectively. (It is noted that the analyzer states of polarization depend not only on the polarizers, but also on the effects of the associated beamsplitters.) The arrangement is such that the incoming light is split and applied to the four polarizers 134, 136, 138 and 140 in approximately equal amounts. Each of the detectors 126, 128, 130 and 132 produces an electrical detection signal whose magnitude is proportional to the optical power that it receives. It alternates between two levels as the launch polarization state is modulated, and these levels may change as the fiber is disturbed. Such an alternating signal is shown as trace C of FIG. 6, one cycle being shown expanded in plot D. Each of the detectors may include an associated amplifier such as a transimpedance amplifier (not explicitly shown), as is common.

The analog electrical detection signals d1, d2, d3 and d4 from detectors 126, 128, 130 and 132, respectively, are supplied to an analog-to-digital converter (ADC) unit 142 in the processing unit 108, where four respective ADCs (not shown) clocked by a local clock signal $CK_D$ (plot D in FIG. 6) from local clock source 146 convert them to corresponding digital detection signals D1, D2, D3 and D4 that are then supplied to a processor 144 in processing unit 108.

The frequency of local clock signal $CK_D$ (plot D, bottom, in FIG. 6) is nominally an integer multiple of the frequency of the polarization clock signal CKp (trace A) generated in the launch unit 100. In this specific embodiment, the frequency of the local clock $CK_D$ is 50 kHz. Consequently, the digital detection signal for each detector comprises 50 samples in each cycle of the polarization modulation, i.e., 25 samples for each half-cycle, as shown in expanded plot D of FIG. 6.

The operations carried out by the processing unit 106 upon the digital detection signals, and the data sets processed, described in general terms with reference to FIG. 4, will now be described in more detail with reference, as necessary, to other Figures.

4.11 Data Acquisition

Data will be preprocessed in blocks containing an integer number of segments corresponding to respective cycles of the polarization modulation and hence the detection signal when properly registered with the segments. In the embodiment of FIG. 1, each one-cycle segment comprises 50 raw-data points i.e. 50 samples from each detector, and the integer number is 100, so a block contains, for each detection signal, 5,000 points representing 0.1 second of data, i.e., 100 cycles of the polarization modulation. (This is in contrast to the 10 points per cycle used for ease of illustration in FIG. 7 and elsewhere.) There are four detection signals so, in process 4.11 (FIG. 4), the processing unit 108 acquires 200 samples per cycle, i.e., 20,000 samples per 0.1 second block and stores them as "raw" data 4.21. Data acquisition techniques are generally known to those skilled in this art and so will not be described in more detail here.

4.12 Pre-Processing

Figure 8:
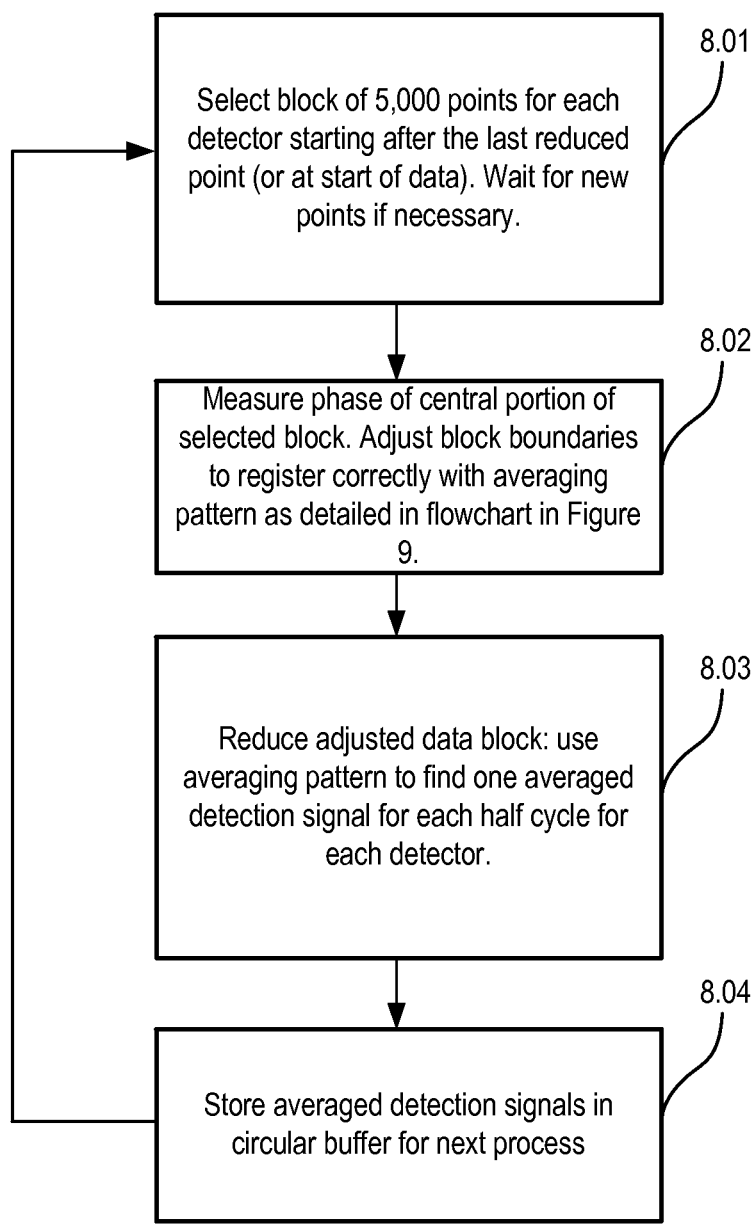
FIG. 8 is a high level flowchart of the phase offset correction and registration process followed by reduction of data points to one per half cycle.
Figure 9:
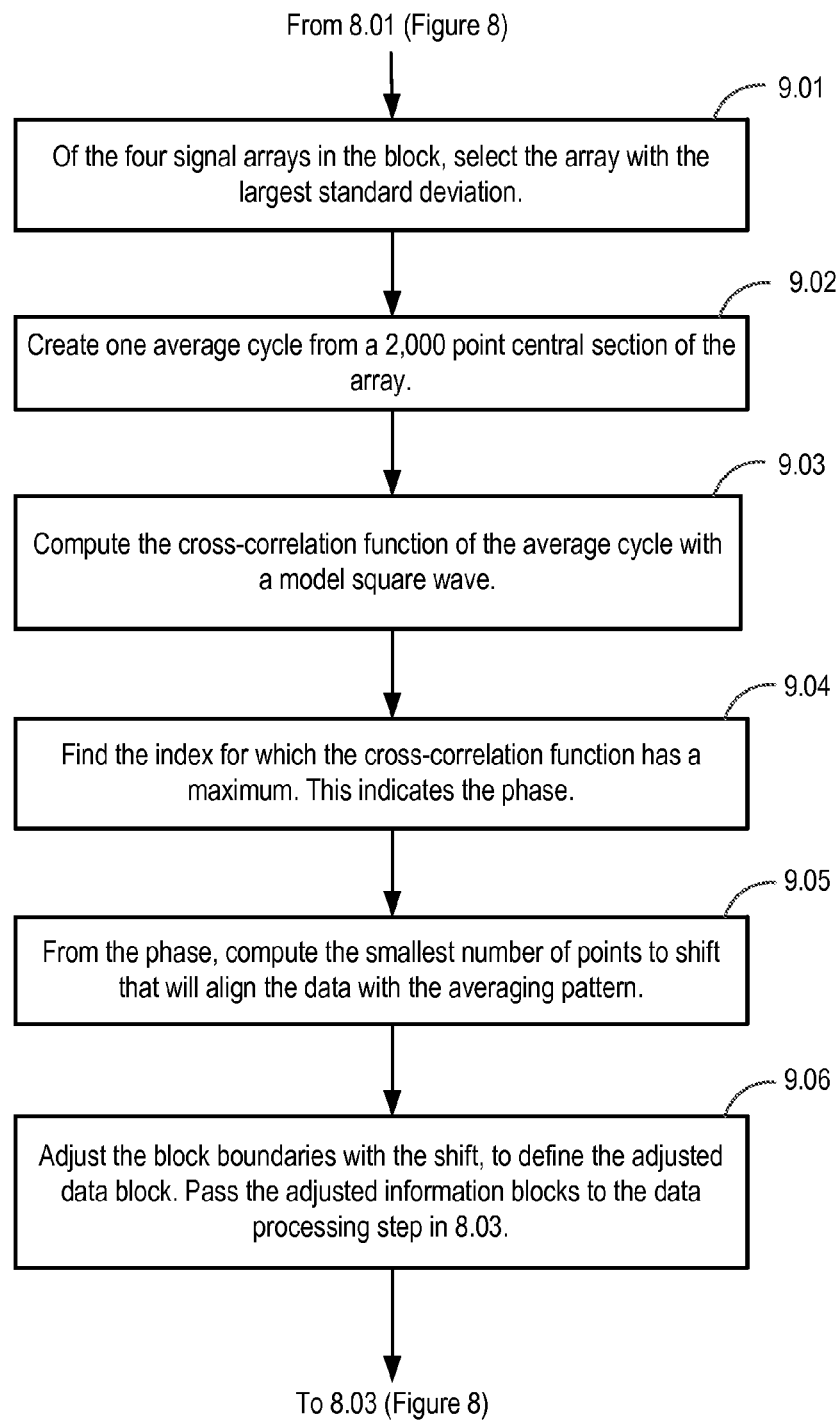
FIG. 9 is a flowchart showing in more detail the phase measurement step of the flowchart of FIG. 8.

Referring also to FIGS. 8 and 9, the pre-processing 4.12 comprises (i) selecting a block of detection signal samples and determining phase offset correction for registration purposes (steps 8.01 and 8.02); and (ii) averaging and reducing selected samples to one averaged value per half-cycle of each detection signal (Step 8.03) and storing the averaged values (Step 8.04).

4.12 (i) Phase Offset Correction and Registration

As mentioned above, the frequency of the clock $CK_D$ (plot D) is chosen to be an integer multiple of the polarization modulation frequency of clock $CK_P$ (trace A), but such integer multiple will not generally be exact due to inaccuracies in the clocking components, and the phase of the polarization modulation will generally drift relative to the ADC clock signal $CK_D$ (plot D). To process the "raw" (un-averaged) digital detection signals D1-D4 properly, it is necessary to correct for "phase offset" and ensure that each set of samples selected for averaging (reduction) does not overlap the transitions, and extends only over a relatively unchanging part of the modulated waveform. The aim is to ensure that the right points are averaged to create the averaged detection signal (4.22) for each half cycle of the data. Equivalently, the aim is to refine the selection of the block so that it is properly aligned or in proper registration with the fixed "averaging pattern".

The "averaging pattern" is a rule that determines which points in a block of data will be averaged to make the average detection signals for each half cycle of the polarization modulation. This pattern and its registration are illustrated by the example of FIG. 7. For ease of illustration and simplification of description, FIG. 7 shows only 10 raw data points per cycle of the polarization modulation, instead of 50.

Each of the plots (a)-(e) shows the waveform of a detection signal as the launch polarization state is modulated. Signal samples marked with × are intended to be used to create an average value for each half cycle, and those marked with circles are intended to be ignored. The pattern of time positions for the × marks and O marks is the averaging pattern. In different traces, the averaging pattern position is slightly different as a result of phase drift between the ADC clock signal $CK_D$ and the polarization modulation waveform. The averaging pattern of trace (d) has poor registration or alignment because for each cycle, two of the points selected for averaging (marked with ×) are on transitions, and two points selected for rejection (marked with O) are in useful stable parts of the data. Trace (e) has the same measured data points but shows that the processor 144 has shifted the averaging pattern by a single raw data point so that it is in proper registration. The earlier traces (a) through (c) in FIG. 7 show slightly different positions for the digitized raw data points because of a phase drift of the sampling times relative to the polarization-modulation waveform, by 0%, 30% and 60% respectively of the time interval between raw points. However, a single registration of the averaging pattern is acceptable for all of these, and that registration only becomes poor when the phase has drifted from its location in trace (a) by nearly 80% of the raw point interval, as in trace (d).

When the system is being built, the ratio of the frequency of the digitizing clock $CK_D$ (from sampling clock 146) to the frequency of the polarization modulation clock $CK_P$ from timing control 116 is made close enough to its nominal integer value to make the drift sufficiently slow so that a single registration of a long periodic averaging pattern will generally suffice for an entire 0.1-second block. In other words, if registration is done well in the middle of the block, then data in the two one-millisecond segments at the beginning and the end of the block will also be sufficiently well aligned with the averaging pattern that transitional effects do not significantly influence the results.

Requirements placed on the four analyzer states of polarization (discussed later) will generally guarantee that at least one of the four time-dependent detection signals d1, d2, d3, d4 has a substantially square waveform with significant amplitude, which can be used for determining the proper registration. Consequently, the processor selects only one of the four detection signals (having the largest amplitude) for use in determining phase offset and registration.

Referring again to FIG. 8, in Step 8.01, the processor 144 selects a contiguous block of raw data 4.21 to be reduced to averaged detection signals 4.22. (This selection is preliminary, and before reduction it may be altered by the phase offset correction, shifting the block's boundaries a small amount to align the data with the averaging pattern. In this example the averaging pattern is fixed relative to the block boundaries, so shifting the boundaries is the same as shifting the averaging pattern.) When the system begins operation, this step 8.01 selects the first 5,000 raw data points (each "point" here meaning a set of four signal samples at a particular time, one from each of the four different detectors), waiting for the data acquisition process to put enough raw data 4.21 in its buffer if necessary. At later times, each new block begins immediately after the last point of the last block of raw data that was reduced. This rule automatically starts the new block with the same averaging-pattern registration that was used for reducing the previous block, although that may be changed by shifting the boundaries after phase measurement in the next step.

In Step 8.02, the processor 144 measures the phase of the polarization modulation that is reflected in the data, and uses the phase information to adjust or modify the boundaries of the 5,000-point block, if necessary, resulting in an adjusted raw data block. Referring to FIG. 9, which illustrates Step 8.02 in more detail, in Step 9.01 the processor takes the four arrays of single-detector signal samples in the block, and computes the standard deviation for each. The array with the largest standard deviation is passed on to the next step for phase analysis, i.e., data from only one detection signal will be used to determine the phase offset correction.

In Step 9.02, the processor prepares for phase analysis by computing a single averaged cycle (50 points) from points 1501 to 3500 in the 5,000-point single-detector block, to provide a low-noise sample from which the phase will be determined. The first point in the average cycle is the average of points 1, 51, 101, etc. in the block; the second point is the average of points 2, 52, 102, etc. in the block; and so forth for all 50 averaged points.

In Steps 9.03 and 9.04, the processor finds the phase of the averaged cycle by determining the shift or index offset that maximizes its correlation with a model square wave having two cycles. A model square wave is constructed as an array of 100 values, of which points 1 through 25 and 51 through 75 equal +1, and the other fifty points equal −1. In Step 9.03, the processor computes a common digital cross-correlation function for the averaged cycle and the two-cycle model square wave and in Step 9.04, finds the index of the maximum of this cross-correlation function, as an indication of the relative shift between the two arrays that best aligns them by this correlation measure.

In Step 9.05, the processor interprets this "peak index" (the index of the maximum value of the cross-correlation function) to determine by how many points (if any), and in which direction (earlier or later), the boundaries of the 5,000-point block should be shifted to align the block optimally with the averaging pattern. In a condition of optimal alignment, transition locations of the model square wave coincide most closely with transition locations in the averaged cycle, without regard for the directions of the transitions. The phase measured in the previous step indicates the nominal positions in the block of all of the positive-going transitions of the selected detection signal; and this, in turn, indicates the nominal positions in the block of all of the transitions (without regard to direction, i.e. positive-going or negative-going).

The exact way that the numerical peak-index value indicates these locations depends on normal choices to be made during programming.

In Step 9.06, the processor shifts the boundaries of the block to align the data optimally with the averaging pattern, comprising the desired sets of samples 5.13 in each half cycle. Many different shifts would qualify to produce optimal alignment, i.e. if a shift by some number $n_p$ of points qualifies, then a shift by $n_p+25$ or $n_p-25$ points (half of a cycle either way) will also qualify. The qualifying shift with the smallest magnitude is chosen, whether it shifts the block boundaries earlier or later in the data. For the embodiment of FIG. 1, the shifted boundaries will place the nominal position of a transition at the start of the block, because the averaging pattern is fixed relative to the block and chosen to make that condition optimal for alignment.

Having determined the amount and direction of the phase offset correction using the data for one detection signal, the processor 144 applies the same phase offset correction to the data arrays of all four detection signals so that they are properly registered and ready for the averaging and reduction process of Step 8.03.

4.12 (ii) Averaging and Reduction

Referring again to FIG. 8, for each of the digital detection signals D1-D4, in Step 8.03 the processor reduces the 50 samples in each cycle of the block to 2 points, one for each half cycle, each point comprising four values that are the average detection signals of the four detectors, the result of using the averaging pattern that was described earlier with reference to FIG. 7 (see also 5.13 in FIG. 5). Thus, referring to FIGS. 5, 6 and 7, the processor 144 discards samples adjacent each of the transitions, i.e., rising or falling edges, and averages at least some of the remaining samples. As shown in plot D of FIG. 6 and all traces but trace (d) in FIG. 7, in this specific embodiment, the processor 144 ignores a prescribed number of samples (two in these examples) that are substantially coincident with a transition, i.e., where the detection signal magnitude is changing rapidly, and averages the remaining samples in each half-cycle, i.e., where the detection signal magnitude remains relatively constant, to produce one average value per half-cycle for each detector.

In Step 8.04, the processor simply stores all of the averaged detection signals from the block, in the circular buffer 4.22 that is designated for averaged detection signals (FIG. 4) enabling use of the data in Process 4.13 to compute fiber change information.

4.13 Computation of Fiber Change Information

The first step in process 4.13 is to determine, from the sets of four detection signals during each half cycle, the two Stokes vectors for the output polarization states in each cycle. The entire Stokes 4-vector may be determined but only the three directional components (excluding the total power component) may be needed; so in the following description only three are computed and used. Conditions placed on the analyzer states in this embodiment (as described later) allow each of the four Stokes components of the light that exits the fiber to be computed as a weighted sum of the four detection signals. In other words, the Stokes 4-vector is S=WP, where P is a column vector of the powers of the four detection signals, and W is a 4×4 matrix of the weights. The desired unit Stokes 3-vector s is then computed in the usual way from three of the Stokes parameters (three components of S, ignoring the power component $S_0$). Computation of the Stokes 3-vector, and calibration for determination of the weighting matrix W, will be described below. For different embodiments with fewer than four analyzer states, the computations and the calibration parameters and methods are different.

Figure 10:
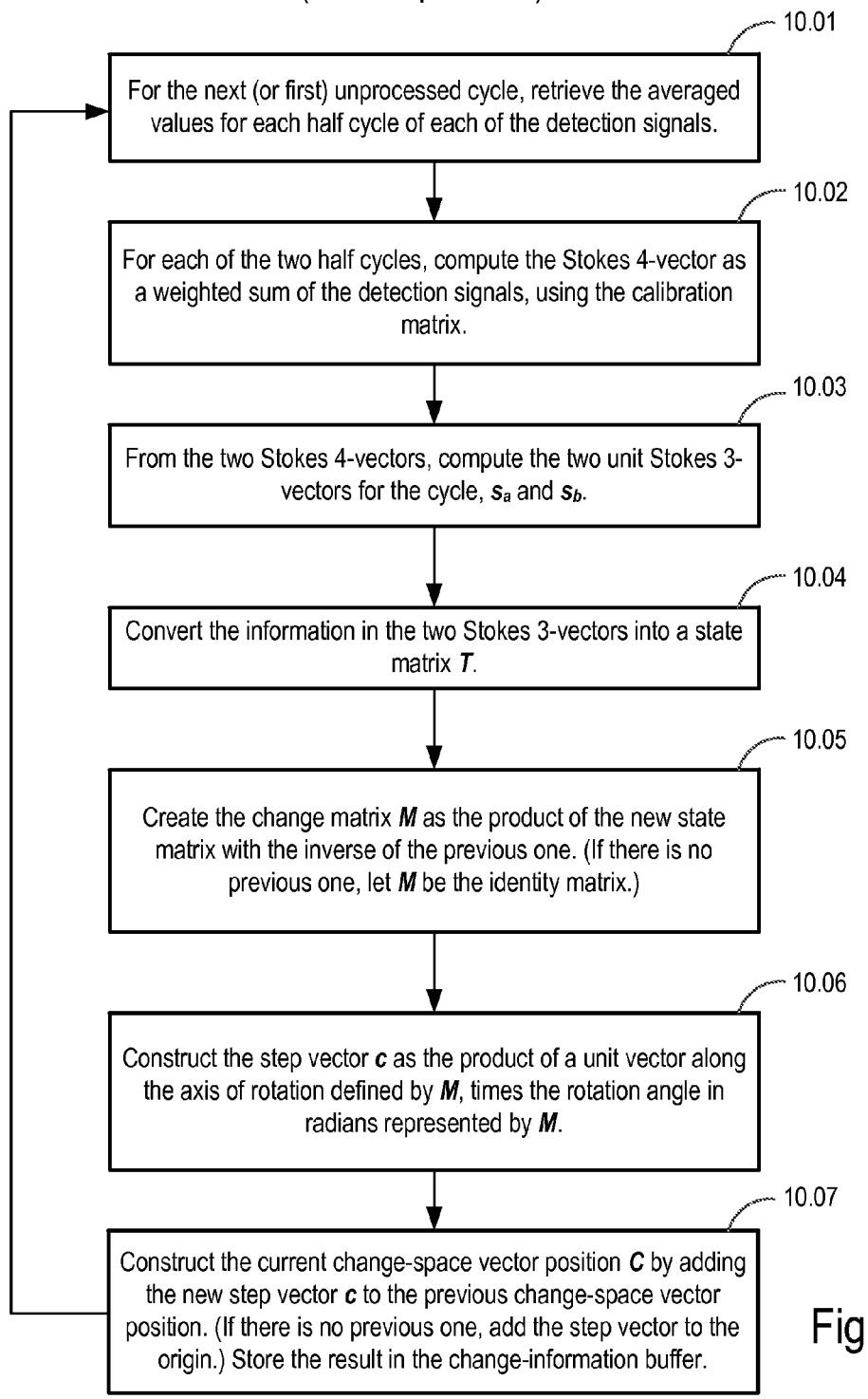
FIG. 10 is a flowchart depicting computation of change information (sequence of change-space position vectors) representing successive positions of the fiber transformation state in a notional three-dimensional space.

The change-information computation procedure (4.13) will now be described in more detail with reference to FIG. 10 which shows seven steps. Details of the steps performed by processor 144, and the equations used, are as follows:

Step 10.01: The processor reads from the buffer two average sample values (one for each half cycle) for each of the four detection signals. Thus, in each cycle there will be eight sample values, the first four corresponding to the first half of a cycle of polarization modulation, and the second four corresponding to the second half cycle.

Step 10.02: For each of the two half cycles, the processor 144 derives a column vector P from the four averaged detection signals and the weighting matrix W used in the formula S=WP, described above, to compute the three Stokes parameters $S_1$, $S_2$ and $S_3$.

Step 10.03: For each of the sets ($S_1$, $S_2$, $S_3$) of three Stokes parameters computed in the previous step, the common normalizing formula $$(s_1, s_2, s_3) = \frac{(S_1, S_2, S_3)}{\sqrt{(S_1^2 + S_2^2 + S_3^2)}}$$

is employed to compute the three components of the corresponding unit Stokes 3-vector. This yields the unit Stokes vectors $s_a$ and $s_b$ for the "a" and "b" halves of the polarization modulation cycle. (see 5.16, FIG. 5)

Step 10.04: To facilitate a particularly convenient method of using two pairs of Stokes vectors to compute the rotation matrix that transforms one pair into the other, the processor constructs a "state matrix" T. Thus, the processor first uses $s_a$ and $s_b$ to define a third unit Stokes vector from their cross product, $s_c = s_a \times s_b / |s_a \times s_b|$, then constructs T by using these three vectors as columns:

$$T = \begin{bmatrix} s_{a1} & s_{b1} & s_{c1} \\ s_{a2} & s_{b2} & s_{c2} \\ s_{a3} & s_{b3} & s_{c3} \end{bmatrix}.$$

This state matrix T contains the same information as the two Stokes vectors $s_a$ and $s_b$, but is an example that provides a convenient method of computation in the next step.

Step 10.05: The change matrix M for the current cycle (see 5.17, FIG. 5), representing the change in the fiber polarization transformation since the time of the previous cycle, is computed by multiplying the present state matrix T (on the right) by the inverse of the previous state matrix $T_0$, so that $M=TT_0^{-1}$.

Step 10.06: The information in the change matrix M is converted into a step vector c (see 5.15, FIG. 5) using formulae based on equations 18 and 19 of section 3-2 in *Rotations, Quaternions and Double Groups* by Simon Altman, Dover, 2005. These formulae are equivalent to computing c as $$c = \frac{\theta}{\sin\theta}\mu,$$

where the three components of the vector μ are computed as $$\mu_x = \frac{M_{32} - M_{23}}{2}, \mu_y = \frac{M_{13} - M_{31}}{2}, \mu_z = \frac{M_{21} - M_{12}}{2},$$

and the angle θ is computed as $$\theta = \cos^{-1}\left[\frac{1}{2}(M_{11} + M_{22} + M_{33} - 1)\right].$$

(When θ is small, if the processor 144 has difficulty evaluating the singular expression θ/sin θ, a second-order approximation $1+\theta^2/6$ may be used for θ/sin θ.)

Step 10.07: The step vector $c(t_0,t_1)$ computed for the change between times $t_0$ and $t_1$ is added to the change-space position vector $C(t_0)$ for time $t_0$ (see 5.19, FIG. 5) to construct the new change-space position vector $C(t_1)$ for time $t_1$. This new vector $C(t_1)$ is appended to the sequence in the buffer for change information 4.23, and the processor returns to step 10.01 to read the next two average sample values of each of the four detection signals.

The foregoing method of computing the Stokes vectors is suitable for the embodiment of FIG. 1, with four different analyzer states. It may not be suitable for other embodiments that may have fewer analyzer states. But the subsequent steps (after determination of the Stokes vectors) are examples that can be applied to sequences of Stokes vector pairs that have been determined by other embodiments employing different hardware and/or other computational methods.

Depending on the processor and programming choices, it is possible that one or more components of the change-space vector C may grow large enough over time to cause a numerical overflow problem or loss of resolution. If that is a danger, Step 10.07 may also include a check on the magnitude of the change-space vector's components. If some prescribed threshold is exceeded, the processor can correct the excess by subtracting one vector (such as the last vector in the buffer) from all the vectors in the buffer, restoring them all to a region closer to the origin in change space, without changing their relative positions.

This operation must be done in a way that is coordinated with subsequent processes 4.15 and 4.16, so that they are prevented from computing a measure from any "mixed" set of data read partly before the correction operation and partly after, and therefore having some incorrect relative positions.

As described hereinbefore with reference to FIG. 4, the change-space-distance computation process 4.14 (Measure-1) and the spectral power computation process 4.15 (Measure-2) determine two different measures of disturbances from the stored Change Information 4.23. In a separate Decisions and Reporting process 4.16, the measures are evaluated with reference to preselected criteria to determine whether a reportable disturbance has occurred. These three processes 4.14, 4.15 and 4.16 will now be described in more detail with reference to FIGS. 11, 13 and 15.

Figure 11:
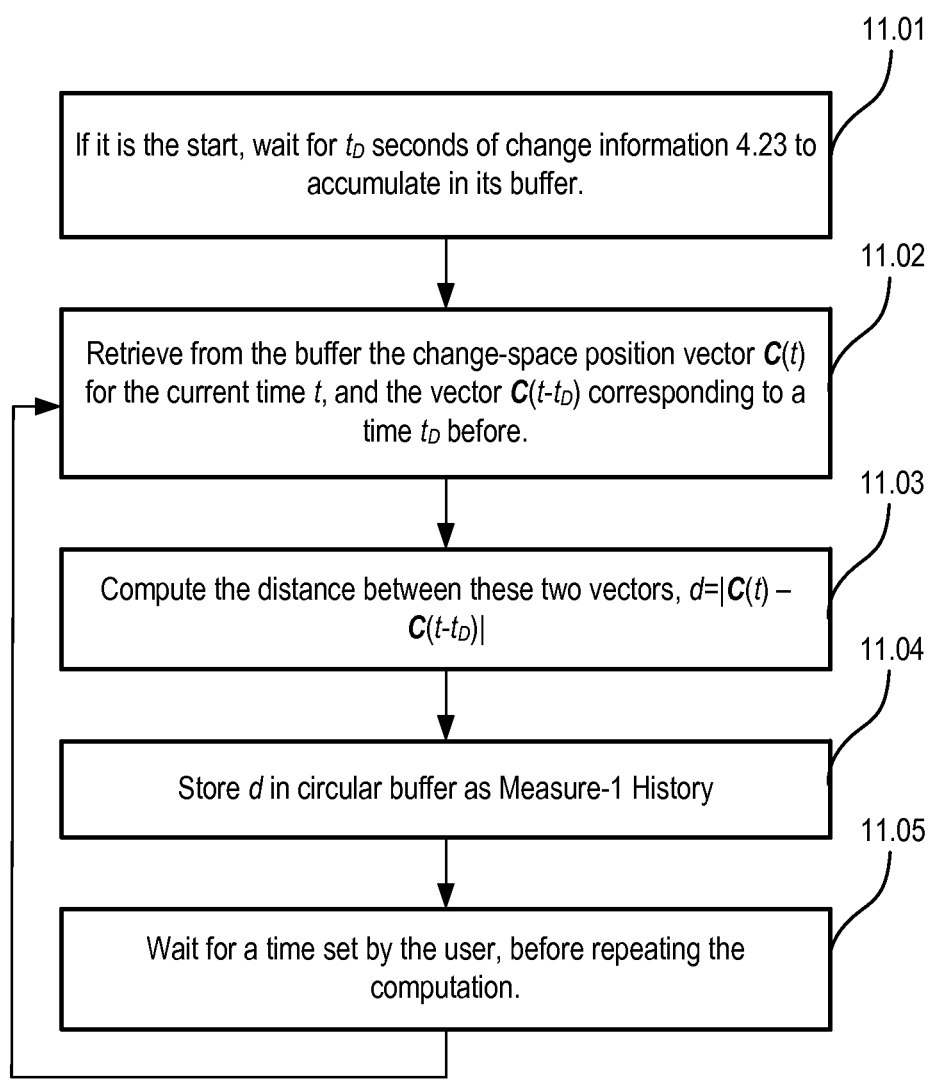
FIG. 11 is a flowchart depicting computation of distance moved in change space over time.

FIG. 11 illustrates the change-space distance computation process 4.14 for deriving Measure-1 and its history. This process depends on a user-defined time interval $t_D$, and a user-defined threshold that represents the maximum amount of net rotation (e.g. in radians) on the Poincaré sphere over any time interval of length $t_D$ that will be tolerated without reporting a disturbance. The time $t_D$ might, for example, be set to 10 seconds, and the threshold to 0.2 radians. Then, if the fiber's change, over any 10-second period that is tested, exceeds 0.2 radian of rotation, a disturbance will be reported. The process of comparing these thresholds will be described by FIG. 15. The steps of FIG. 11 are as follows:

Step 11.01: Before proceeding, the processor ensures that data for a required interval up to time $t_D$ exists in the buffer containing change information 4.23. This needs to be invoked only at startup of the system.

Step 11.02: The processor retrieves two change-space position vectors $C(t-t_D)$ and $C(t)$ from the buffer containing change information 4.23. One is for the present or most recent time t, and the other is for a time $t_C$ ago, which is the time $t-t_D$.

Step 11.03: The processor computes the distance between these two vector positions as the norm of the vector created by their difference. This is a reasonable estimate of the net angle of rotation in Stokes space that characterizes the change in the fiber transformation between the two times, provided the angle is not too large and the change-space motion is not made up of too many steps. Even if it is not a perfect estimate of the angle, it is a good measure for using with reporting criteria.

Step 11.04: The processor stores the computed distance in the buffer for Measure 1 History (4.24).

Step 11.05: The processor waits for a user-set time period, and then repeats the test. The user-set time period will generally be a small or moderate fraction of the time $t_D$ over which the distance is measured, so that successive time intervals overlap and the system is not likely to miss a reportable disturbance just because of timing. For example, the wait time might be 0.3 second.

Figure 12A:
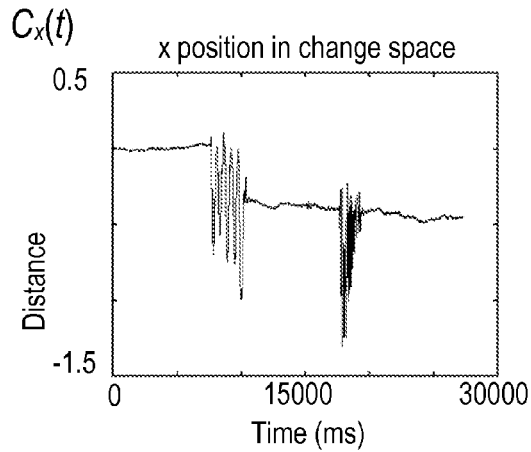
FIGS. 12A, 12B and 12C are graphs which depict the position coordinate in change space over time for each of three change space axes.
Figure 12B:
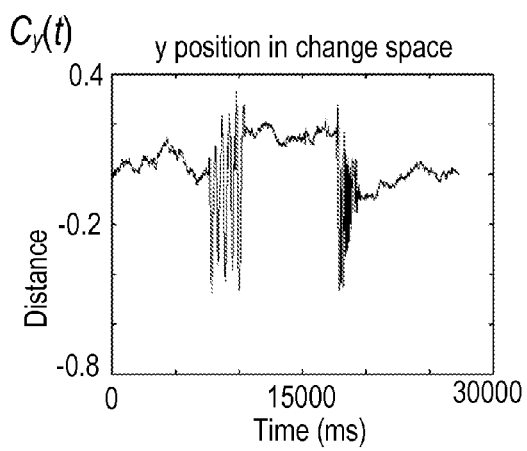
Figure 12D:
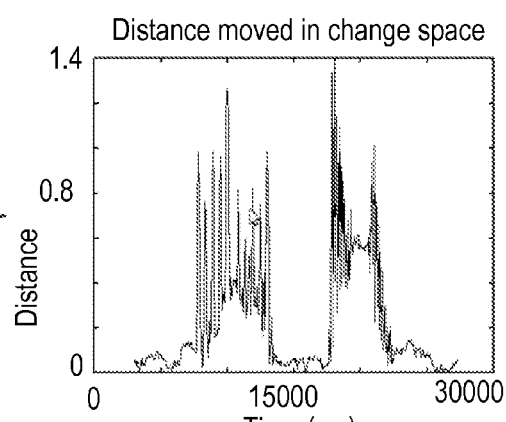
FIG. 12D is a graph depicting the distance moved in change space over a period of 3 seconds as computed by the method of FIG. 11.
Figure 12C:
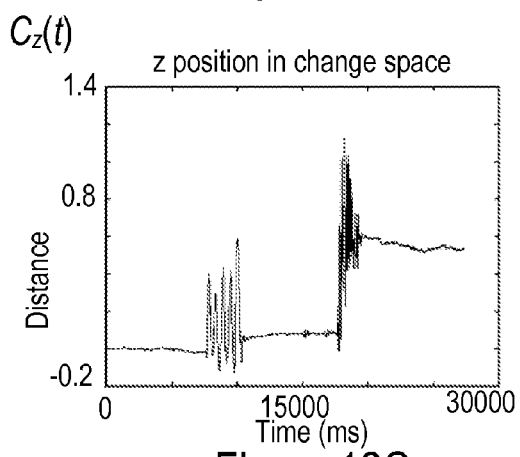

FIGS. 12A, 12B and 12C are graphs showing examples of the x, y and z coordinates, respectively, of the change-space position vector over 30 seconds, while FIG. 12D is a graph of the distance moved in change space in the preceding three seconds, for different times.

It might be useful to apply a low-pass filter to $C_x$, $C_y$ and $C_z$ before computing the distance moved in change space, so that only very-low-frequency changes are assessed by measure-1.

The spectral power computation process 4.15 for Measure-2 also operates on blocks of data that have a fixed length equivalent to a time interval of 0.1 second, over which 100 change-space position vectors are acquired. Its "integrated power" computation depends on a user-defined set of weights for different frequencies, selected on the basis of the relative importance of different frequencies in detecting disturbances that merit reporting. The manner in which such selection will be made will be known to those skilled in the art. The process 4.15 for computing Measure-2 and its history will now be described in more detail with reference to FIG. 13. Thus:

Step 13.01: The processor reads 100 change-space position vectors from the buffer containing change information 4.23, beginning at a location in the circular buffer indicated by a pointer conveniently called the "change-space pointer". It may be necessary to wait until all of the vectors to be read have arrived in the buffer. The set of vectors comprises three one-dimensional arrays, each having 100 points and representing change-space position along one of three mutually perpendicular axes x, y and z.

Step 13.02: The processor computes a power spectrum for each of the three arrays. It does so by first applying a window function, specifically a common Hanning window, to each array, to limit the spectral noise and anomalies that can arise when the end of the array does not match the beginning well. After applying the window function to each array, the processor transforms the resulting data with a Fourier transform, discards the redundant second half of the resulting array points, and squares the absolute values of the complex components to create the power spectrum array. These operations are known to those skilled in the art and described in many books such as The Fast Fourier Transform and its Applications, by E. Oran Brigham, Prentice-Hall, 1988.

Step 13.03: The processor adds the three power spectra to create a single array. This is an "isotropic" power spectrum in that an arbitrary rotation of all the change-space vectors before the computation (e.g. by applying the same 3×3 rotation matrix to every vector) will not change its value for any frequency. The d.c. or "zero-frequency" component is discarded as it will not be used in the subsequent analysis.

Step 13.04: The processor creates an "integrated power" value as a weighted sum of the components of the isotropic power spectrum array. The weighting is predetermined by the user. In practice, the processor may be programmed to allow the user to select (or not select) an option of frequency weighting, which causes each component to be multiplied by a number that is proportional to the frequency that it represents. The processor might also allow the user to specify a frequency band by indicating an upper frequency and a lower frequency, which causes all of the components corresponding to frequencies below the lower value or above the upper value to be weighted by zero, and components for frequencies between these two frequencies to be weighted by 1. After this weighting (multiplication), all the components of the resulting array are added. As is common, the result can be scaled, if desired, for example by dividing by the sum of the weights and/or by multiplication by a factor that controls the units of the resulting value.

Step 13.05: The processor stores the resulting integrated power value in a circular buffer with the capacity for holding all of the computed values over a recent time interval with a duration, for example 10 seconds, that has been preset by the user. The reason for this is that the next step will decide whether to report a disturbance, based not only on the current value of the integrated power, but on properties of its recent history.

FIGS. 14A, 14B, 14C and 14D show, respectively, examples of the power spectra for the three components/directions x, y and z and the isotropic power spectrum obtained by combining them.

Step 13.06: The processor advances the change-space pointer by 50 samples, and returns to Step 13.01 and repeats the process. By advancing 50 points instead of 100, this step ensures that the next set of 100 change-space vectors, read in step 13.01 and subsequently processed, will overlap the set before it by 50 percent.

This overlap provides a simple method of ensuring that changes in relatively short time intervals can influence the integrated power value. The Hanning window used in Step 13.02 severely reduces the signal for times near either end of each set of 100 points. However, in the event that a brief disturbance happens near the end of one interval, so that it is suppressed, the overlap ensures that it will also be represented near the middle of another interval, where it is not suppressed. (It will be appreciated that, if desired, a different window function could be used instead of the Hanning window, and a different amount of overlap could be used.)

Figure 15:
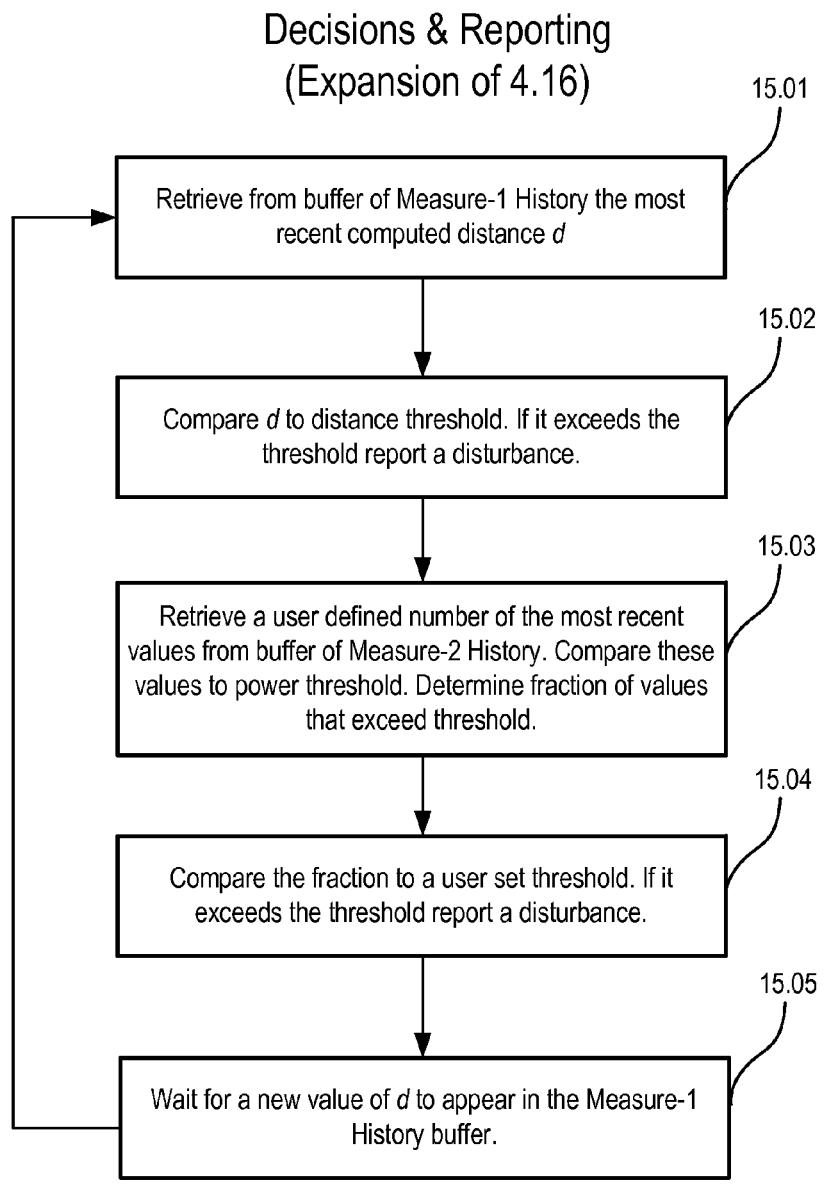
FIG. 15 is a flowchart depicting a possible decision and reporting processing for determining whether or not to report a disturbance.

FIG. 15 illustrates the decisions and reporting process 4.16 for evaluating Measure-1 History data 4.24 and Measure-2 History data 4.25 and determining whether or not to report a disturbance. This process depends on user-defined thresholds as previously described for FIG. 11 and FIG. 13. The steps of FIG. 15 are as follows:

Step 15.01: The processor retrieves from the buffer containing Measure-1 History the most recent computed distance d.

Step 15.02: The distance, d, is then compared to the user set threshold. If d exceeds the threshold a disturbance is reported.

Step 15.03: The processor retrieves from the buffer containing Measure-2 History a user defined number of recent values. Each one of these values is compared to a user set threshold. The fraction of values that exceed the threshold is computed.

Step 15.04: The computed fraction is compared to a user set threshold. If it exceeds the threshold a disturbance is reported.

Step 15.05: Wait for a new value of d to appear in the Measure-1 History buffer, then loop back to 15.01.

In order for the calibration matrix W to exist and work properly, it is necessary for the four Stokes 4-vectors that characterize the four analyzer states to be linearly-independent. This assertion can be proven by noting that the equation $P=W^{-1}S$ defines the four detector powers as a linear sum of the Stokes 4-vector components, and the matrix designated as $W^{-1}$ necessarily exists (even if it is not invertible and its inverse, W, does not exist). Because the P components are just powers or the $S_0$ terms of the Stokes 4-vectors for light passing through an analyzer, each row of $W^{-1}$ is simply the top row of the Mueller matrix that defines the polarization transformation done by the corresponding analyzer (polarization filters 134, 136, 138, 140 combined with other polarization effects in their respective optical paths). But these rows are identical to the Stokes 4-vectors that describe the analyzers. If they are not linearly independent, the matrix $W^{-1}$ is singular and has no inverse. But if they are linearly independent, then the inverse W exists, i.e. there is a calibration matrix. This requirement on the analyzer states is broad, simple and easy to meet without overt requirements on precisely what the states are (e.g. linear, circular, or linear at 45 degrees as in other methods).

A system with four analyzer states characterized by Stokes 4-vectors that are linearly independent will automatically meet the simpler requirement that there should be at least two analyzer states that are polarized to a significant degree and are characterized by Stokes 3-vectors that are linearly-independent. It should be noted that a Stokes 3-vector can characterize an analyzer state so long as it is a polarized state, even though the Stokes 3-vector does not include the extinction-ratio information that a Stokes 4-vector characterization would include. One of the four analyzer states can be completely unpolarized (thus having no associated 3-vector), but not two.

One method for constructing the calibration matrix W is implied by the proof of its existence that appears above. The matrix $W^{-1}$ is simply constructed so that each row is the top row of the Mueller matrix that defines the polarization transformation done by the corresponding analyzer, or so that each row is the Stokes 4-vector that characterizes the corresponding analyzer state. Then its inverse is computed to get W. Alternatively, the matrix W can be determined by methods such as described by Mikhailov et. al, in "Robust Remote Calibration of Fiber Polarimeters," in Optical Fiber Communication Conference, OSA Technical Digest (CD) (Optical Society of America, 2011), paper OWC4.

In order to achieve a good signal-to-noise ratio, it is valuable for the four Stokes 4-vectors representing the analyzer states to be, in some sense, "robustly" linearly independent. If the 4-vectors should be too close to a condition of linear dependence, then, even though the matrix $W^{-1}$ is well-behaved, its inverse W might be nearly singular, in a way that causes the four weights (one row of W) used for computing at least one of the Stokes vector components to include large positive and negative numbers. The weighted sum could then include a small difference between large multiples of two or more detection signals, and would be very sensitive to small noise-induced changes in the measured detection-signal values. The Stokes 4-vectors for the analyzer states should therefore be far enough from a condition of linear dependence to support a signal-to-noise ratio that is sufficient for the particular application.

As an example of a commercial product suitable for use in this application, the General Photonics PolaDetect™ comprises an assembly with four detectors preceded by polarization filters, having analyzer states that can be described approximately as x-polarized, y-polarized, 45-degree polarized and circularly polarized. The states are not perfect in these polarizations or in their relative alignment, and their extinction is not perfect, but this is immaterial. The states have Stokes 4-vectors that are quite different, and may be called robustly linearly independent. The product comes with a calibration matrix provided by the vendor.

Robust linear independence requirements similar to those for the analyzer states apply to the Stokes 3-vectors characterizing the two launch states of polarization. In addition, both of these states should be sufficiently polarized to support a good signal-to-noise ratio. These conditions are not difficult to test (experimentally or with computer modeling) and to achieve, and the range of states that may be used for launch states and analyzer states is broad.

It will be appreciated that the invention is not limited to the above-described embodiment described with reference to FIG. 1, with its two launch states, four analyzer states, and preferred way of processing the detection signal data to determine measures of fiber disturbances that are substantially independent of the launch states and analyzer states of polarization. A number of other embodiments having different combinations of launch states and analyzer states will now be described with reference to FIGS. 16 to 20. These embodiments also will use the detection signal data to compute Stokes vectors, but the methods for computing these Stokes vectors will be different. The subsequent processing, to derive measures of change that are substantially independent of the launch states and analyzer states and to determine whether the changes are reportable, may be the same. Thereafter, modifications to the hardware and processing procedures will be described, some of which apply to specific hardware embodiments and others of which will be applicable to each of the embodiments regardless of the specific launch and analyzer states employed.

The following descriptions of embodiments 2 to 5 may use some symbols and notations that differ from those used in the description of embodiment 1; however, their correspondence with those used for the first embodiment will be apparent from the context.

Embodiment 2: Two Launch States; Two Polarized Analyzer States Plus an Unpolarized Detector A second embodiment, which uses two launch polarization states and two polarized analyzer states plus a polarization-insensitive detector, will be described with reference to FIG. 16. It illustrates the advantage of reduced fading, and the advantage of liberty in selecting the polarization states that are launched into the fiber and selected by the detectors.

Figure 16:
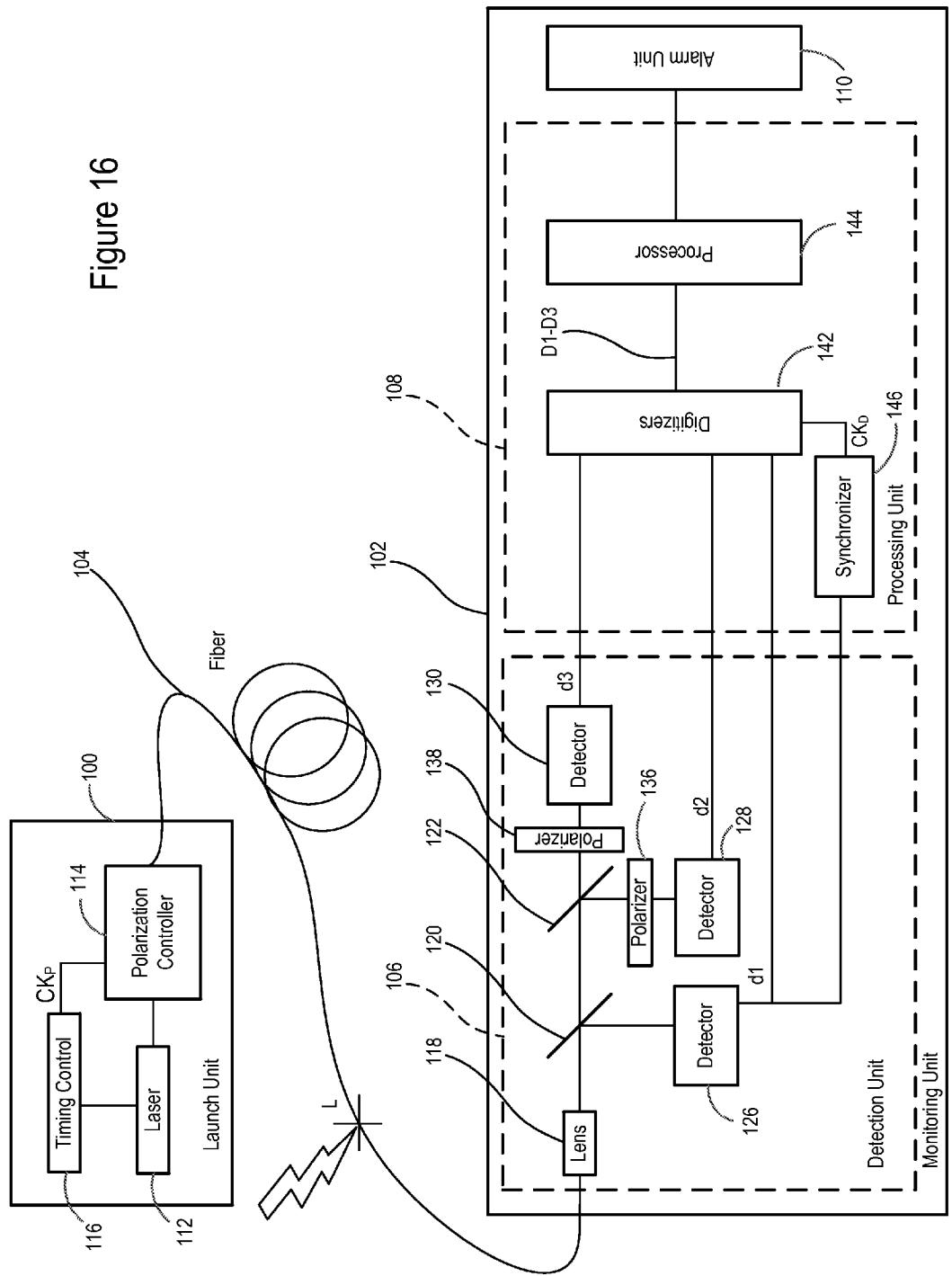
FIG. 16 illustrates schematically a second specific embodiment of the invention in which the launch unit uses two launch states and the detection unit uses two polarized analyzer states and an unpolarized detector.

In FIG. 16, a launch unit 100 and a monitoring unit 102 are shown coupled to proximal and distal ends, respectively, of an optical fiber 104 which might be from a few meters long to more than 50 km. Light in two different states of polarization, launched into the proximal end of fiber 104 by launch unit 100, travels through the fiber 104 and is received at the distal end by the monitoring unit 102 and analyzed for changes consistent with a physical disturbance of the fiber 104 indicative of an intrusion attempt somewhere along its length. Such an intrusion attempt might be movement of the fiber 104 by someone preparing to tap it or another fiber in the same cable, and to extract data signals propagating therealong, e.g., where the fiber is used for communications purposes, or by a person, an intruder, attempting to access a secure area around which the fiber 104 is deployed, perhaps along a perimeter fence or buried in the ground and defining the perimeter. For convenience, the following description will refer, where appropriate, to the data communications application. In such an application, the fiber 104 might be carrying data by means not shown in the figure, such as by light at a different wavelength using wavelength-division multiplexing, or it might be a sensing fiber that is in the same cable structure as another fiber that is carrying data.

The launch unit 100 comprises a linearly polarized laser source 112, a polarization controller 114 and a timing control unit 116. The light from the laser 112 is passed through the polarization controller 114 which, under the control of a 1 kHz timing or clock signal from timing control unit 116, alternately rotates the state of polarization of the light by two different amounts to produce two different linear polarization states. The light in these two states is assumed in this embodiment to be essentially 100% polarized. The timing control unit 116 switches the polarization controller 114 with a 50% duty cycle between the two polarization states, cycling once every millisecond. The polarization controller 114 comprises a device such as the General Photonics PolaSwitch™ product, which accepts linearly polarized input light and switches its output between two linearly polarized states at 45 degrees to each other under control of an external electrical signal.

In each 1 millisecond cycle, the timing unit 116 momentarily increases (or decreases) the output power of the laser 112 to provide a synchronization pulse to "inform" the monitoring unit 102 about the phase of the polarization modulation in the associated one-millisecond period. The timing control unit 116 positions the synchronization pulse at or near a transition between the two states, for example on the rising edge, so as not to waste stable moments that are valuable for signal measurement and averaging. Thus, the launch unit 100 modulates the polarization state at 1 kHz, while at the same time embedding a timing sync pulse.

Referring again to FIG. 16, the detection unit 106 comprises an input lens 118 which receives the light from the distal (downstream) end of the fiber 104, two beam splitters 120 and 122, respectively, three detectors 126, 128 and 130, respectively, and two polarizers 136 and 138, respectively. The beam splitters 120 and 122 are disposed in the light path in succession, each transmitting a portion of the incoming light and reflecting a portion. In the case of beam splitter 120, the reflected light is conveyed directly to detector 126, whereas the reflected light from beam splitter 122 is conveyed to detector 128 via polarizer 136. Finally, the light transmitted by beam splitter 122 is conveyed via polarizer 138 to third detector 130. The arrangement is such that the incoming light is split and applied to the two polarizers 136 and 138 and the detector 126 in approximately equal amounts. The polarizers 136 and 138 are assumed in this embodiment to have essentially perfect extinction. Each detector 126, 128 or 130 is designed to produce an electrical output that is proportional to the optical power that it receives. Typically, each will comprise a photodiode and a transimpedance amplifier, as is commonly used for light detection.

The electrical outputs from detectors 126, 128 and 130 are each supplied to a processing unit, 108, which includes a digitizer unit 142 which comprises three corresponding analog-to-digital converters (ADCs, not shown) for converting the electrical outputs to corresponding digital signals which are supplied to a processor unit 144, which may comprise a microprocessor and/or digital signal processor. The first detector 126 measures unpolarized power and its output is used by the processor 144 for normalizing the outputs of the other two detectors.

The electrical signal from (unpolarized) detector 126 also is supplied to synchronizer unit 146 that uses a phase-locked loop to generate a clock signal that is synchronized to the 1-kHz periodic timing by using the synchronization pulses applied to the light signal in the launch unit 100. The frequency of this ADC clock signal may be 50 kHz as in the first embodiment but could be different, if desired. With that in mind, the following description will use a frequency of 10 kHz.

The synchronizer unit 146 comprises a bandpass filter which filters out unwanted noise before applying the filtered signal to a phase-locked loop (PLL) circuit, which locks onto the periodic synchronization pulses and synchronously generates the ADC clock signal, which is supplied to digitizer unit 142 to clock the separate analog-to-digital converters which convert the signals from detectors 126, 128 and 130, respectively. The corresponding converted digital signals are supplied to the processor 144. The PLL ensures that the ADC clock signal is an exact multiple of the 1-KHz polarization-modulation frequency and has a constant phase relationship to it, obviating the phase-measurement and tracking scheme used for embodiment 1.

In operation, the electrical signal from each of the detectors 126, 128 and 130 is sampled at a sampling rate ten times the rate at which the polarization state is switched. Thus, during each 1-millisecond cycle of the polarization modulation, the processor 144 will sample the amplitude of the optical power incident upon each of the three detectors 126, 128 and 130 five times for each half cycle, i.e., for each polarization state.

For each of the detectors 126, 128 and 130, the processor 144 will measure and average the signals for only three of the five sample intervals for each launch state, ignoring two samples in each half of the polarization modulation cycle that coincide substantially with a state transition, and in one case with the synchronization pulse.)

The processor 144 will normalize power values of the detection signals from the two polarized detectors 128 and 130 by dividing them by the signal from the unpolarized detector 126 and multiplying each of the resulting values by an appropriate calibration factor to create a "normalized" power value, such that a maximum value of 1.0 will occur for either of these detectors if the polarization of the incoming light is exactly aligned with the polarized analyzer state associated with that detector. This normalization avoids variations caused by drift in the laser power or the fiber loss, in known manner.

Once these normalized power values have been obtained, the processor 144 processes them to determine the Stokes vectors for the two states of polarization emerging from the fiber during each cycle of the polarization modulation. These will subsequently be used as they were used in the description of embodiment 1, to determine first a "state matrix" T for each cycle, then change matrices M for successive pairs of state matrices, then step vectors and change-space position vectors, and finally measures of fiber change that are independent of the launch and detection states. As before, reporting criteria are subsequently applied to these measures.

Assume now that s is the Stokes vector for a beam of 100% polarized light, and a detector that receives that light beam is preceded by a polarizing filter with perfect extinction that passes the polarization represented by a Stokes vector d and rejects the orthogonal state represented by −d. Let the normalized signal seen by the detector be m. The relationship between these variables is $$m = \frac{1}{2}(1 + d \cdot s) \quad (e3)$$

Here the dot symbol represents a standard scalar product of vectors. This follows from equation [3.11] of the paper, "PMD fundamentals: polarization mode dispersion in optical fibers," by J. P. Gordon and H. Kogelnik, Proc. Natl. Acad. Sci. USA, Vol. 97, No. 9, pp. 4541-50 (2000), the contents of which are incorporated herein by reference.

For descriptions of how to process the data, we will generalize equation (e3) using the following notation. Let $m_{ij}$ represent the normalized power on polarized detector i when polarization state j is launched into the fiber. Thus, i and j can each range from 1 to 2, and $m_{21}$, for example, is the normalized power measured on the second detector when the first launch state is applied. Let $d_i$ be the Stokes vector that represents the $i^{th}$ analyzer state, and let $s_i$ be the unit Stokes vector that represents the fiber's output polarization state when the $i^{th}$ launch state is launched into it. Then equation (e3) implies that, during each 1-millsecond cycle of the polarization states, the four normalized power values that the system measures are related to the output Stokes vectors and the analyzer Stokes vectors by the following equations:

$$d_1 \cdot s_1 = 2m_{11} - 1 \quad (e4)$$

$$d_1 \cdot s_2 = 2m_{12} - 1 \quad (e5)$$

$$d_2 \cdot s_1 = 2m_{21} - 1 \quad (e6)$$

$$d_2 \cdot s_2 = 2m_{22} - 1 \quad (e7)$$

Here we have rearranged equation (e3) to put the scalar product on the left. The four m values are measured, and we assume that the two d vectors are known, so the only unknown quantities are the two unit s vectors. Since these are unit vectors, each vector comprises only two unknown variables rather than three: knowing two of the components will tell us the magnitude of the third vector component, because the sum of the squares of all three components is 1. Determination of the sign of the third component can be done with help from one additional requirement, that the scalar product between the Stokes vectors representing the two output states is constant:

$$s_1 \cdot s_2 = K_S \quad (e8)$$

Here the constant $K_s$ is calibration information that can be pre-determined for the system, then used for analysis of the data.

For a more explicit explanation of how this defines the x and y components and the z sign relationships, and of some uncertainty that remains for this sign, let us define the x direction in Stokes space as the direction parallel to the vector $d_1$ for the first analyzer state. Let us define the z direction as the direction of the vector cross product $d_1 \times d_2$, and then let us define the y direction as the direction of the vector cross product of a unit vector in the z direction with a unit vector in the x direction. (Here it is assumed that the two analyzer Stokes vectors are neither parallel nor anti-parallel, i.e. they are linearly independent, so that their cross product creates a non-zero z vector.) With axes thus defined, $d_1$ and $d_2$ both lie in the x,y plane. Then, it is clear that equations (e4) through (e7) comprise four equations in the four unknowns that are the x and y components of $s_1$ and $s_2$. They say nothing about the z components of these two vectors, because the scalar products with $d_1$ and $d_2$ annihilate those components. They are linear equations in the four unknowns, and can be solved by standard matrix determinant formulae that are found in many textbooks, or by elementary vector algebra. In fact, the four equations comprise two independent pairs: equations (e4) and (e6) comprise one pair that can be solved without reference to the other two, and equations (e5) and (e7) comprise the other pair. A vector solution for the components of $s_1$ that lie in the x,y plane (or the plane of $d_1$ and $d_2$) is $$(s_{1x}, s_{1y}, 0) = c_1 d_1 + c_2 d_2 \qquad (e9)$$

where the coefficients $c_1$ and $c_2$ are $$c_1 = \frac{2m_{11} - 1 - K_d(2m_{21} - 1)}{1 - K_d^2}, \qquad (e10)$$

$$c_2 = \frac{2m_{21} - 1 - K_d(2m_{11} - 1)}{1 - K_d^2},$$

and where the constant $K_d$ used to define them is the analyzer Stokes vector scalar product, $$K_d = d_1 \cdot d_2 \qquad (e11)$$

Similar equations give the components $s_{2x}$ and $s_{2y}$ of $s_2$ that lie in the x,y plane.

While equations (e4) through (e7) say nothing about the z components of the two output Stokes vectors, adding the requirement that they are unit vectors will tell us the magnitudes of these components:

$$|s_{1z}| = \sqrt{1 - s_{1x}^2 - s_{1y}^2}, \quad |s_{2z}| = \sqrt{1 - s_{2x}^2 - s_{2y}^2} \qquad (e12)$$

The signs of these components are not determined, but the product of their signs generally is determined by using equation (e8), because if both z-magnitudes are non-zero, then changing the sign of one without changing the other will change the value of the scalar product. Changing the signs of both will not affect equation (e8), i.e. this equation cannot discriminate between two mirror images of the pair of Stokes vectors. However, for many applications (including most security applications) this simply does not matter. What would matter is if the computational method caused one or two large z components to change sign suddenly, giving the false appearance of a sudden large change in the fiber. This can be prevented whenever new output Stokes vectors $s_1$ and $s_1$ are computed with equations (e4) through (e8) by applying a simple continuity rule: every time z-components are computed for a new successive short time interval, the signs are chosen to minimize the rotation angle corresponding to the change. (Instructions for computing the rotation angle are given further below.) Alternatively, we can use a similar rule that the signs of the two new z components are chosen, compatibly with equation (e8), in a way that minimizes the largest z-component change for the two vectors. (In the event of equality, we can choose to preserve the sign of the z component of $s_1$.) With either rule, the Stokes vectors are fully determined, and the effect of inadvertent reflections of the two computed Stokes vectors (reversals of both z components) will be minimized. An erroneous reflection may happen due to noise in the detector signals, but it will be when both z components are near zero so that the change is not large, and this will be harmless in most applications.

Having determined the two unit output Stokes vectors before and after the change, we can now finish computing the change matrix M and converting this to change-space information. A procedure for this was shown above, in connection with embodiment 1 and FIG. 10 steps 10.04 through 10.07. The resulting change-space information can then be reduced to one or several measures of fiber change that are independent of the launch states and the analyzer states, and reporting criteria can be applied to these measures, as described above in connection with embodiment 1 and FIGS. 11 through 15.

The computational methods described here allow the change matrix to be computed between any two fiber transformations. As with most measurements, noise or small errors in the raw data (the measured detector signals) may cause errors in the result. In this particular embodiment of the invention, there are conditions under which the effects of electrical or optical noise may be enhanced to a level that is unacceptable in some sensing applications where very small changes need to be detected. Specifically, sensitivity to noise in the detection signals will be enhanced when either one of the Stokes vectors for the two output states lies close to the plane defined by the Stokes vectors for the two analyzer states and the origin. This can be seen from equation (e12) above, where we have assumed that the Stokes vectors for the two analyzer states lie on the equator of the Poincaré sphere. When a vector s is near this plane, the sum $s_x^2 + s_y^2$ is very close to 1, i.e. $s_z$ is close to zero, and the derivative of the computed $s_z$ with respect to either $s_x$ or $s_y$ is large, as simple differentiation of the square-root expression in (e12) will show. Thus a small error in $s_x$ or $s_y$, induced by noise in a detection signal, will cause a large error in the computed $s_z$. (Noise may also sometimes cause the value of $s_x^2 + s_y^2$, as computed from the detection signals, to exceed 1, so that the z-component of one of the Stokes vectors in equation (e12) would be evaluated as a non-physical imaginary number. This circumstance may be handled, for example, by simply setting the z-component to zero, then re-scaling $s_x$ and $s_y$ by the same factor in order to make the sum of their squares equal to 1, before proceeding to computation of the state matrix T.)

Because of its noise sensitivity under those conditions of the fiber that bring either output Stokes vector close to the plane of the analyzer Stokes vectors, this simple embodiment is suitable for applications that can tolerate the noise. In particular, it is suitable for detecting relatively large motions (bending or twisting) of a fiber that happen relatively slowly, so that a narrow bandwidth can be used to reduce the noise. It is also suitable for detecting vibrations (e.g. in machinery), which may have higher frequencies but for which all of the acoustic power is confined to a narrow bandwidth, creating a spectral peak that stands out clearly above broadband noise in a power spectrum. In both of these types of application, the invention is advantageous for its low fading, which provides a more consistently reliable assessment of the magnitude of a disturbance than prior art.

Embodiment 3: Two Launch States; Two Analyzer States

Figure 17:
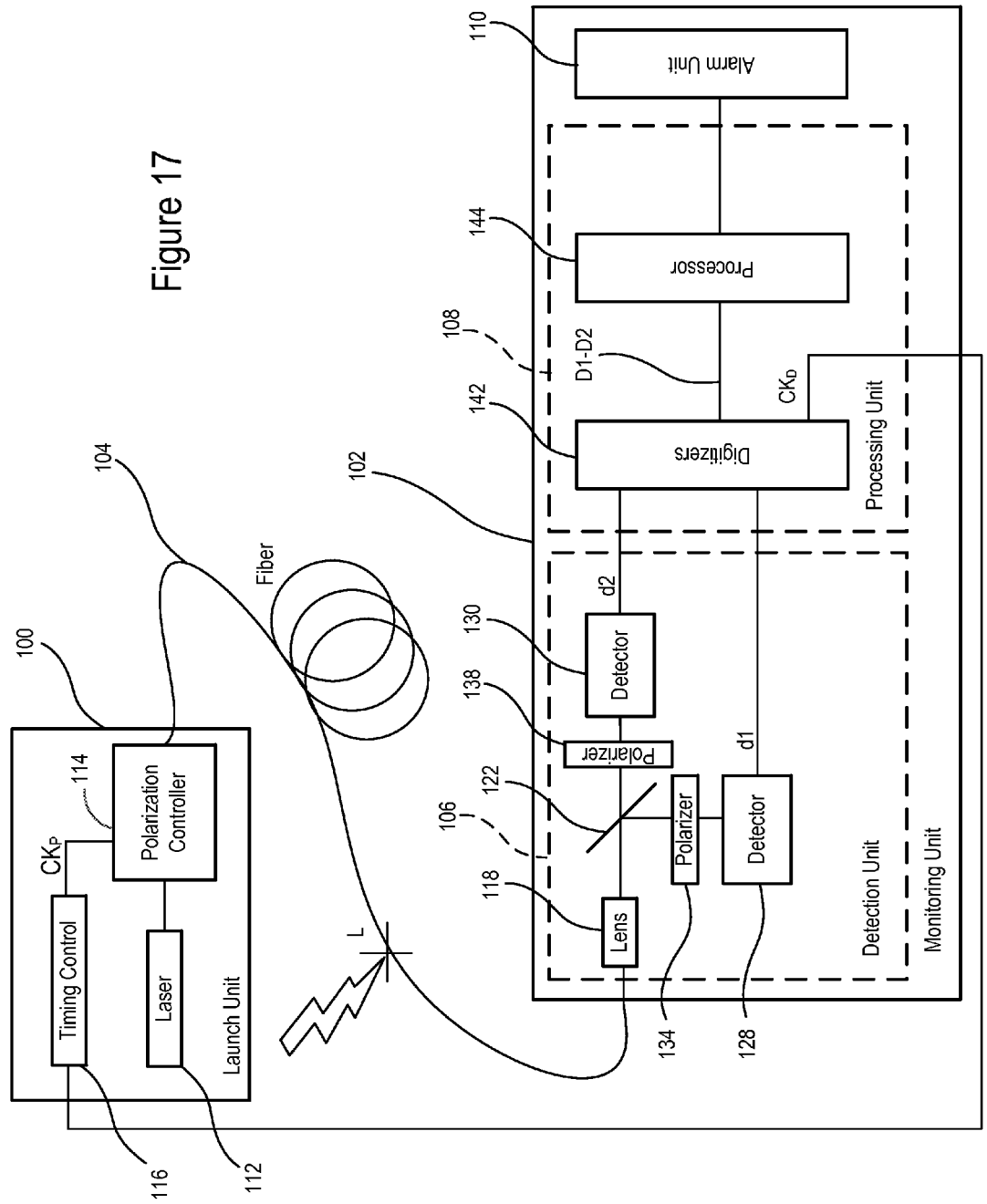
FIG. 17 illustrates schematically a third specific embodiment of the invention in which the launch unit uses two launch states, and the detection unit uses two analyzer states and a clock signal from the launch unit.

A third embodiment of the hardware is illustrated in FIG. 17. It is similar to the embodiment described above in connection with FIG. 16, except for three specific differences with advantages that can reduce the cost in particular applications, and that can mostly be implemented independently of each other in different combinations to suit a particular application.

A first difference is that the synchronizer 146 that tracks the polarization modulation frequency and phase is eliminated, and replaced by a simple direct connection of the timing control unit 116 to the digitizer block 142. This is especially suitable for applications where the fiber 104 is short, or where it is long but looped back, so that the launch unit 100 and the monitoring unit 102 are close together and a direct connection is easy. Also, the timing control unit 116 no longer needs to cause periodic higher-intensity pulses of the laser 112 to act as synchronization markers, and the laser 112 is simply held at steady power.

A second difference, not explicitly apparent from FIG. 17, is that the light launched into the fiber 104 may have a significant unpolarized component (it is not necessarily 100% polarized), and the polarizers 136 and 138 may have significantly imperfect extinction ratios. In this case, the degree of polarization of the light, and the extinction ratios, are assumed to be stable, and to be known. (This added tolerance and flexibility with respect to the launch and analyzer states is reflected in the equations for data reduction, and similar enhanced equations could be used for Embodiment 2 as well.) A third difference is that the polarization-insensitive detector 126 in FIG. 16 is eliminated, along with its associated beamsplitter 120 and the associated analog-to-digital converter in the digitizer block 142. In this case, the optical power is assumed to be known by other means, such as a prior calibration combined with a laser unit 112 that is known to be stable.

For this embodiment, equation (e3) will be modified to reflect the partial polarization and extinction. We can derive the modified equation in a standard way by creating a Mueller matrix for the detector with partial extinction, and applying it to the four Stokes components that describe partially polarized light. However, another simple approach is presented here. A partially polarized light beam behaves like an incoherent sum of two beams, one unpolarized and another fully polarized, with the power divided between them in a way that depends on the degree of polarization. Also, a filter with imperfect extinction passes an amount of light from a beam (whether polarized, unpolarized or partially polarized) that equals the sum of what would go through two filters, one unpolarized and the other polarized with perfect extinction. The two hypothetical filters include attenuation values that depend on the extinction ratio of the real filter that they mimic. Thus the total power $P_t$ that is detected can be written as a sum of four powers:

$$P_t = P_{uu} + P_{up} + P_{pu} + P_{pp}. \tag{e13}$$

Here the subscripts u and p represent unpolarized and polarized respectively, and the first subscript refers to which of the two hypothetical detectors sees this power, while the second refers to which light beam is being detected. The first three terms on the right of equation (e13) are all constant, independent of the relative orientations of the polarized parts of the light beam and the detector filter. For example, $P_{up}$, the power detected by the hypothetical unpolarized detector from the polarized component of the light, will not vary as the fiber is disturbed. Only the last term $P_{pp}$, representing detection of the polarized part of the light with the polarized part of the detector, varies as the fiber's transformation varies, and it behaves exactly like equation (e3), except for a scale factor that accounts for the fraction of the light that is polarized and the attenuation of the hypothetical polarized detector. As a result, the fraction m of the total power in the beam that is detected by a particular detector depends on the output unit Stokes vector s of the polarized part of the light in the following way:

$$m = \frac{\alpha}{2}(1 + d \cdot s) + \beta, \tag{e14}$$

wherein $\alpha$ and $\beta$ are numbers that can be determined by twisting and bending the fiber (or otherwise changing s without altering the optical power) to find both the maximum of m (equal to $\alpha+\beta$, when s is parallel to d) and the minimum (equal to $\beta$, when s is anti-parallel to d); or by straightforward computations from measurements of the extinction ratio and loss of the particular detector and the degree of polarization of the light. The equivalents of equations (e4) through (e7) therefore have the form $$d \cdot s = 2\frac{m - \beta}{\alpha} - 1. \tag{e15}$$

As before, this results in two pairs of linear equations, each pair determining the x and y components of one of the two output Stokes vectors. They can be solved for $s_1$ and $s_2$ in the same way as for Embodiment 2, except that the number on the right is computed in a different manner from the measured signals. If the total power is not correctly known but is consistently "wrong" by some factor, the computed value of m may not correctly represent the fraction of the real optical power that is detected, but the calibration of $\alpha$ and $\beta$ by determining the maximum and minimum m values will be altered in a way that will still give a correct result for d·s. That is evident from equation (e15), where scaling m, $\alpha$ and $\beta$ by the same factor will make no change. What matters is that m, as computed by some means from the measured detector signals, is proportional to the fraction that is detected. That will be true if m is simply proportional to the optical power, which is common for detection circuits and not hard to achieve.

As with the first hardware embodiment, once the output Stokes vectors $s_1$ and $s_2$ are determined both before and after a change, they can be used to determine the change matrix M by the method previously described. As for Embodiment 2, this simple implementation of the invention will have enhanced noise sensitivity under certain conditions, and is therefore especially suitable for applications such as slow large fiber motions or resonant vibrations, where a moderate noise level can be tolerated.

Embodiment 4: Two Launch States; Three Analyzer States

Figure 18:
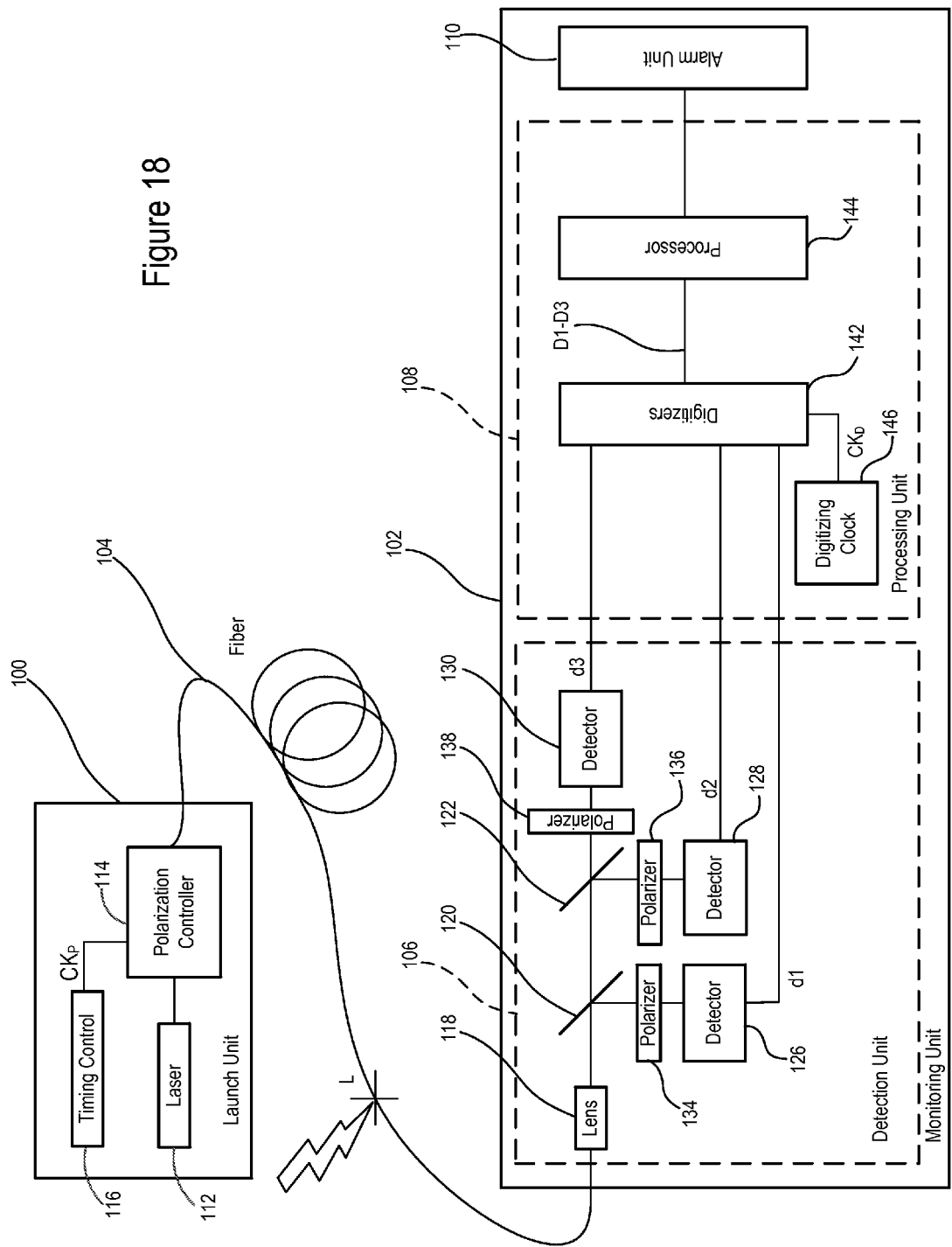
FIG. 18 illustrates schematically a fourth specific embodiment of the invention in which the launch unit uses two launch states and the detection unit uses three analyzer states.

A fourth preferred embodiment of the hardware is illustrated in FIG. 18. It is similar to the hardware embodiment described above in connection with FIG. 17, except for specific differences described below that have performance advantages that may suit particular applications. For high-sensitivity applications, the addition of a third polarized detector has the advantage of preventing the enhanced noise sensitivity that is found in the two previously described second and third embodiments.

In comparison to FIG. 17, a first difference of FIG. 18 is that a third detector 126 has been added with a beamsplitter 120 for deflecting part of the light to this detector, and with a polarizer 134 for polarizing the light. As in the hardware embodiment of FIG. 17, all three polarizers 126, 128 and 130 can have poor extinction. There are three analog-to-digital converters in the digitizer unit, one for each detector.

A second difference is that the direct connection from the timing control unit 116 to the Digitizers 142 is eliminated, and the timing control unit does not feed synchronous clock information to the digitizer unit to tell it when to convert. Instead, there is a digitizing clock 146 that triggers conversions asynchronously at a faster frequency of 100 conversions per cycle of the polarization modulation, or 100 kHz. The digitizing clock 146 and the timing control unit 116 that generates the polarization modulation frequency are not synchronized or locked together, so their relative phase will drift. Stated differently, the digitizing frequency is nominally an integer multiple of the polarization modulation frequency, so that the points in time when the signals are digitized will be very close to the same for each successive cycle; but this is not exactly true, so the pattern of digitizing times will drift slowly relative to the polarization modulation waveform. To accommodate this drift, the processor discerns the phase, and adjusts its processing accordingly, by a method similar to that previously described for Embodiment 1. Furthermore, the output of the timing control unit 116 that controls the polarization modulation is not a symmetric square wave. Instead, it causes the polarization control unit to dwell 55% of the time on the first polarization state, and 45% of the time on the second state. (This description will continue to refer to the two "half cycles" even though one is a little more than half, and the other is a little less.) The reason for this asymmetry is to enable the processor to determine which half cycle is for which launch state. That was not necessary for Embodiment 1, but is useful for this embodiment.

Both the timing control unit 116 and the digitizing clock unit 142 are controlled by crystal oscillators so that the 100:1 ratio of the digitizing frequency to the polarization modulation frequency is accurate to one part in 20,000. This implies that for each successive 0.1-second block of data (100 polarization modulation cycles and 10,000 digitizing events), the position of the phase of digitizing will drift at most by one half of a digitizing period relative to the polarization modulation waveform. The signal for each half cycle is found by averaging a number of points, only now there are more points and some asymmetry, so that 45 points are averaged during the first (longer) half cycle, and 35 points are averaged for the second (shorter). Ten points are discarded during each transition. (The choices of these numbers depend on the transition speed of the polarization control unit 114.) Before computing these averages for the two half cycles, the processor determines the phase to use for the entire block, by examining a the signal from a selected one of the three detectors over a section of the block of 10,000 points, comprising 1,000 points, or 10 polarization modulation cycles, in the middle. The selection process and the examination method are described in the next two paragraphs below.

For selecting which of the three detector signals to examine for phase, the processor computes the mean-square deviation of each signal from its average, over the central 1,000 points that will be examined, and it selects the signal for which this deviation is the largest. At least one of the three will have a non-zero amplitude of modulation due to the polarization switching. This results from "substantially linearly independent" requirements that we will impose on the three analyzer states and on the two launch states. Those requirements and the results are explained further below, after presentation of the mathematics for data reduction.

For examining the central 1,000 points from the selected detector for phase, we first average all ten successive cycles of data to produce a single 100-point cycle with unknown phase and reduced noise. Then we modify this 100-point waveform by subtracting its mean. Then we digitally convolve this with a synthesized model waveform that is two cycles long, comprising 55 points of value +1, 45 of −1, 55 of +1, and 45 of −1, to produce a correlation function of the measured waveform with an ideal waveform. Then we find the index, in the resulting correlation function, where the absolute value of the correlation function is a maximum. This tells us, by standard techniques, where the boundaries of the two half cycles are, i.e. it tells us the desired phase. The details of the implementation will of course vary, depending on the programmer.

In the example of this embodiment, each block of data that is processed is meant to be "aligned" so that its start is very close to a transition to the longer (55%) first phase from the shorter (45%) second phase of polarization modulation. This ensures that the first several points and the last several points in the 10,000-point block are near the transitions and therefore will be ignored. Therefore, the phase of processing (the choice of which points to integrate in each half cycle) for each block can be shifted by one or two points based on the measured phase of that block, with no need to add points to either end of the block. Besides its use for selecting which points to integrate, the measured phase for each block will be used to properly align the phase of the next block of data by shifting it relative to the data stream, either by collecting more than 10,000 new points and discarding one or more points from the beginning, or by collecting fewer than 10,000 new points and adding one or more points to the beginning from the end of the previous block. This continual phase measurement and re-alignment is how the system tracks the phase of the data. The number of points by which each block is shifted (according to the measured phase of the preceding block) will generally be zero, +1 or −1. An exception is that the first block, seen when data collection begins, may have a large phase shift so that a large number of extra new points will need to be added to the end of the second block to bring it into alignment; and so that this first block has only 99 complete cycles of non-transition data, plus fractional cycles at the beginning and the end. The first block will therefore be used only for phase measurement, and other computations will be done only for blocks after the first. These other computations comprise the determination of 100 sets of six average detector signal values (one set for each 1-millisecond cycle, each set comprising three average detector signals for the first polarization state and three for the second), subsequent determination of output Stokes vectors and change matrices, and subsequent processing for alarms, measurements or other assessments.

For signal processing to determine the changes in the two output Stokes vectors $s_1$ and $s_2$, the processor will use equations similar to (e14) or (e15) to indicate the information about a Stokes vector that is derived from the signal on a detector. However, we will include a separate parameter that is related to the power of the laser, in order to show how that can be determined from the three polarized-detector signals, without using a polarization-insensitive detector as in the second embodiment, or a separate means for knowing it such as calibration as in the third embodiment. Equation (e15) indicates a linear relationship between the scalar product of the output and analyzer Stokes vectors and the measured signal on the detector. Instead of the symbol m, which we have defined as the fraction of the light that is detected, let us use a symbol $P_i$ to designate the power on the $i^{th}$ detector in some units. Then equation (e15) can be expressed in an equivalent manner as $$d_i \cdot s = \frac{2}{\alpha_i} m_i - \left(\frac{2\beta_i}{\alpha_i} + 1\right) = \frac{2 P_i}{\alpha_i P_0} - \gamma_i. \tag{e16}$$

Here $\gamma_i$ is defined in terms of $\alpha_i$ and $\beta_i$ as the expression in parentheses. We will consider $\alpha_i$ and $\gamma_i$ to be the calibration parameters (instead of $\alpha_i$ and $\beta_i$). We have expressed the detected fraction of the light as $m_i = P_i/P_0$, where $P_0$ is a measure of the total power that is proportional to the actual power and is consistent with $P_i$ and the means for calibrating $\alpha_i$ and $\gamma_i$. The calibration parameters $\alpha_i$ and $\gamma_i$ depend on the individual detector and on which output state is being measured. They are determined in a way that makes the expression in this equation range from −1 to +1 as s is rotated through all positions on the Poincaré sphere.

It is convenient to rewrite equation (e16) for all three detectors in a matrix and vector notation:

$$Ds = 2ap - g. \tag{e17}$$

Here D is a matrix in which each row comprises the three components of one of the analyzer Stokes vectors, and its product with the column vector s creates a column vector in which each element is one of the scalar products of equation (e16). The parameter a is the reciprocal of the total power measure $P_0$ in the light beam (not just the polarized part represented by the Stokes vector s), and we will call it the "power factor." Each element of the column vector p is not $P_i$, but a term $P_i/\alpha_i$ that can be called "corrected power", and each element of the column vector g is one of the terms $\gamma_i$ that appears in (e16).

We assume that the three analyzer Stokes vectors are linearly independent. This implies that the three rows of D are linearly independent and therefore, as is commonly known, the matrix is non-singular and has an inverse $D^{-1}$ that can be found by well-known methods. The Stokes vector s can therefore be expressed as $$s = aq - r, \quad (e18)$$

where for convenience we have defined new vectors q and r as $$q = 2D^{-1}p, \quad r = D^{-1}g \quad (e19)$$

These are vectors in Stokes space, mapped by $D^{-1}$ from the sets p and q of quantities derived from detector signals and calibration parameters. Note that q depends on measurements of the light, and varies as the fiber is disturbed; but r depends only on the analyzer states, combined with information about extinction of the analyzer filters and the degree of polarization of the light.

Because $D^{-1}$ and g depend on calibration information that we assume is known, and the corrected power information in p comprises a combination of measured signals with known calibration information, equations (e18) and (e19) define the Stokes vector s precisely if the power factor a is known. But this embodiment is meant to address cases where the power may drift and we need to track it, or where it is unknown when a system begins operation, so a must be determined. Information about a is provided by the fact that s is a unit vector. Therefore, $$1 = s \cdot s = |q|^2 a^2 - 2[q \cdot r]a + |r|^2. \quad (e20)$$

This has the common form $$Aa^2 + Ba + C = 0, \quad (e21)$$

where $$A = |q|^2, \quad B = -2q \cdot r, \quad C = |r|^2 - 1 \quad (e22)$$

Equation (e21) has two possible "roots" or solutions for a, which we will denote as $a_+$ and $a_-$ and which can be expressed as $$a_+ = \frac{-B + \sqrt{B^2 - 4AC}}{2A}, \quad a_- = \frac{-B - \sqrt{B^2 - 4AC}}{2A}, \quad (e23)$$

We need to select between these two roots to have a solution, but before proceeding with that subject we will make some brief mathematical observations. With elementary algebra, it is possible to solve (e18) for q and substitute this into (e22) and (e23) to derive an expression for the "wrong" solution $a_w$ in terms of the correct a-value and the actual Stokes vector s:

$$a_w = \frac{a}{1 + \frac{2}{C}(1 + r \cdot s)}. \quad (e24)$$

Whether this wrong solution $a_w$ is $a_+$ or $a_-$ depends on the sign of the $(1+r \cdot s)$ term in the denominator. A quantity related to this term is the "discriminant" Q, defined as $$Q = B^2 - 4AC = \frac{4}{a^2}(1 + r \cdot s)^2. \quad (e25)$$

The two roots are equal ($a_+ = a_-$) when the discriminant is zero. The rightmost expression is the square of a real number, implying that the discriminant is never negative, so that both of the roots (e23) are real. It is also noteworthy that the discriminant can attain a value of zero for any system that allows the unit output Stokes vector s to vary over its full range. This follows from the fact that a unit vector s can always be found that makes $r \cdot s$ equal $-1$ in (e25), which results from the fact that the magnitude of the vector r is greater than unity. To see this, note from the definition (e19) that $g = Dr$. Since each row of the matrix D is one of the three analyzer Stokes vectors, this means that each component $\gamma_i$ of g is the scalar product of r with the unit vector $d_i$, which can be written as $$\gamma_i = d_i \cdot r = |d_i||r|\cos \theta_i, \quad (e26)$$

where $\theta_i$ is the angle between the two vectors. The cosine must be less than 1 for at least one index i, because we are assuming that the three vectors $d_i$ are linearly independent; and the magnitude of $d_i$ is 1. Therefore the magnitude of r must be greater than $\gamma_i$. But each $\gamma_i$ is greater than or equal to 1, from its definition in (e16) and the fact that $\alpha$ and $\beta$ are both non-negative. Therefore the magnitude of r is greater than 1.

For selection between the two solutions, we will assume that the light intensity is steady and changes significantly more slowly than the fiber's transformation. This implies that the wrong solution in (e24) will change in value as s changes, while the correct solution will be nearly constant. That provides a selection criterion. In this embodiment, we continually compute the "recent average" of the selected a value over a recent time period. This time period is adjustable and may typically be on the order of 1 to 10 seconds for a security system. Each time that a Stokes vector is determined, we pick the solution $a_+$ or $a_-$ that is most nearly equal to the recent average value of a.

This embodiment has a selection enhancement method that overrides the simple selection rule described above, in particular cases. The enhancement provides means to initialize the recent average value when the system begins operation, and to recover from an error that may have latched the system to the wrong solution for the power factor a. Such an error can occur, for example, when Q in equation (e25) is close to zero so that the correct and wrong solutions, related by (e24), are approximately equal. Suppose now there is a significant drift in the laser intensity, and simultaneously there is a drift in the fiber that causes the wrong solution $a_w$ of equation (e24) to stay nearly constant, while the correct solution drifts. Although this is unlikely (and good control of the laser intensity will make it more unlikely), the algorithm described above could cause the wrong solution to be tracked to a point in time where the two solutions are significantly different, changing the effective sensitivity of the system until the condition can be discovered by the signal-processing software and corrected. That possibility is a motivation for the selection enhancement method described below.

Until now we have discussed using the detector signals to determine the Stokes vector for a single output state. But there are two output states, and the selection enhancement method will take advantage of this. The two output states can be distinguished notationally by adding a subscript 1 or 2 to the vectors s, s', p, g, r and q, and to terms such as A, B, Q, C and a. The vectors D and $d_i$ are properties of the detectors that do not depend on which output state is being measured.

A first aspect of the selection enhancement method is the use of the power ratio of the two output states. Depending on the polarization control unit 18, the two powers may or may not be identical, but we can at least make it so that the ratio is quite constant. This ratio is measured and recorded as a power-ratio calibration parameter $K_p$, defined as $$K_p = \frac{a_1}{a_2}, \tag{e27}$$

where $a_1$ and $a_2$ are the power parameters a for the two output states. Each time we compute the Stokes vectors, we compute this ratio for all four combinations of possible solutions:

$$K_{p1} = \frac{a_{1+}}{a_{2+}}, K_{p2} = \frac{a_{1-}}{a_{2+}}, K_{p3} = \frac{a_{1+}}{a_{2-}}, K_{p4} = \frac{a_{1-}}{a_{2-}}. \tag{e28}$$

Here $a_{1+}$ means the solution $a_+$ computed from equation (e23) for the first output state, $a_{2+}$ means the solution $a_+$ for the second output state, and so forth. These four "trial $K_p$ values" $K_{p1}$ through $K_{p4}$ will be used for selection as described below.

A second aspect of the selection enhancement method is the use of the angle between the Stokes vectors of the two output states, or equivalently the use of its cosine, which is the scalar product of the two vectors. We expect this to remain constant. The scalar product is measured and recorded as angle calibration information $K_a$, and is related to the Stokes vectors by the equation $$K_a = s_1 \cdot s_2. \tag{e29}$$

We define $s_{1+}$ as the Stokes vector s computed from equation (e18) using $a_{1+}$ and the measured information $q_1$ for the first output state, and so forth. Each time we compute the Stokes vectors, we compute this scalar product for all four combinations of possible solutions:

$$K_{a1} = s_{1+} \cdot s_{2+}, K_{a2} = s_{1-} \cdot s_{2+}, K_{a3} = s_{1+} \cdot s_{2-}, K_{a4} = s_{1-} \cdot s_{2-}. \tag{e30}$$

These four "trial $K_a$ values" $K_{a1}$ through $K_{a4}$ will be used for selection as described below.

A third aspect of the selection enhancement method is that, at times determined by a pre-established rule, we record the set of four trial $K_p$ values and four trial $K_a$ values for some number n of measurements in a row, and each time we compare all n sets of values to the corresponding calibration values. If the values for a particular combination of solutions give better agreement with the calibration values for all n measurements than the current selected combination, then we switch to using that combination as the selected combination. If, as a result, we have switched the solution for the first Stokes vector, then we force the recent average value for $a_1$ to be the new value. The same applies to $a_2$, if its solution has been switched. In the example of the present embodiment, we compute and record the different measured $K_p$ and $K_a$ values for the last ten cycles of each block of 100 cycles of the polarization modulation. Then, a decision to switch the selected combination of solutions, if it is made, is applied to the signal processing for the next block of 100 cycles. Also in this example, assessments of changes in the fiber's polarization transformation are made independently for each block of 100 cycles, ignoring any apparent sudden change at the boundaries of the blocks. Because of this, a sudden jump in the computed Stokes vectors, caused by switching the choice of solutions at the block boundary, will not cause a false alarm.

A fourth aspect of the selection enhancement method is that the processor reports the values of the measured power ratio and the scalar product to an operator of the system, on demand. This enables the operator to observe whether the system has drifted significantly from its calibration.

When the system first begins measurements, it does not report them as valid data until ten blocks of data have been processed. This gives the selection enhancement method time to find solutions for the power parameters $a_1$ and $a_2$ that are consistent with the calibration information for the power ratio and the scalar product between the Stokes vectors. The time period for the recent averages of $a_1$ and $a_2$ cannot be the full specified period initially, so averaging is done only over the shorter history from the beginning to the present, until the beginning becomes more distant than the specified averaging period such as 1 to 10 seconds. The same kind of shorter history is used temporarily when we modify the recent average upon switching the selected solution for one of the power parameters, as described above.

In summary, the procedure for computing the output Stokes vectors, for each cycle of the polarization modulation, is to measure the power values $P_i$ for each detector for the first output Stokes vector during the appropriate half cycle; compute $P_i/\alpha_i$ from the calibration information a, for each detector; assemble these ratios into the column vector p; operate with $D^{-1}$ to produce q according to equation (e19); evaluate A, B and C according to (e22); compute both of the solutions in equation (e23); compute the two possible Stokes vectors s from equation (e18); repeat all of this for the second output Stokes vector; and select the solutions according to the selection methods described above. These are elementary computations that enable us to install a monitoring system on a fiber of unknown loss without the need to calibrate the power levels, and to recover automatically in case an unusual event causes the system to lose track of which solutions are correct for the power parameters.

As with the first hardware embodiment, once the output Stokes vectors $s_1$ and $s_2$ are determined both before and after a change, they can be used to determine the change matrix M by the method previously described.

The three Stokes vectors for the three analyzer states are required to be linearly independent for reasons discussed above, and for some additional reasons described below. Some requirements for the launch states are also discussed below.

As described above, this embodiment has the ability to adjust to the optical power level and to track drift in the laser power, using only three polarized detectors made with inexpensive, imperfect components, without the need for a detector that is precisely polarization independent. Also, for high-sensitivity applications, it is immune to the occasional enhanced noise sensitivity that is found in embodiments 2 and 3. This can be seen by rearranging and differentiating equation (e17), to get an expression for the differential changes dp in the three detector signals, in terms of the differential vector change ds in a measured Stokes vector:

$$dp = \frac{1}{2a} Dds. \tag{e31}$$

Here the matrix D is non-singular because the three analyzer Stokes vectors that comprise its rows are assumed to be linearly independent. Therefore, there is no non-zero differential s-vector movement ds that is annihilated by D, i.e. that will cause zero for the set dp of first-order changes in all three detection signals. In other words, the condition of enhanced noise sensitivity of embodiment 2 does not occur. To make this robust, we want D to be in some sense robustly non-singular, or the three analyzer Stokes vectors to be robustly linearly independent. An example of such a requirement is described in the next paragraph, where it is also applied to the phase detection algorithm.

The phase detection algorithm described above relies on an assumption that at least one of the three detectors will always have a measurable square-wave signal due to the polarization modulation, as does our ability to determine the change matrix without encountering periods of enhance noise sensitivity. If the optical power and degree of polarization are the same for the two output polarization states (i.e. if all of the detector-dependent $\alpha_i$ and $\gamma_i$ parameters and $P_0$ in equation (e16) are the same for both launch polarization states), this requirement is equivalent to requiring that the three analyzer Stokes vectors should be linearly independent. This follows from equation (e17), just as (e31) did. Instead of a differential change ds of a single Stokes vector, we can consider the non-differential change $\Delta p$ that occurs when the output Stokes vector changes from $s_1$ to $s_2$, using the notation $\Delta s = s_2 - s_1$:

$$\Delta p = \frac{1}{2a} D\Delta s. \tag{e32}$$

Linear independence of the three Stokes vectors (from which D is constructed) implies that at least one component of $\Delta p$ is non-zero for any non-zero change $\Delta s$ in the Stokes vectors. The change $\Delta s$ always has the same large magnitude, but can vary in orientation. If the three analyzer Stokes vectors should all lie nearly in one plane through the origin (though not exactly, since they would then be linearly dependent), then $\Delta p$ could still be quite small when $\Delta s$ is nearly orthogonal to that plane. For this reason, we want assurance that the three analyzer Stokes vectors are in some sense "robustly" linearly independent, and not nearly co-planar with the origin in Stokes space, i.e. not nearly on a great circle around the Poincaré sphere. As an example, this requirement might be stated by requiring that the angle between any analyzer Stokes vector and the normal to the plane defined by the other two with the origin (the direction of the "worst-case" $\Delta s$) should be no more than some angle. If that limiting angle is 60 degrees, then when the signal change for two of the detectors is zero, the change for the remaining detector will be no less than half of what it would be if the angle were the ideal value of zero, because the cosine of 60 degrees (proportional to the scalar product) is 0.5. On these grounds, we might require that the angle between any analyzer Stokes vector and the normal to the plane defined by the other two with the origin should be no more than 60 degrees. Equivalently, the angle between any analyzer Stokes vector and the plane of the great circle defined by the other two should be no less than 30 degrees.

If the optical power and/or degree of polarization is different for the two polarization states, equation (e32) would need to be replaced by a more complex set of equations. But for many practical designs the power and DOP values are not likely to be radically different for the two states, so that the error in using just (e32) will not be large enough to change the conclusion, provided the analyzer Stokes vectors are robustly linearly independent. The more complex equations, for cases where power and/or DOP are significantly different for the two launch states, can of course be written and analyzed, but that will not be done here.

Embodiment 5: Three Launch States; Two Analyzer States

Figure 19:
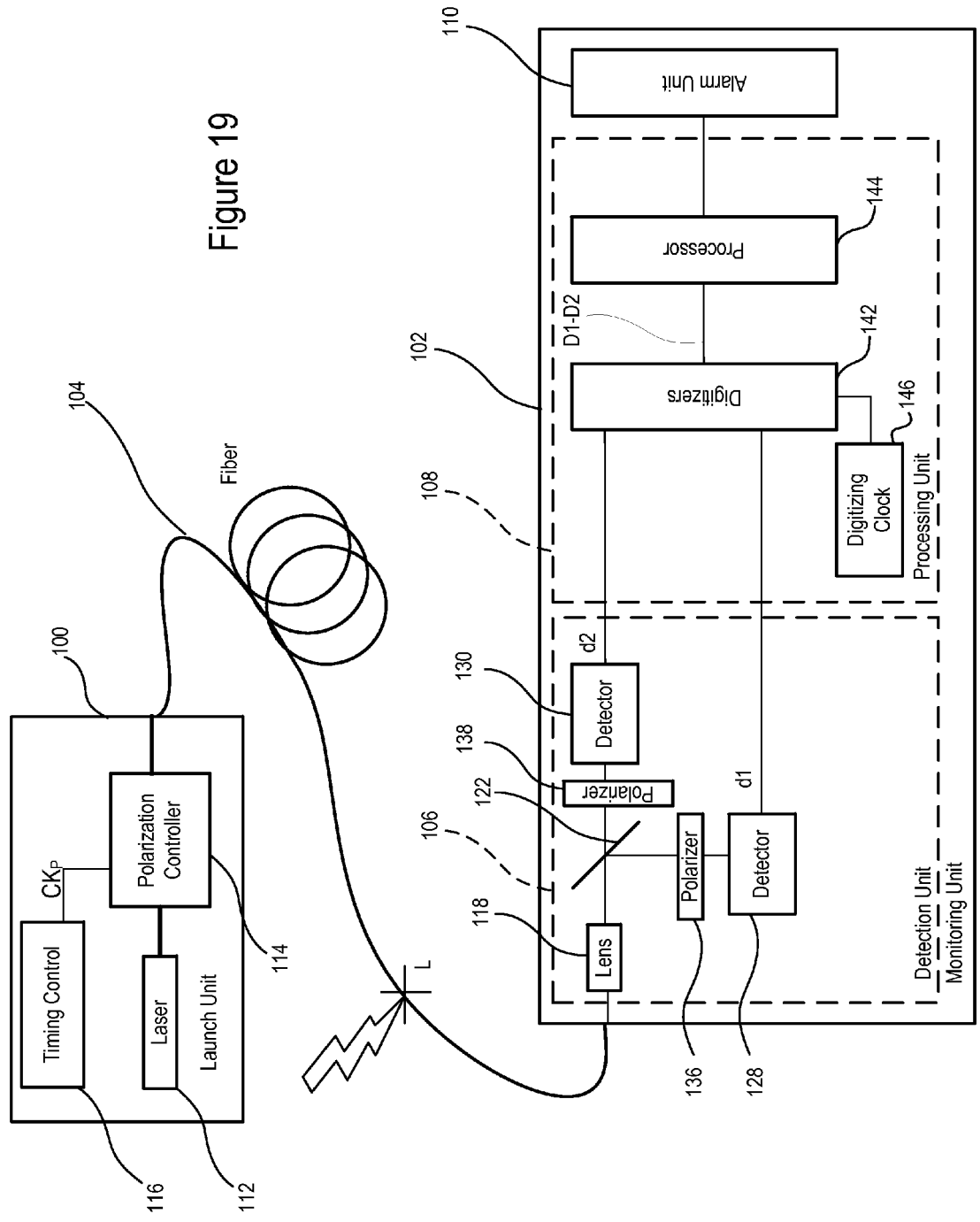
FIG. 19 illustrates schematically a fifth specific embodiment of the invention in which the launch unit uses three launch states and the detection unit uses two analyzer states.

A fifth embodiment using a modified hardware configuration is illustrated in FIG. 19. It is similar to the embodiment described above in connection with FIG. 18, except for specific differences described below that have advantages in particular applications. In particular, this design achieves similar advantages over embodiments 2 and 3, but it achieves this with two polarized detectors instead of three, by using three launch states that are linearly independent and are created with a single variable retarder.

In comparison to the embodiment of FIG. 18, the chief difference of the embodiment shown in FIG. 19 is that detector 126 is omitted, along with its associated beamsplitter 120 and polarizer 134, and its associated A-to-D converter in the digitizer block 142. Another difference, not explicitly apparent in the figures, is that the polarization control unit 114, under command from the timing control unit 116, successively creates three different launch polarization states instead of two in each polarization modulation cycle. These three states are required to have Stokes vector representations that are linearly independent.

Figure 20:
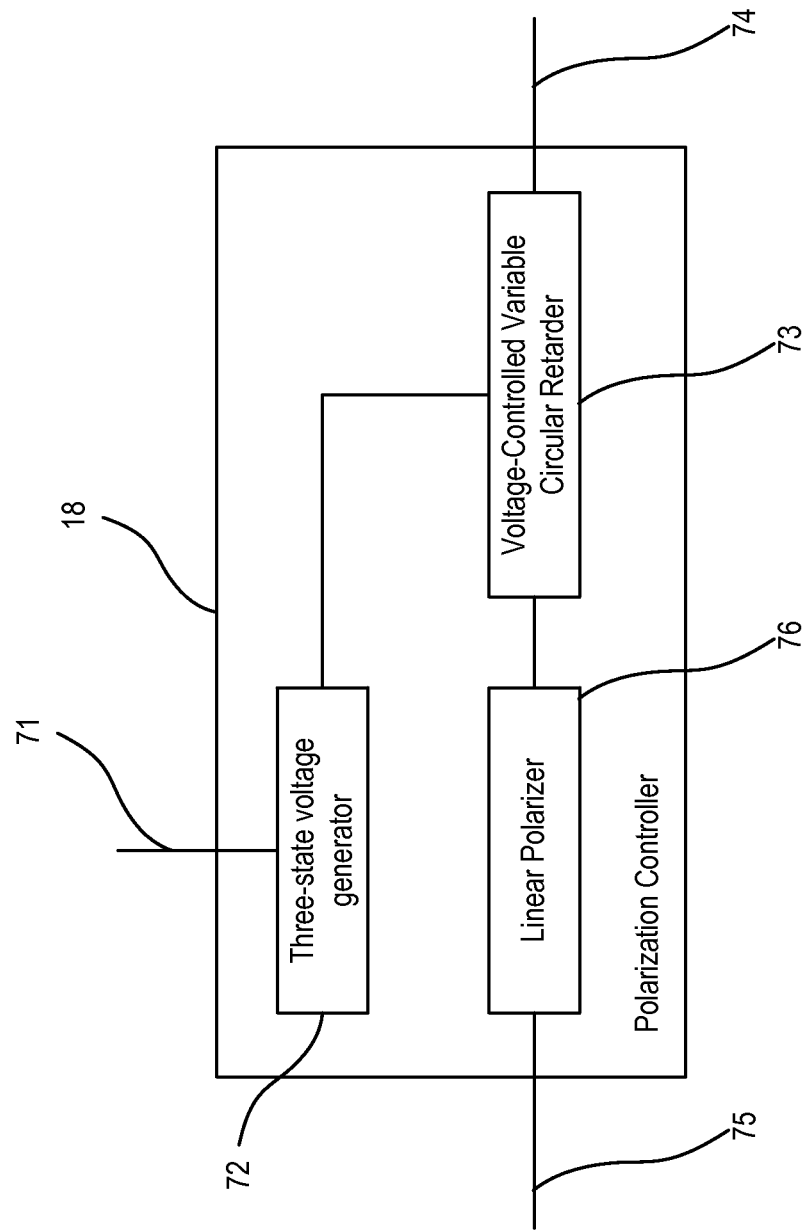
FIG. 20 is a block diagram of a polarization controller of the launch unit of FIG. 19.

Details of the polarization control unit 114 are shown in FIG. 20. Timing information enters the polarization control unit 114 via port 71, which comprises two digital signal lines that are encoded to represent three different states to a three-state voltage generator 72. For each of the three states (i.e., for each phase of the polarization modulation cycle) the voltage generator 72 feeds a different voltage to the variable circular retarder 73, so that it creates three different amounts of circular retardance. To enable the detection system to discriminate between the three states, their time durations are all made different. For this embodiment, the durations of the three phases are approximately 30%, 33% and 37% of the modulation cycle, respectively.

Linearly polarized light (from the laser 112 of FIG. 19) enters the optical port 75 and passes through a tilted linear retarder 76, which converts the light to an elliptical polarization state before it enters the variable circular retarder 73. The variable circular retarder 73 rotates the Stokes vector about the polar axis of the Poincaré sphere by a variable amount, transforming its input light to different elliptically polarized states. It is constructed in a manner similar to the General Photonics PolaSwitch™ product, except that three different input voltages cause rotations of approximately 0, 120 and 240 degrees on the Poincaré sphere relative to the first state (instead of the Stokes-space rotation of approximately 90 degrees indicated for the third embodiment). The linear retarder 76 is designed to place the Stokes vector of the light entering the variable circular retarder 73 on a line of latitude with an angle that approximates an ideal value of 35.26 degrees above the equator on the Poincaré sphere. These conditions will make each of the three launch polarization Stokes vectors have angles of approximately 90 degrees with respect to the other two, making them robustly linearly independent, and providing a better signal-to-noise ratio than if the plane defined by the three Stokes vectors came closer to intercepting the center of the Poincaré sphere (which condition would imply that they were not linearly independent).

The data from this embodiment can be analyzed with effectively the same equations that were applied to the fourth embodiment, except that the meanings of the parameters and variables have changed. This similarity follows from the reciprocity theorem, which states that the optical coupling between a source at a first location and a detector at a second location is the same as the coupling between a source at the second location and a detector at the first location. The reciprocity theorem is well known, and is discussed theoretically, for example, by Larry Di Girolamo, "Reciprocity principle applicable to reflected radiance measurements and the searchlight problem," Applied Optics Vol. 38, No. 15, P. 3196 (1999); and experimentally, for example, by Min-Joong Kim, "Verification of the reciprocity theorem," Applied Optics Vol. 27, No. 13, p. 2645 (1988). The brief discussion below summarizes the mathematics for the fourth embodiment, and then indicates how equations (e16) through (e32) should be reinterpreted for this fifth embodiment.

Equation (e15) is a general formula that relates the "coupling" m (proportional to the fraction of the total power that is detected), for a single launch state and a single analyzer state, to the scalar product d·s of the fixed analyzer-state Stokes vector d with the output Stokes vector s, which varies as the fiber is twisted or bent or otherwise disturbed. These unit Stokes vectors describe the polarized parts of the analyzer state and the transformed launch beam respectively, for cases where the extinction of the analyzer state may be imperfect and the degree of polarization of the launched light may be less than 100%. The equation assumes that changes in the fiber do not alter the degree of polarization. The two calibration parameters $\alpha$ and $\beta$ are defined in terms of the maximum and minimum values that m can attain, as discussed before, and they can be determined by directly measuring the range of m, or by computations from knowledge of the extinction and degree of polarization combined with other information such as detector sensitivity. These two parameters generally depend on which detector and which launch state the equation is applied to. Equation (e16) is the same as (e15) except that a subscript i distinguishes which detector; and it implicitly defines $\gamma_i$ in terms of $\alpha_i$ and $\beta_i$. This is for a single launch state, and the dependence on the launch state is understood.

For this fifth embodiment, equation (e16) still applies, but we adapt it by taking $d_1$ to mean the Stokes vector for the $i^{th}$ one of the three launch states (instead of analyzer states), and s to mean the Stokes vector resulting from a particular one of the two analyzer states (instead of launch states), after it is projected or transformed by the fiber back to the input end of the fiber (instead of forward to the output end). Each $m_i$ is a measured number proportional to the power on a particular detector for the $i^{th}$ launch state, and the parameters $\alpha_i$ and $\beta_i$ or $\alpha_i$ and $\gamma_i$ are defined in the same way as before, to make the expression in equation (e16) range from −1 to +1 for each combination of a detector with a launch state.

We adapt equation (e17) by constructing the matrix D and vector g in exactly the same way from the three $d_i$ vectors and the $\gamma_i$ parameters. For each back-projected analyzer state, equation (e18) then defines the Stokes vector s as before, in terms of the vectors defined by (e19) and the power parameter a. The power parameter a for each projected Stokes s vector is then found by selecting one of the two roots indicated in (e23), according to rules described after equation (e26).

After the two Stokes vectors are found both before and after a change, the change matrix M is determined by the method previously described, and further conversion and/or reduction of the data can then be done for assessment of the disturbance to the fiber. Unlike the matrix determined in the first three embodiments, this matrix does not represent the change in the fiber's "forward" transformation from the input end to the output end. Instead it represents the change in its "reverse" transformation from the output end to the input end. That difference is insignificant in most applications of this sensing method. It is as if the two polarized detectors (detector 30 with polarizer 34 and detector 32 with polarizer 36) actually represented differently polarized light sources, and the three launch states actually represented polarized detectors. A difference is that the two imitation launch states (actually analyzer states) are sampled simultaneously instead of sequentially, and the three imitation analyzer states (actually launch states) are sampled sequentially instead of simultaneously.

In the example of this embodiment, as in the fourth embodiment, each of the two detector signals is digitized 100 times in each 1-millisecond cycle of the polarization modulation. The three phases nominally last 30, 33 and 37 digitized points. For the $i^{th}$ launch state (i=1, 2 or 3), the three $m_i$ values in each cycle will be computed by averaging about 20, 23 and 27 points respectively during the stable parts of the cycle, ignoring 10 points in the vicinity of each transition of the modulated polarization state. It is necessary to determine the phase of the polarization modulation cycle relative to the digitizing process, in order to decide which points to average. As with embodiment 4, we will determine the phase for a 10,000-point (0.1-second) block of data by processing a central section of 1,000 points or 10 polarization modulation cycles. But we now have two detector signals, each with three-phase modulation (instead of three signals with two-phase modulation) so the analysis method is different. The particular method described below differentiates an array of differences between the two detector signals, to create peaks at the locations of transitions between the launch states. If all the $\alpha_i$ and $\gamma_i$ parameters in equation (e16) are the same for all three launch states, then the difference array must have non-zero transitions for at least two of the three points where the launch polarization state changes. That is because otherwise the scalar products of all three launch Stokes vectors, with a vector that is the difference between the two analyzer Stokes vectors, would be the same. That could only be true if the three launch Stokes vectors were linearly dependent, or if the two analyzer Stokes vectors were the same, neither of which is true.

To determine the phase, first we subtract the two detection-signal arrays in the raw data block to create a difference array. Then we add the 10 successive 100-point blocks in this array to create a single 100-point averaged array. Next we digitally differentiate this array (including a difference value for the "circular" transition from point 100 to point 1), and from this we create a new smoothed array, in which each point is the average of about five contiguous points in the original differentiated array (including "circular" averaging at the two ends of the array). Then we create a final data array that is the absolute value of this smoothed array. The peaks in this array represent transitions. This will be convolved with a model array that is constructed by starting with an array of 100 zeros (indexed 1 to 100 in the notation used here), and setting the values to 1 at points 29, 30, 31, 62, 63, 64, 99, 100 and 1, so that it has peaks that are spaced according to the expected transitions. This array is then appended to itself to make a 200-point model array, and this is convolved with the final data array described above. The index of the point where the convolution or the correlation function is a maximum will provide information about the phase of the data. The details of the implementation will of course vary, depending on the programmer. The phase information is used in the same way as for embodiment 4 to determine which points to average to get the three m, values for each launch state in each cycle of the polarization modulation.

Additional Alternatives

The foregoing descriptions of several embodiments illustrate how different combinations of launch states and analyzer states can be used to produce Change Information that can be used to derive measures and make decisions using much the same signal processing steps 4.13, 4.14 and 4.15. It is also envisaged that the signal processing might be modified too. For example, as an alternative to Measure-1 and Measure-2, the Decisions and Reporting process 4.16 may evaluate the Change Information for geometrical or dimensional characteristics of the motion. It is also possible to alter the instrumentation or data-collection method. For example, the launch state of polarization can be modulated or swept back and forth continuously instead of alternated discretely, and, with suitable modification to the signal processing routines, the same information can be extracted from the data. Also different integration patterns (including overlapping patterns) can be devised that may be advantageous in some applications, such as using a symmetric pattern instead of the asymmetric pattern (a first, then b) implied by FIG. 5.

The examples of measures can be computed in multiple ways that may look different but are nevertheless the same, or that are the same except for small differences due to the use of different approximations. Different measures can be devised that embody the same principles to make them substantially free of fading, and these are not necessarily confined to those that can be easily identified as dependent on frequency-domain or time-domain analysis such as illustrated in detail herein. Some examples are given below.

As a simple example of different computational methods achieving the same end, note that the isotropic power spectrum obtained by Fourier analysis of a block of change-space position vectors could also be found by similar analysis of a block of step vectors, because step-vector data is in essence the time derivative of change-space position data. As another example, note that a measure that is computed from an isotropic power spectrum (such as a weighted sum of components) may be the same as a corresponding measure computed using time-domain correlation-function analysis (such as an integral of an autocorrelation function after passing it through a filter) without ever actually doing Fourier analysis or computing a power spectrum.

While the change-space path process of computing Measure-1 is a convenient way to represent the change information and provides an easy means for computing the net angular rotation over different time intervals, this same measure can also be computed by methods that do not involve change space. For example, the rotation angle for a large time interval can be computed from the Stokes vectors at the start and at the end without reference to change space (e.g., by using them to computed a change matrix for the large time interval, then finding the rotation angle implied by the matrix from the formulae used previously to determine the step vector).

As examples of different measures, it is useful to reduce the information in a change-space path by computing various qualitative or quantitative measures that characterize geometric or dimensional motion in change space, because this has implications about the geometric complexity of the physical disturbance to the fiber. It is useful to determine, for example, whether a disturbance chiefly elicits one-dimensional motion in change space, or whether the movements are dominantly in some two-dimensional plane, or spread among all three dimensions; or whether two disturbances are dominantly in the same line or plane or in different lines or planes. There are different ways to analyze the character of motion in change space. As an example of an analysis method, a covariance matrix can be computed for the three vector components of a set of all of the change-space position vectors C over some moderate time interval. The covariance matrix is then diagonalized to find its eigenvectors and eigenvalues. (This technique is encompassed by standard "principle component analysis.") If one eigenvalue is much larger than the other two, the motion is predominantly one-dimensional. Assuming the disturbance is small, if two eigenvalues are comparable and much larger than the third, it is two dimensional, and a mechanical disturbance that created it must have at least a two-parameter nature. The two associated eigenvectors indicate the plane of motion in change space. If two disturbances at nearly the same time have the same plane of motion in change space, there is an increased likelihood that they come from the same place in the fiber. The angle between the lines or planes that characterize two disturbances can be computed as a useful measure, and if it is large there is an increased likelihood that the two disturbances come from different places in the fiber. As another computational method for geometric or dimensional analysis, it is useful to examine the Fourier transforms of the x, y and z components of C(t) before squaring them to produce power spectra, because they contain phase information. If there is a peak or resonance at some frequency, for example, the amplitudes and phases of the three Fourier transforms, evaluated at that frequency, will provide information on both the direction(s) and shape of the oscillation (linear, circular, elliptical, etc.).

In a more detailed example of the use of a geometric measure, the processor determines the change-space position, as prescribed above, once every millisecond, and continuously applies a standard low-pass digital filter to the three streams of position values for the three change space coordinates, storing the filtered change-space position values in a circular buffer with 20 seconds of past data. The filter attenuates information at frequencies higher than 4 Hz. Each 0.1 second, the processor determines the distance between the most recent vector position and the position at a time 10 seconds ago. If this is greater than a threshold set by the user, it examines the changes further by computing the 3×3 covariance matrix for the x, y and z arrays of filtered change-space coordinate values recorded between 10 seconds ago and the present time. Then it determines the largest two eigenvalues for this matrix, and computes the ratio of the larger to the smaller. If this ratio is less than a threshold set by the user (such as 20, indicating that the disturbance has prominent motion in at least two dimensions instead of being chiefly linear), the processor creates notification of a reportable disturbance.

The Decision and Reporting processes using Measure-1 and/or Measure-2 to determine whether a disturbance should be reported can be done in many different ways, and has been done in many different ways in existing products marketed for monitoring and security. Often a measure is a numerical quantity that is compared to a threshold, and the threshold can be adjusted by the user of a monitoring system to optimize the reporting of disturbances that should be reported, and minimize "false positive" reports or false alarms, i.e. disturbances that are reported but should not be. Several layers of discrimination can be used, such as registering an "event" when a threshold is exceeded, but not reporting an "alarm" unless at least some number of events, such as three, occurs within some time period, such as ten seconds. This can be viewed as using one or several measures to construct new measures. As an example, products are commercially available that offer the ability to sum the components of a power spectrum over a selected frequency range to create a measure, updated regularly at short time intervals, that can be compared to a threshold. But instead of instantaneous comparison, it can be effectively averaged over an adjustable time and the average (which is yet another measure) can be compared to a threshold. Exceeding the threshold creates an event, and the user can set up the system so that an alarm is issued if the number of events occurring in some time interval (which is yet another measure) exceeds some particular number.

Representative Applications

Although the above-described embodiments of the invention monitor optical fiber to detect disturbance associated with attempts to tap the fiber or another fiber in the same cable, the invention encompasses other applications where it is desirable to detect disturbances. One such application is the detection of intruders disturbing the fiber when seeking ingress to a protected zone or building. Another such application is the monitoring of vibration by attaching the optical fiber to a structure to be monitored and detecting disturbance of the fiber by the disturbance. The invention also encompasses the measurement of the magnitude and other characteristics of a disturbance such as the relative acoustic power in different frequency bands by monitoring an optical fiber subjected to such audio power.

Embodiments of the present invention advantageously may provide improved performance as compared with previous methods and systems for monitoring for disturbance of an optical fiber by transmitting polarized light through the fiber, especially in terms of reducing susceptibility to fading problems without increasing manufacturing costs and impairing manufacturability by design constraints.

For these reasons, it would be valuable not to require linear or circular filters with specific relationships, but to allow filters associated with either the launch or detection functions to have much more general elliptical polarization states, with only those constraints on their relationships that are necessary to ensure good measurements, and with suitable calibration techniques so that data reduction is sufficiently accurate. This would allow the monitoring unit to be built using "imperfect" parts thereby lowering cost and improving manufacturability.

The entire contents of each of the patents and technical articles mentioned hereinbefore are incorporated herein by reference.

Although embodiments of the invention have been described and illustrated in detail, it is to be clearly understood that the same are by way of illustration and example only and not to be taken by way of limitation, the scope of the present invention being limited only by the appended claims.

We claim:

1. A method of monitoring an optical fiber, comprising:
launching a probe light flux into the fiber, wherein the probe light flux includes a first portion and a second portion in respective launch polarization states that are characterized by linearly independent launch Stokes vectors;
analyzing a received light associated with propagation of the probe light flux in the fiber based on at least two analyzer polarization states that are characterized by Stokes vectors that are linearly independent;
processing detected signals associated with the analyzed received light to determine a measure of change in the fiber, over a period of time that is substantially invariant under a non-reflecting unitary transformation of either the launch polarization states or the analyzer polarization states; and
reporting a disturbance of the fiber based on the determined measure of change.

2. The method of claim 1, wherein probe light flux portions associated with the each of the two linearly independent launch Stokes vectors are alternately launched into the fiber.

3. The method of claim 2, wherein the probe light flux portions associated with each of the two linearly independent launch Stokes vectors are alternately launched into the fiber in a first time interval and alternately launched in a second time interval, wherein the measure of change is determined based on detected signals associated with the first time interval and the second time interval.

4. The method of claim 1, wherein the probe light flux portions associated with the each of the linearly independent launch Stokes vectors are simultaneously launched into the fiber.

5. The method of claim 4, wherein the probe light flux portions associated with each of the two linearly independent launch Stokes vectors are associated with different wavelengths.

6. The method of claim 5, wherein processing the detected signals further comprises identifying detected signal portions associated with the first portion and the second portion of the probe light flux based on the different wavelengths.

7. The method of claim 4, wherein the probe light flux portions associated with each of the two linearly independent launch Stokes vectors are associated with different modulations.

8. The method of claim 7, wherein processing the detected signals further comprises identifying detected signal portions associated with the first portion and the second portion of the probe light flux based on the different modulations.

9. The method of claim 1, wherein the measure of change is determined based on the detected signals associated with a first time interval and a second time interval.

10. The method of claim 1, wherein the measure of change can be derived from one or more vector representations of Poincaré sphere rotations corresponding to change or changes during the period of time.

11. The method of claim 1, further comprising:
determining change information over at least two sub-periods that are subsets of the time period;
determining vector representations of Poincaré sphere rotations corresponding to the change information for the two or more sub-periods; and
determining the measure based partly on relative directional information associated with the two or more vector representations.

12. The method of claim 1, further comprising:
determining change information over at least two sub-periods that are subsets of the time period;
determining vector representations of Poincaré sphere rotations corresponding to the change information for the two or more sub-periods; and
determining the measure based partly on relative displacement information associated with the two or more vector representations.

13. The method of claim 1, further comprising:
accumulating a set of change information representing a sequence of changes during the period of time; and
computing the measure so as to correspond to components of an isotropic power spectrum that can be represented as a sum of the three power spectra for three components of a corresponding sequence of vector representations of Poincaré sphere rotations.

14. The method of claim 13, wherein the disturbance is reported based on a power spectrum corresponding to a sum of squares of the three power spectra.

15. The method of claim 14, wherein the disturbance is reported based on a portion of the power spectrum in one or more selected frequency bands.

16. The method of claim 1, wherein the probe light flux further comprises a third portion, wherein the first portion, the second portion, and the third portion are associated with respective linearly independent launch Stokes vectors.

17. The method of claim 1, wherein the received light associated with propagation of the probe light flux in the fiber is analyzed based on at least three analyzer polarization states that are characterized by Stokes vectors that are linearly independent.

18. The method of claim 1, wherein the received light associated with propagation of the probe light flux in the fiber is analyzed based on at least four analyzer polarization states that are characterized by Stokes 4-vectors that are linearly independent.

19. The method of claim 1, wherein the probe light flux is launched into a first end of the fiber and the received light associated with propagation of the probe light flux in the fiber is obtained at a second end of the fiber.

20. An apparatus for monitoring an optical fiber, comprising:
a probe light source coupled to launch a probe light flux into the optical fiber, wherein the probe light flux includes a first portion and a second portion in respective launch polarization states that are characterized by linearly independent launch Stokes vectors;
a polarization analyzer situated to receive a light flux associated with propagation of the probe light flux in the optical fiber and analyze the received light flux based on at least two analyzer polarization states that are characterized by Stokes vectors that are linearly independent; and
a processor configured to receive detected signals associated with the analyzed received light and determine a measure of change in the fiber over a period of time, wherein the measure of change is substantially invariant under a non-reflecting unitary transformation of either the launch polarization states or the analyzer polarization states, wherein the processor is configured to report a disturbance of the optical fiber based on the determined measure of change.

21. The apparatus of claim 20, wherein the probe light source is configured to provide probe light flux portions associated with the each of the two linearly independent launch Stokes vectors and alternately launch the probe light flux portions into the fiber.

22. The apparatus of claim 21, wherein the probe light flux portions associated with each of the two linearly independent launch Stokes vectors are alternately launched into the fiber in a first time interval and alternately launched in a second time interval, wherein the measure of change is determined based on detected signals associated with the first time interval and the second time interval.

23. The apparatus of claim 20, wherein the probe light source is configured to simultaneously launch the probe light flux portions associated with the each of the linearly independent launch Stokes vectors.

24. The apparatus of claim 23, wherein the probe light source is configured so that the probe light flux portions associated with each of the two linearly independent launch Stokes vectors are associated with different wavelengths.

25. The apparatus of claim 24, wherein the processor is configured to process the detected signals so as to identify detected signal portions associated with the first portion and the second portion of the probe light flux based on the different wavelengths.

26. The apparatus of claim 20, wherein the probe light source is configured so that the probe light flux portions associated with each of the two linearly independent launch Stokes vectors are associated with different modulations.

27. The apparatus of claim 26, wherein the processor is configured to identify detected signal portions associated with the first portion and the second portion of the probe light flux based on the different modulations.

28. The apparatus of claim 20, wherein the processor is configured to determine the measure of change based on detected signals associated with a first time interval and a second time interval.

29. The apparatus of claim 20, wherein the measure of change can be derived from a vector representation of Poincaré sphere rotations corresponding to a change during the period of time.

30. The apparatus of claim 20, wherein the processor is configured to:
determine change information over at least two sub-periods that are subsets of the time period;
determine vector representations of Poincaré sphere rotations corresponding to the change information for the two or more sub-periods; and
determine the measure based partly on relative directional information or relative displacement information associated with the two or more vector representations.

31. The apparatus of claim 20, wherein the processor determines the measure based on four analyzer polarization states that are characterized by Stokes 4-vectors that are linearly independent.

32. The apparatus of claim 20, wherein the probe light source is configured to produce a periodically varying synchronization light flux, and the processor is configured to establish detected signal portions associated with the first and second portions of the probe light flux based on the periodically varying synchronization light flux.

33. The apparatus of claim 32, wherein the probe light source is configured to provide a third portion, wherein the first portion, the second portion, and the third portion are associated with respective linearly independent launch Stokes vectors.

34. The apparatus of claim 20, wherein the probe light source is coupled to launch the probe light flux into a first end of the optical fiber and the polarization analyzer is situated to receive the light flux associated with propagation of the probe light flux in the optical fiber at a second end of the optical fiber.

* * * * *